(12) United States Patent
Thimmaiah et al.

(10) Patent No.: US 10,745,393 B2
(45) Date of Patent: Aug. 18, 2020

(54) SMALL MOLECULAR PROBES, PROCESSES AND USE THEREOF

(71) Applicant: JAWAHARLAL NEHRU CENTRE FOR ADVANCED SCIENTIFIC RESEARCH, Bangalore (IN)

(72) Inventors: Govindaraju Thimmaiah, Bangalore (IN); Nagarjun Narayanaswamy, Bangalore (IN); Kolla Rajasekhar, Bangalore (IN)

(73) Assignee: JAWAHARLAL NEHRU CENTRE FOR ADVANCED SCIENTIFIC RESEARCH, Bangalore (IN)

( * ) Notice: Subject to any disclaimer, the term of this patent is extended or adjusted under 35 U.S.C. 154(b) by 531 days.

(21) Appl. No.: 15/301,952

(22) PCT Filed: Apr. 3, 2015

(86) PCT No.: PCT/IB2015/052463
§ 371 (c)(1),
(2) Date: Oct. 4, 2016

(87) PCT Pub. No.: WO2015/151071
PCT Pub. Date: Oct. 8, 2015

(65) Prior Publication Data
US 2017/0137418 A1 May 18, 2017

(30) Foreign Application Priority Data

Apr. 4, 2014 (IN) .......................... 1819/CHE/2014

(51) Int. Cl.
| | | |
|---|---|---|
| *C07D 417/14* | (2006.01) | |
| *C12Q 1/68* | (2018.01) | |
| *C07D 405/06* | (2006.01) | |
| *C07D 417/06* | (2006.01) | |
| *C07D 277/64* | (2006.01) | |
| *C07D 413/06* | (2006.01) | |
| *C07D 421/06* | (2006.01) | |
| *C09B 23/10* | (2006.01) | |
| *C12Q 1/6818* | (2018.01) | |
| *C12Q 1/6883* | (2018.01) | |
| *G01N 21/64* | (2006.01) | |
| *G01N 33/58* | (2006.01) | |
| *G01N 33/68* | (2006.01) | |

(52) U.S. Cl.
CPC ......... *C07D 417/14* (2013.01); *C07D 277/64* (2013.01); *C07D 405/06* (2013.01); *C07D 413/06* (2013.01); *C07D 417/06* (2013.01); *C07D 421/06* (2013.01); *C09B 23/105* (2013.01); *C12Q 1/6818* (2013.01); *C12Q 1/6883* (2013.01); *G01N 21/6428* (2013.01); *G01N 33/582* (2013.01); *G01N 33/6896* (2013.01); *G01N 2021/6439* (2013.01); *G01N 2333/4709* (2013.01); *G01N 2800/2821* (2013.01)

(58) Field of Classification Search
CPC .............................. C07D 417/14; C12Q 1/6883
USPC ......................................................... 435/6.12
See application file for complete search history.

(56) References Cited

U.S. PATENT DOCUMENTS

| | | | |
|---|---|---|---|
| 4,384,973 | A | 5/1983 | Harnisch |
| 5,223,382 | A | 6/1993 | Ohno |
| 2004/0260093 | A1 | 12/2004 | Czerney et al. |
| 2006/0166368 | A1 | 7/2006 | Berkelman |
| 2006/0280652 | A1* | 12/2006 | Pitner .................. C07D 207/02 422/68.1 |
| 2008/0305489 | A1 | 12/2008 | Thomas et al. |

FOREIGN PATENT DOCUMENTS

| | | |
|---|---|---|
| EP | 0047881 A2 | 3/1982 |
| WO | 2006025887 A2 | 3/2006 |

OTHER PUBLICATIONS

Sun et al. "Fluorescent probe for biological gas SO2 derivatives bisulfite and sulfite" Chem. Comm., 49, 2637-2639. (Year: 2013).*
Bahra, G. et al., "Towards a Structure—RSA Relationship for Non-Linear Optical Materials," Materials Research Society Proceedings, vol. 374, Jan. 1994, 6 pages.
Hara, K. et al., "Molecular Design of Coumarin Dyes for Efficient Dye-Sensitized Solar Cells," Journal of Physical Chemistry B, vol. 107, No. 2, Jan. 16, 2003, available online Dec. 12, 2002, 10 pages.
Prostata, Y. et al., "Polymethine dyes—derivatives of the 7-N,N-dialkylaminocoumarines," Ukrainica Bioorganica Acta, vol. 5, No. 1, 2007, 11 pages. (See English Abstract on p. 10).
Lacivita, E. et al., "Identification of a red-emitting fluorescent ligand for in vitro visualization of human serotonin 5-HT1A receptors," Bioorganic & Medicinal Chemistry Letters, vol. 20, No. 22, Nov. 15, 2010, available online Sep. 21, 2010, 5 pages.
Kim, H. et al., "KCN sensor: unique chromogenic and 'turn-on' fluorescent chemodosimeter: rapid response and high selectivity," Chemical Communications, vol. 47, No. 10, Mar. 14, 2011, available online Jan. 17, 2011, 3 pages.
LV, X. et al., "Ratiometric fluorescence detection of cyanide based on a hybrid coumarin-hemicyanine dye: the large emission shift and the high selectivity," Chemical Communications, vol. 47, No. 48, Dec. 28, 2011, available online Nov. 2, 2011, 3 pages.
Yang, Z. et al., "A new ratiometric and colorimetric chemosensor for cyanide anion based on Coumarin-hemicyanine hybrid," Organic & Biomolecular Chemistry, vol. 10, No. 26, Jul. 14, 2012, available online May 14, 2012, 4 pages.

(Continued)

*Primary Examiner* — Jezia Riley
(74) *Attorney, Agent, or Firm* — Hamre, Schumann, Mueller & Larson, P.C.

(57) ABSTRACT

The present disclosure relates to compounds which function as small molecule fluorescent probes which aid in recognition of specific sequences in DNA and detection of Aβ aggregates. Probes/dyes of the instant disclosure are specific to AT-rich sequences of DNA and Aβ aggregates. These small organic dyes/probes are capable of exhibiting switch-on fluorescence and play an important role in fluorescence spectroscopy, diagnostics, imaging and biomedical applications.

3 Claims, 42 Drawing Sheets
(33 of 42 Drawing Sheet(s) Filed in Color)

(56) References Cited

OTHER PUBLICATIONS

Chen, Y. et al., "A Ratiometric Fluorescent Probe for Rapid Detection of Hydrogen Sulfide in Mitochondria," Angewandte Chemie International Edition, vol. 52, No. 6, Feb. 4, 2013, available online Jan. 3, 2013, 4 pages.

Dubar, F. et al., "The Ferroquine Antimalarial Conundrum: Redox Activation and Reinvasion Inhibition," Angewandte Chemie International Edition, vol. 52, No. 30., Jul. 22, 2013, available online Jun. 13, 2013, 4 pages.

Liu, X. et al., "A coumarin-indole-based near-infrared ratiometric pH probe for intracellular fluorescence imaging," Analyst, vol. 138, No. 21, Nov. 7, 2013, available online Aug. 8, 2013, 9 pages.

Liu, J. et al., "Simultaneous Fluorescence Sensing of Cys and GSH from Different Emission Channels," Journal of the American Chemical Society, vol. 136, No. 2, Jan. 15, 2014, available online Dec. 23, 2013, 3 pages.

McCallum, M. et al., "A fluorescence-based high throughput assay for the determination of small molecule-human serum albumin protein binding," Analytical and Bioanalytical Chemistry, vol. 406, No. 7, Mar. 2014, available online Jan. 5, 2014, 19 pages.

An, K. et al., "The Synthesis and Light Absorption Behaviour of Novel Coumarin Chromophores," Journal of the Korean Chemical Society, vol. 58, No. 3, Jun. 2014, 6 pages.

ISA European Patent Office, International Search Report and Written Opinion Issued in Application No. PCT/IB2015/052463, dated Oct. 28, 2015, WIPO, 17 pages.

International Bureau of WIPO, International Preliminary Report on Patentability Issued in Application No. PCT/IB2015/052463, dated Jul. 20, 2016, WIPO, 13 pages.

* cited by examiner

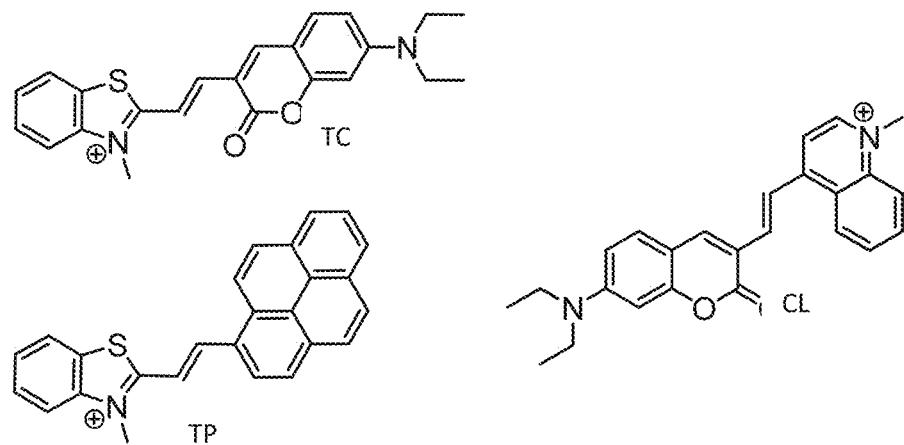

| Code | DNA duplex | Sequence |
|---|---|---|
| $(AT)_{10}$ | $dA_{10}$-$dT_{10}$ | 5'-AAAAAAAAAA-3'<br>3'-TTTTTTTTTT-5' |
| $(GC)_{10}$ | $dG_{10}$-$dC_{10}$ | 5'-GGGGGGGGGG-3'<br>3'-CCCCCCCCCC-5' |
| $(AT)_{20}$ | $dA_{20}$-$dT_{20}$ | 5'-AAAAAAAAAAAAAAAAAAAA-3'<br>3'-TTTTTTTTTTTTTTTTTTTT-5' |
| $d(AATT)_5$ | $d(AATT)_5$ | 5'-AATTAATTAATTAATTAATT-3'<br>3'-TTAATTAATTAATTAATTAA-5' |
| $(D1)_{mix}$ | mixed DNA | 5'- CGATAAGCGCTTATCG-3'<br>3'-GCTATTCGCGAATAGC-5' |
| $(D2)_{mix}$ | mixed DNA | 5'- CGGTACCGCGGTACCG -3'<br>3'-GCCATGGCGCCATGGC-5' |

SMALL MOLECULAR PROBES, PROCESSES AND USE THEREOF

CROSS REFERENCE TO RELATED APPLICATIONS

The present application is a U.S. National Phase of International Patent Application No. PCT/IB2015/052463, entitled "SMALL MOLECULAR PROBES, PROCESSES AND USE THEREOF", filed on Apr. 3, 2015, which claims priority to Indian Patent Application No. 1819/CHE/2014, entitled "SMALL MOLECULAR PROBES, PROCESSES AND USE THEREOF", filed on Apr. 4, 2014, the entire contents of each of which are hereby incorporated by reference for all purposes.

TECHNICAL FIELD

The present disclosure relates to the field of molecular biology, fluorescence spectroscopy, cell biology, immuno-histochemistry and analytical chemistry. More particularly, the present disclosure relates to small molecular probes (biomolecules) which are specific to AT rich sequences of DNA and Aβ aggregates.

Further, the present disclosure relates to method for preparing the small molecular probes and their various applications in fields of fluorescence spectroscopy, diagnostics, imaging, biomedical applications etc.

BACKGROUND OF THE DISCLOSURE

A fluorophore (or fluorochrome, similarly to a chromophore) is a fluorescent chemical compound that can re-emit light upon light excitation. Fluorophores typically contain several combined aromatic groups, or plane or cyclic molecules with several π bonds. Fluorophores are sometimes used alone, as a tracer in fluids, as a dye for staining of certain structures, as a substrate of enzymes, or as a probe or indicator (when its fluorescence is affected by environment such as polarity or ions). But more generally it is covalently bonded to a macromolecule, serving as a marker (or dye, or tag, or reporter) for bioactive reagents (antibodies, peptides, nucleic acids). Fluorophores are notably used to stain tissues, cells, or materials in a variety of analytical methods, i.e., fluorescent imaging and spectroscopy.

Small organic dyes capable of exhibiting switch-on fluorescence through sequence specific interaction with nucleic acids play an important role in fluorescence spectroscopy, diagnostics, imaging and biomedical applications. Selective targeting of double-stranded (ds) DNA using organic dyes offers powerful strategies to develop i) probes for molecular biology and immunohistochemistry, flow cytometry and DNA quantification, ii) genome-specific binders of potential therapeutic interest, and iii) treating gene-related human diseases especially cancer, parasitic and viral infections. In this regard, various sequence-specific small fluorescent molecules have been developed for biological assays including cell imaging and DNA-quantification in cells.

The discovery of DNA as a genetic material and its double helical structure has led to numerous studies directed at understanding DNA-small molecules interaction. Typically, small molecules interact with DNA in two modes viz. intercalation and minor groove binding among other interactions. The research efforts of Dervan and Lown set forth the foundation for developing series of small molecules with affinity for binding to adenine-thymine (AT)-rich minor groove of B-DNA.

4',6-Diamidino-2-phenylindole (DAPI) and bis-benz-amides (Hoechst dyes) are some of the well-studied minor groove nuclear staining agents. Unfortunately, these blue emitting DNA binders require ultraviolet (UV) light for excitation and the prolonged UV-illumination is known to cause cellular DNA damage through free radical generation which eventually leads to cell death.

Despite the selective binding to AT-rich minor groove of DNA, under certain conditions, Hoechst dyes are prone to bind GC-rich sites and also show binding affinity towards single-stranded (ss) DNA and RNA. Similarly, DAPI can bind to RNA and high concentrations are required for imaging, limiting its use only to fixed cells. Recently, cyan and green fluorescent DNA-selective probes such as BENA435 and C61 have been reported. However, these probes upon binding to DNA show fluorescent enhancement with low quantum yields. Thomas et al. recently reported a dinuclear ruthenium(II) polypyridyl complex as a DNA-staining probe, but high concentration of dye is required for cellular imaging.

Apart from these molecules, a large number of cyanine dyes have been extensively used in DNA gel staining, microchip-based DNA sensing and fluorescence staining of DNA in cell. Among the cyanine-family dyes, thiazole orange (TO) and yellow orange (YO) are two important classes of fluorescence probes which show significant fluorescence enhancement upon binding with DNA. Further, the homodimeric forms of TOTO-1 and YOYO-1 are found to be highly sensitive for DNA detection. However, these cyanine-based probes shows significant fluorescence enhancement in presence of RNA and ssDNA. Later, two other class of cyanine dyes such as SYBR® green I and PicoGreen I have been developed and successfully used for DNA staining in picogram scale, although they show fluorescence enhancement in presence of ssDNA.

The limitations of existing probes discussed above necessitate the need for developing highly specific DNA-selective probes with: i) long-wavelength excitation/emission, ii) strong switch-on fluorescence, iii) increased cell permeability, iv) non-toxicity to live cells and v) base pair specificity and fidelity to double stranded (ds) DNA.

Further, Alzheimer's disease (AD) and Frontotemporal dementia are forms of dementia characterized by deposition of amyloid plaques in the brain. These plaques are majorly composed of peptides Aβ40 and Aβ42, which are derived from neural cell surface protein called amyloid precursor protein (APP) by the action of secretase enzymes (β and γ secretase).

There is no cure for AD, once diagnosed based on cognitive state, patient is already in an advanced stage which worsen as time progresses and finally leads to death. The only strategy which could help the patient is the early diagnosis of Alzheimer's disease (AD), which is a major concern in the present situation.

The neurodegeneration and subsequent progressive deterioration in cognitive ability are hallmark symptoms of this incurable syndrome. The $A\beta_{42}$ peptide with 42 amino acids has been shown to be highly susceptible to aggregation and toxic behavior among all the Aβ peptides. Thus, $A\beta_{42}$ is an attractive biomarker to target for diagnosis and therapeutics of AD. One of the major problems in the diagnosis of AD is the lack of effective methods for the early detection of $A\beta_{42}$ aggregates. While diagnosis of AD is traditionally based on behavioral tests or cognition in patients, several imaging technologies such as positron emission tomography (PET),[5] magnetic resonance imaging (MRI), and single-photon emission computed tomography (SPECT) have been developed for the detection of Aβ$_{42}$ aggregates. However, these technologies are still limited by several obstacles, like long data acquisition time, radioactive exposure, poor resolution and need of expensive equipment. Optical imaging using fluorescent and colorimetric probes has emerged as a potential alternative technique as it offers real-time, non-radioactive, high-resolution imaging for inexpensive diagnostics and screening of drugs for AD.

Thioflavin T (ThT) is the most extensively used fluorescence probe for the in vitro detection and staining of Aβ aggregates. However, it suffers from poor selectivity and often leads to false detection. In the past few years, derivatives of oxazine, BODIPY, curcumin, styryl have been developed and used as fluorescence probes for Aβ aggregates.

An ideal fluorescence probe must exhibit certain characteristic properties to be used as a diagnostic probe for Aβ aggregates in AD viz., i) high specificity and strong binding affinity, ii) emission in the optical window of 500-750 nm with a large Stokes shift, iii) switch-on fluorescence change upon binding with Aβ aggregates, and iv) ability to rapidly cross the blood brain barrier (BBB). Further, mixed dementia is a condition in which abnormal characteristics of more than one type of dementia occur simultaneously and, in such cases, determining the specific type of neurodegenerative disorder in the patient is very crucial. Therefore, there is an urgent need for developing probes which could selectively differentiate toxic aggregates. Unfortunately, there is lack of studies on probes that selectively differentiate plaques responsible for any specific disorder. Even in fluorescence probes, selectivity is the major issue, as most of them fluoresce upon binding to forced or artificially formed protein aggregates generally observed in all kinds of dementia. Moreover, colorimetric detection of Aβ aggregates using antibodies has been demonstrated; however, this technique is complicated and expensive.

ThT has been extensively used to stain Aβ aggregates for the past few decades. This probe mainly consists of electron donating (N,N-dimethylaniline) and electron withdrawing (benzothiazole) moieties. However, as mentioned above, this probe suffers from many drawbacks.

Therefore, there is a need for developing selective fluorometric and colorimetric probes based on simple organic molecules, which are easy to handle and offer quick detection and overcome the drawbacks of the prior art dyes/probes and function as selective probes for Aβ aggregates compared to other protein aggregates.

The present disclosure overcomes the limitations of the prior art by providing small molecular probes which are highly specific to AT-rich sequences of DNA vis-à-vis single stranded DNA, RNA and monomeric proteins and probes specific for Aβ aggregates compared to other protein aggregates.

STATEMENT OF THE DISCLOSURE

The present disclosure relates to a compound of Formula I; a compound of Formula V; a compound of Formula VI or its isomer; a process of preparing compound of Formula I; a process of preparing dimer of compound of Formula I; a process of preparing compound of Formula V; a process of preparing compound of Formula VI; a process of preparing the isomer of compound of Formula VI; a method for detecting AT rich sequence in a sample; a method for detecting parasite in a sample; a method for detecting Aβ aggregate in a sample; a method for diagnosing disease selected from group comprising Alzheimer's disease, Frontotemporal Dementia and a combination thereof in a subject; a compound of Formula I, Formula V or Formula VI for use in detecting AT rich sequence or Aβ aggregate; a compound of Formula I, Formula V or Formula VI for use in diagnosing disease selected from group comprising malaria, Frontotemporal dementia and Alzheimer's disease or a combination thereof; a method of fluorescing AT rich DNA; a method of fluorescing Aβ aggregate a kit comprising compound of Formula I, Formula V or Formula VI and combinations thereof, optionally along with an instruction manual.

BRIEF DESCRIPTION OF THE ACCOMPANYING FIGURES

This application contains at least one drawing executed in color. Copies of this patent or patent application publication with color drawing(s) will be provided by the Office upon request and payment of the necessary fee.

In order that the disclosure may be readily understood and put into practical effect, reference will now be made to exemplary embodiments as illustrated with reference to the accompanying figures. The figures together with the detailed description below, are incorporated in and form part of the specification, and serve to further illustrate the embodiments and explain various principles and advantages, in accordance with the present disclosure where:

FIG. 1 depicts molecular structures of designed probe (TC, CL and TP) and DNA (with sequence information) used in this study.

FIG. 2 depicts A) fluorescence spectra of all the probes TC, CL and TP (10 μM) in presence of $(AT)_{10}$ and $(GC)_{10}$ in Tris-HCl buffer (100 mM, pH=7.4) solution, a: TC+(AT)$_{10}$; b: TC+(GC)$_{10}$; c: TC; d: CL; e: CL+(AT)$_{10}$; f: CL+(GC)$_{10}$; g: TP; h: TP+(AT)$_{10}$; i: TP+(GC)$_{10}$.
B) Photographs of TC and TC+(AT)$_{10}$ samples illuminated under UV light (365 nm).
C) Fluorescence spectra of probe TC (10 μM) in presence of various dsDNAs, a: $(AT)_{20}$; b: $(AT)_{10}$; c: $(D1)_{mix}$; d: $(D2)_{mix}$; e: $(GC)_{10}$; f: TC.
D) Fluorescence response of probe TC (10 μM) with increasing concentration of $(AT)_{20}$, $(AT)_{10}$, $(GC)_{10}$, $(D1)_{mix}$ and $(D2)_{mix}$ upon excitation at 521 nm.

FIG. 3 depicts: A) Plot of fluorescence intensity of increased concentration of TC (0-20 μM) in presence of fixed concentrations (12 μM) of $(AT)_{20}$, $(AT)_{10}$, $(D1)_{mix}$, $(D2)_{mix}$. B) and C) Agarose gel-electrophoresis of dsDNAs followed by staining the bands with probe TC and ethidium bromide respectively. Lane 1-4: $(AT)_{20}$, $(D1)_{mix}$, $(D2)_{mix}$ and $(GC)_{10}$ respectively. Inset ring (red) in (B) shows non staining of $(GC)_{10}$ band by TC. Inset ring (red) in (C) shows staining of $(GC)_{10}$ band by ethidium bromide.

FIG. 4 depicts: A) Melting curves of $(AT)_{10}$ and $(AT)_{20}$ in the absence and presence of probe TC. B) Melting curves of $(GC)_{10}$ and $(D2)_{mix}$ in the absence and presence of TC. C) Summary of melting temperatures (Tm) of melting curves shown in (A) and (B).

FIG. 5 depicts confocal fluorescence microscope images of HEK293 cells incubated (at 37° C. for 30 min) with A) TC (5 μM), B) anti-tubulin antibody (α-Tubulin marker (5 μM), C) Hoechst 33258 (5 μM) and D) differential interference contrast (DIC, bright field image) of HEK293 cells respectively. Overlay fluorescence images: E) (A) and (C), F) (A) and (B), G) (A), (B) and (C). H) (A) and D). Scale bar: 5 μm. Images captured by Carl Zeiss Laser Scanning Microscope (LSM510 META).

FIG. 6 depicts DNase I and RNase digestion studies in HEK293 cell lines. Nuclear DNA staining of treated and untreated cells with DNase I (100 µg/mL) and RNase (40 µg/mL) using TC (red) and Hoechst 33258 (blue). Scale bar: 5 µm. Fluorescence images captured by Carl Zeiss Laser Scanning Microscope (LSM510 META).

FIG. 7 depicts that Thiazole-coumarin (TC) exhibits strong fluorescence enhancements in presence of DNA containing AT-base pairs while being non-fluorescent with DNA containing only GC-bases pairs, single-stranded DNA, RNA and proteins. The fluorescence staining in HeLa S3 and HEK293 cells and nuclease enzymes digestion studies reveal cell permeability, non-toxicity and selective staining of cell nucleus by TC over cytoplasm. Images captured by Carl Zeiss Laser Scanning Microscope (LSM510 META).

Figure 16:
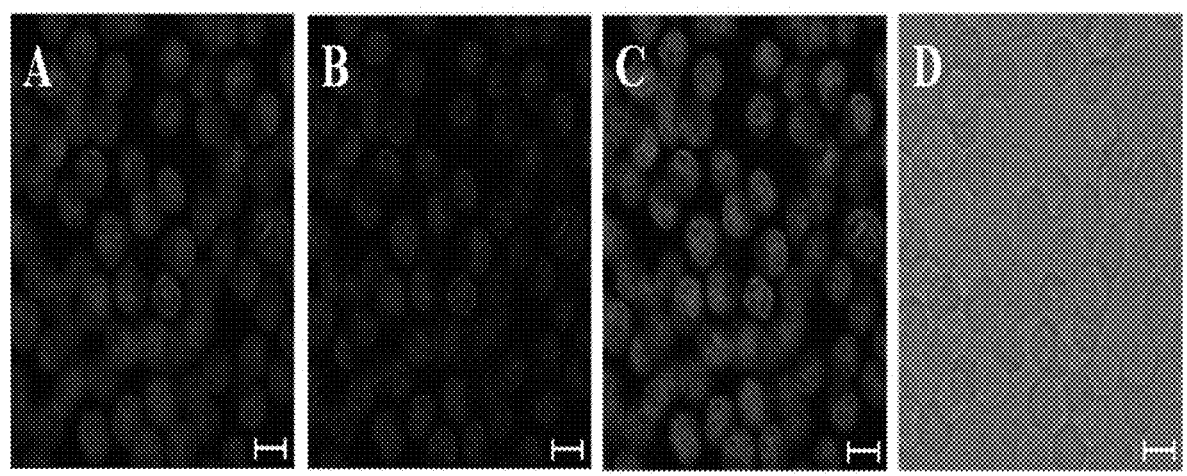

FIG. 16 depicts nuclear DNA staining of HeLa S3 cell lines using (A) probe TC (red), and (B) Hoechst 33258 (blue). (C) Overlay image of (A) and (B). (D) Bright field image of the HeLa S3 cell lines (grey). Scale bar: 10 µm. Images captured by Carl Zeiss Laser Scanning Microscope (LSM510 META).

Figure 17:
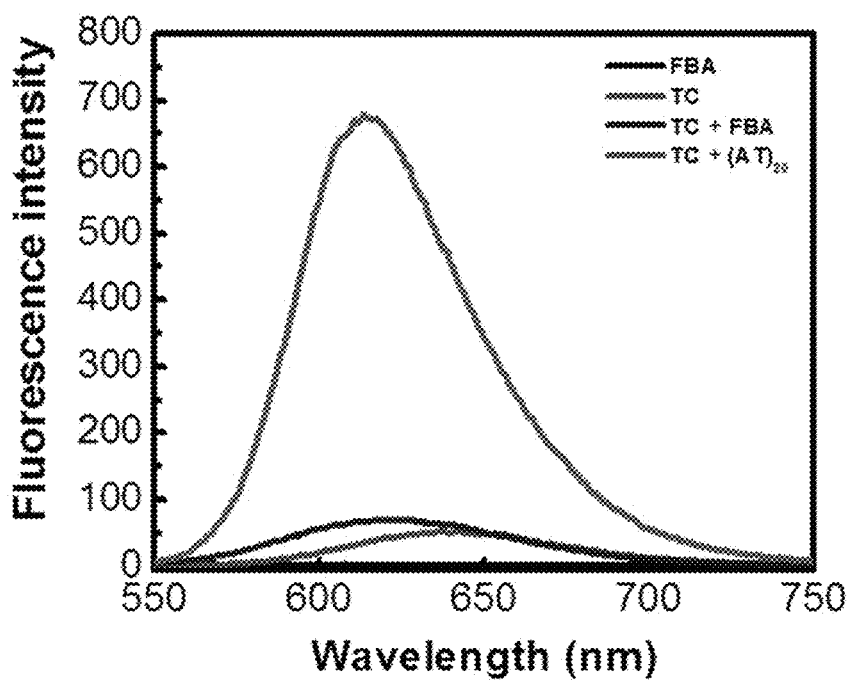

FIG. 17 depicts fluorescence spectra of TC (10 µM) in the presence of $(AT)_{20}$ and Fetal bovine serum albumin (FBA) in Tris-HCl buffer (100 mM, pH=7.4) upon excitation at 521 nm.

Figure 18:
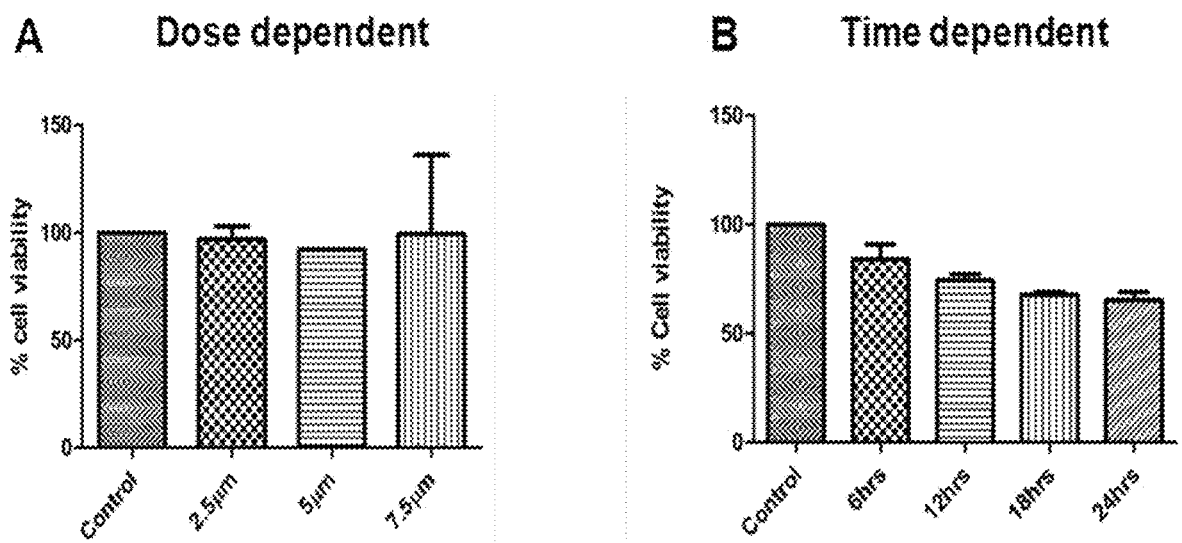

FIG. 18 depicts MTT-assay of HEK293 cells. (A) dose dependent cell viability by taking 2.5 µM, 5 µM and 7.5 µM of probe TC and water as control, (B) Time dependent MTT-assay for up to 24 h using 5 µM of probe TC mean±SEM.

Figure 19:
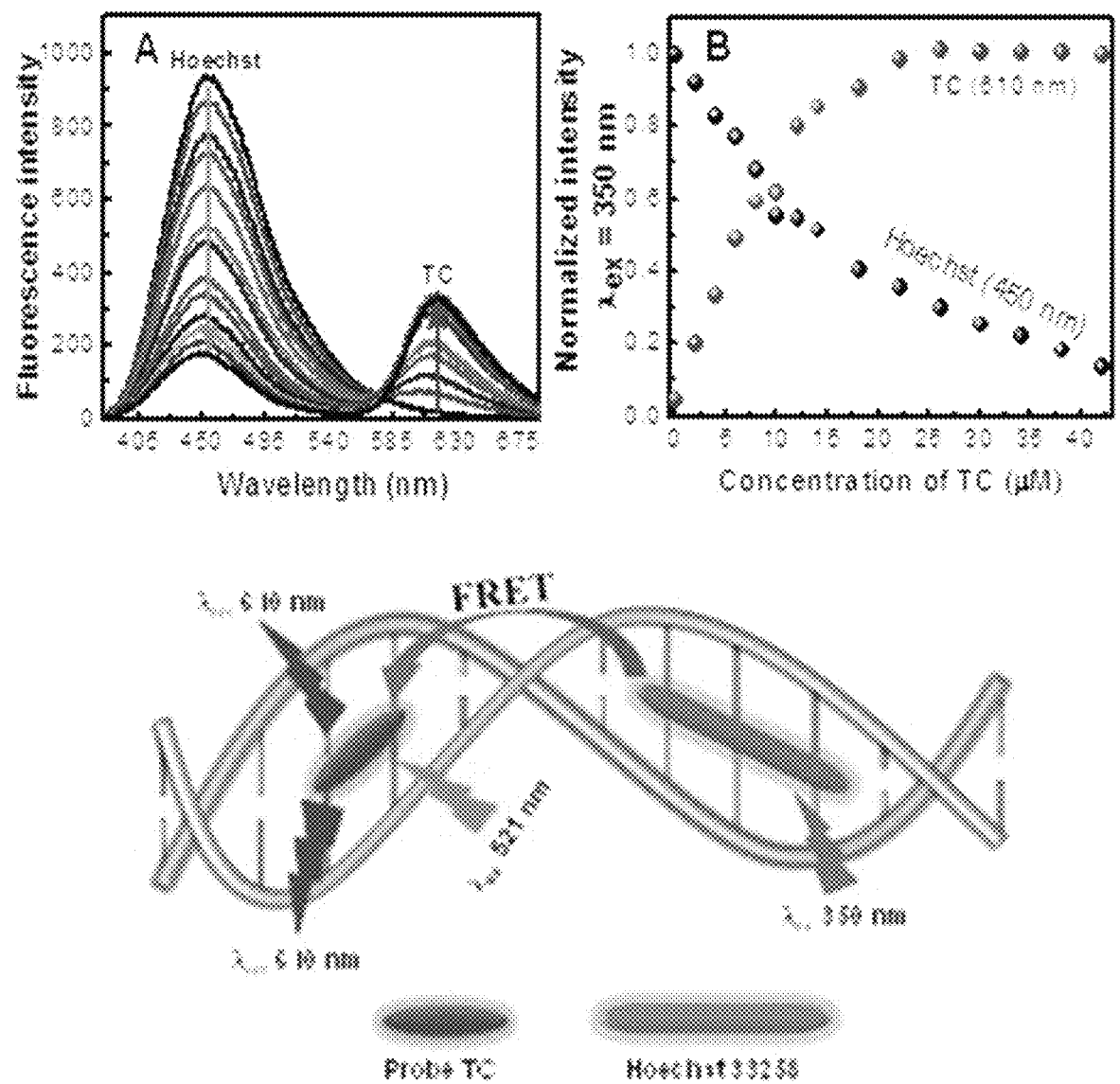

FIG. 19 depicts FRET study of Hoechst-TC (donor-acceptor) pair in presence of dsDNA. A) Fluorescence spectra of preformed Hoechst (4 µM)+$(AT)_{20}$ complex with increasing concentration of TC from 0 µM to 40 µM. B) Fluorescence intensity of Hoechst at 450 nm and TC at 610 nm upon excitation at 350 nm of Hoechst (4 µM)+$(AT)_{20}$ with increasing concentration of TC.

Figure 20:
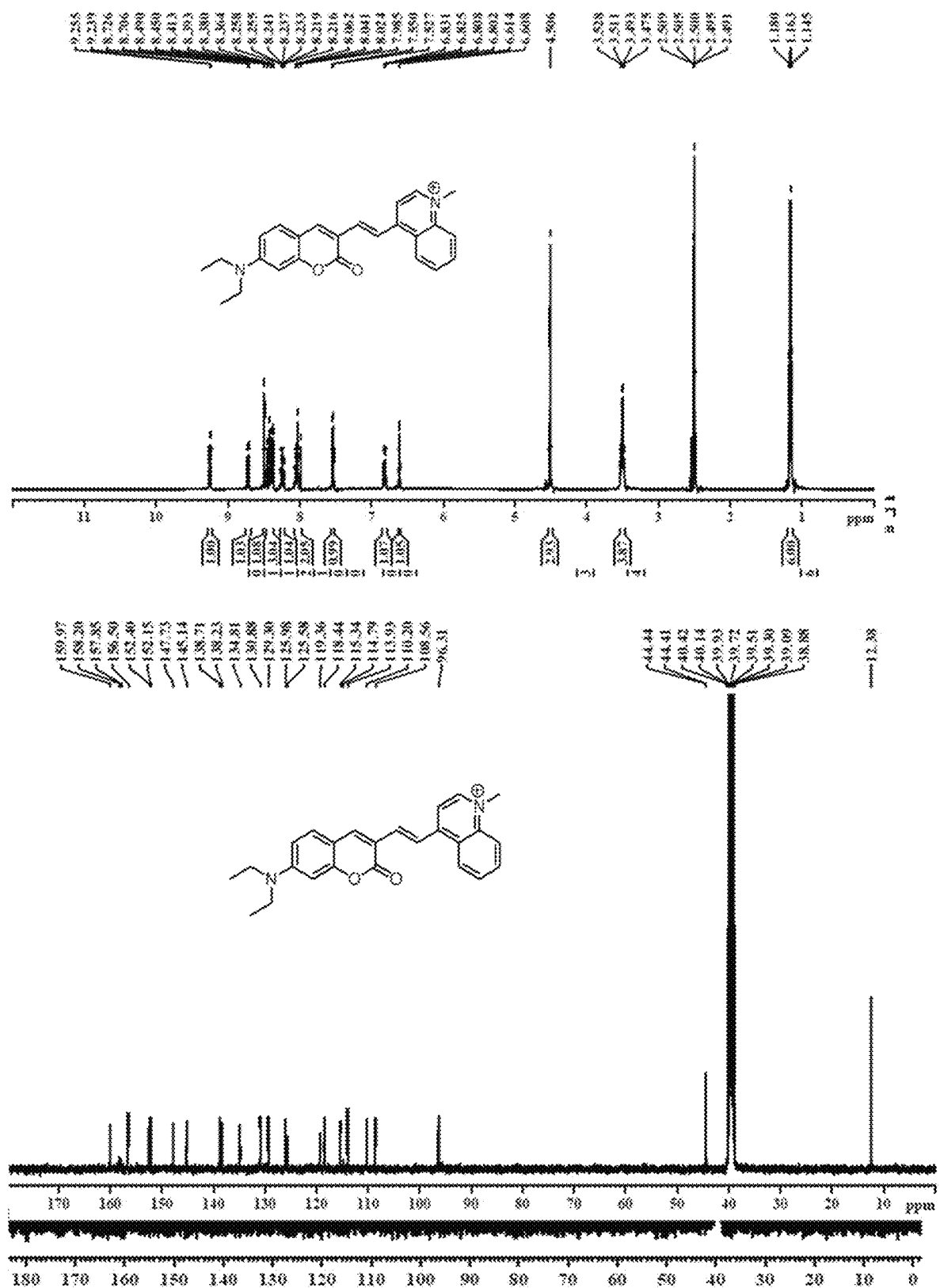
Figure 21:
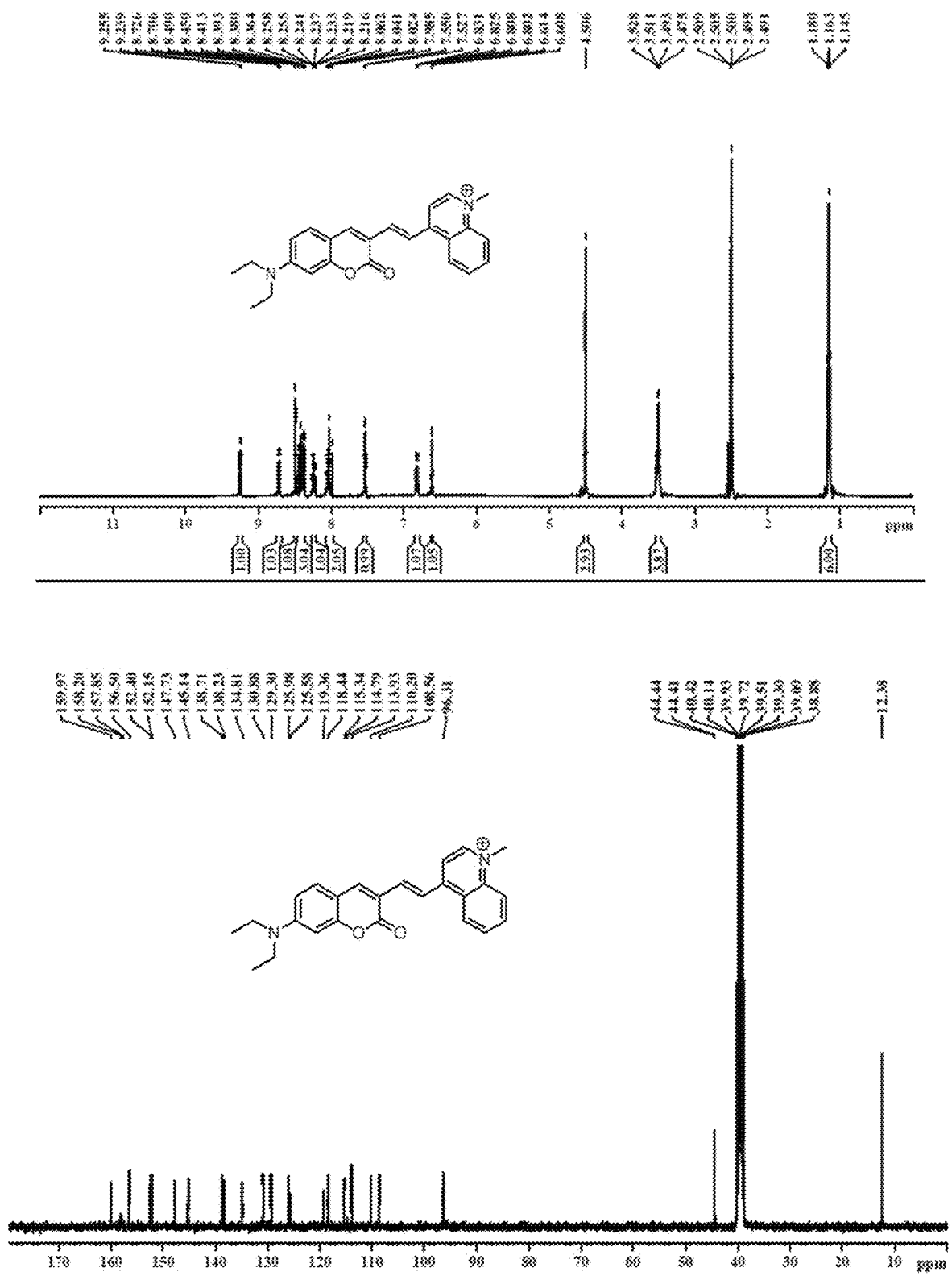
Figure 22:
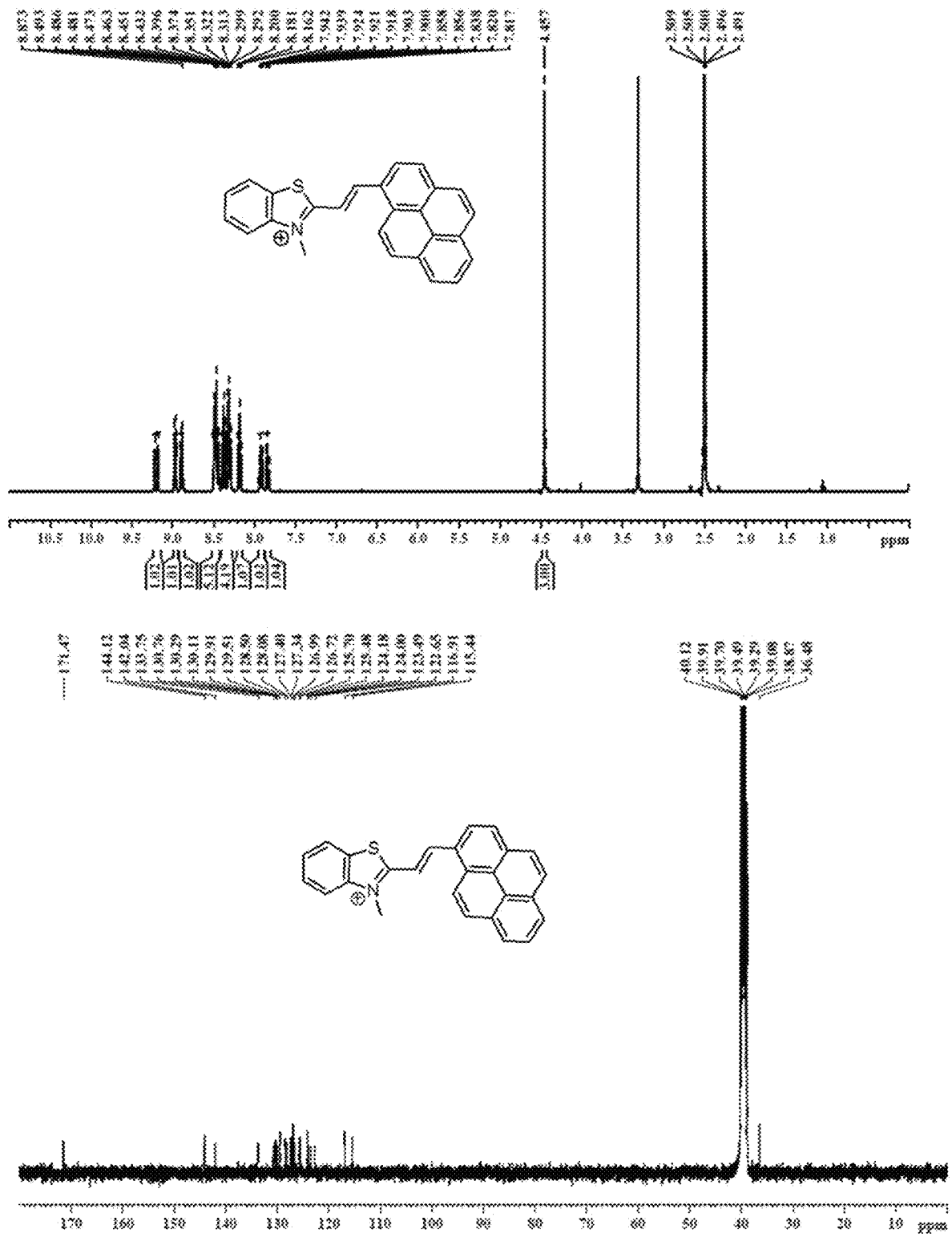

FIG. 20 depicts $^1$H and $^{13}$C-NMR spectra of probe TC.
FIG. 21 depicts $^1$H and $^{13}$C-NMR spectra of probe CL.
FIG. 22 depicts $^1$H and $^{13}$C-NMR spectra of probe TP.

Figure 23:
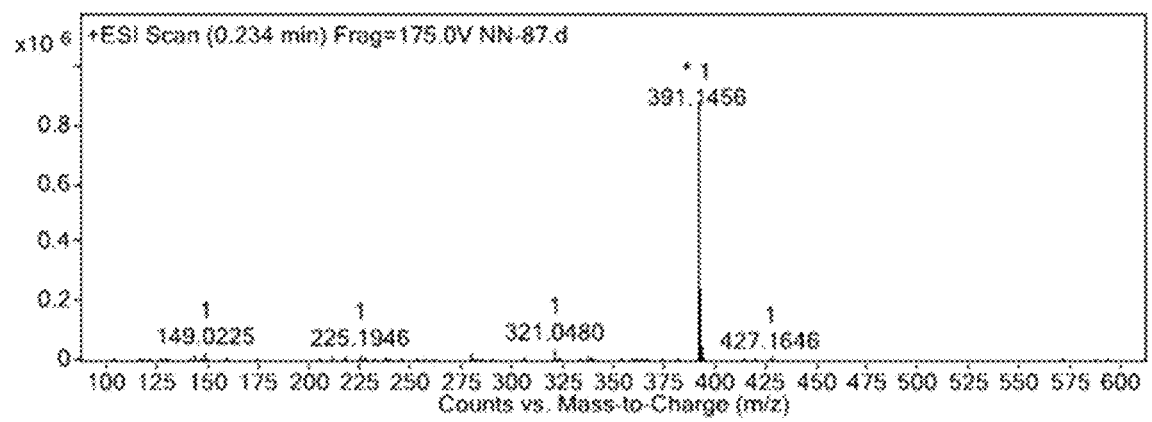
Figure 24:
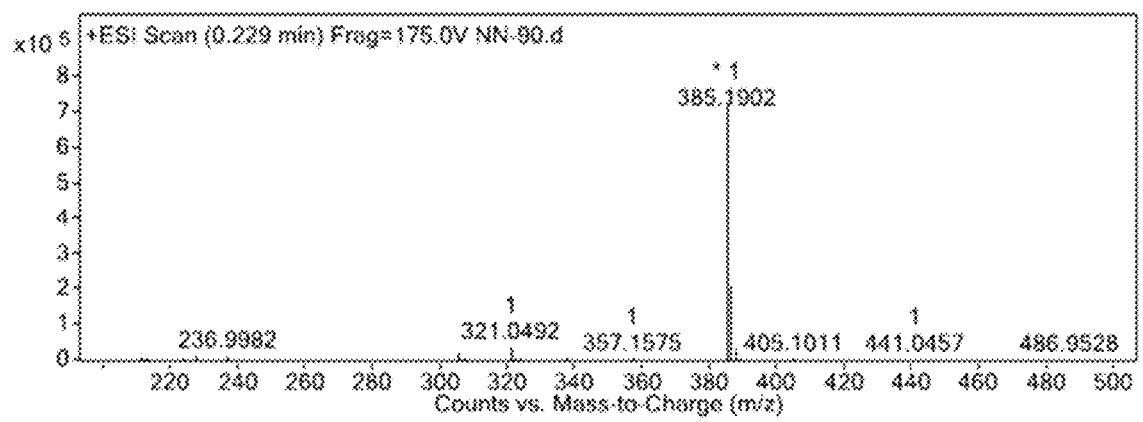
Figure 25:
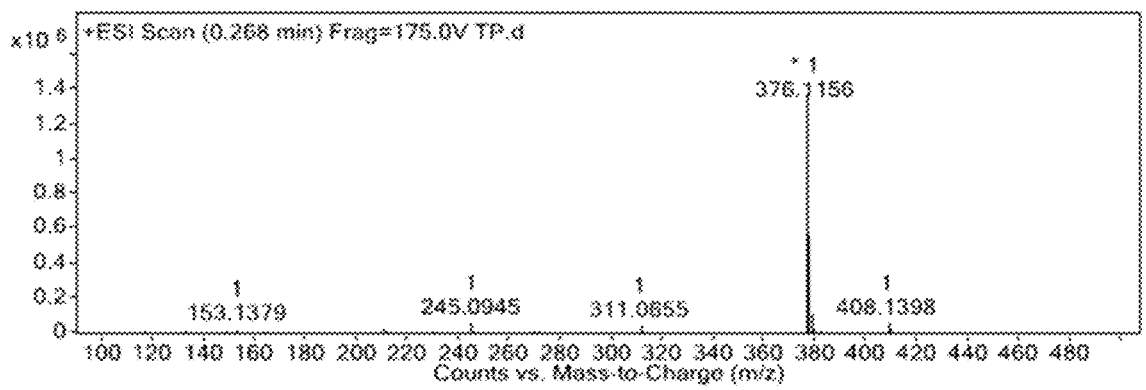

FIG. 23 depicts HRMS spectrum of probe TC.
FIG. 24 depicts HRMS spectrum of probe CL.
FIG. 25 depicts HRMS spectrum of probe TP.

Figure 26:
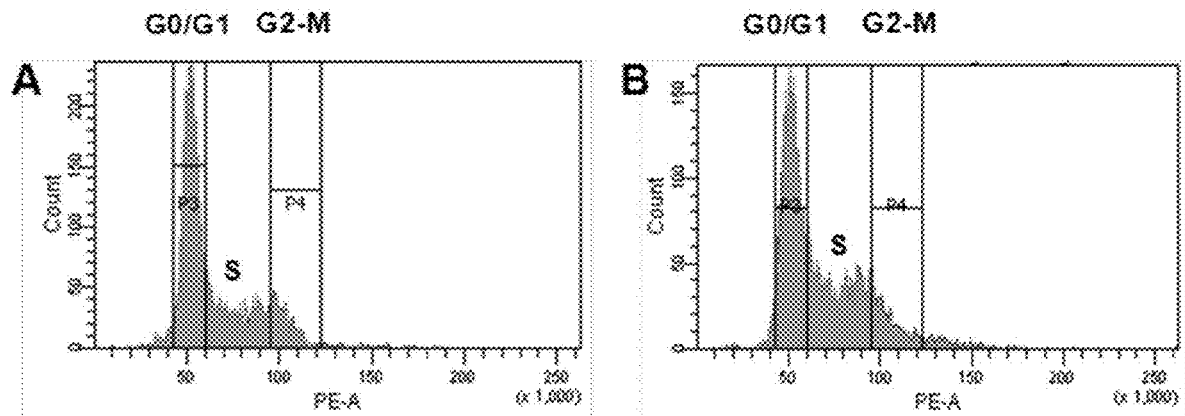

FIG. 26 depicts Cell cycle analysis of HEK293 cells by staining with PI and probe TC. HEK293 cells stained with 6 µg of PI and TC for 30 min. FACS analysis is done by FACS aria instrument. A) Cells stained with PI and B) with Probe TC. P3: (G0/G1), S (synthesis) and P4 (G2-M) are subpopulation of different phase of cell cycle cells.

Figure 27:
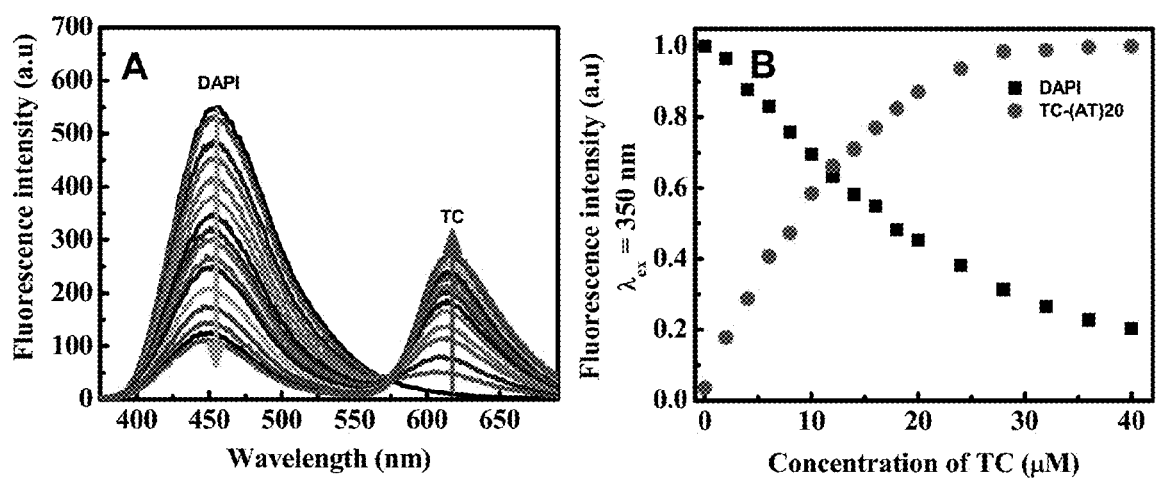

FIG. 27 depicts FRET study of DAPI-TC (donor-acceptor) pair in presence of dsDNA. A) Fluorescence spectra of preformed DAPI (4 µM)+$(AT)_{20}$ complex with increasing concentration of TC from 0 µM to 40 µM. B) Fluorescence intensity of DAPI at 450 nm and TC at 610 nm upon excitation at 350 nm of DAPI (4 µM)+$(AT)_{20}$ with increasing concentration of TC.

Figure 28:
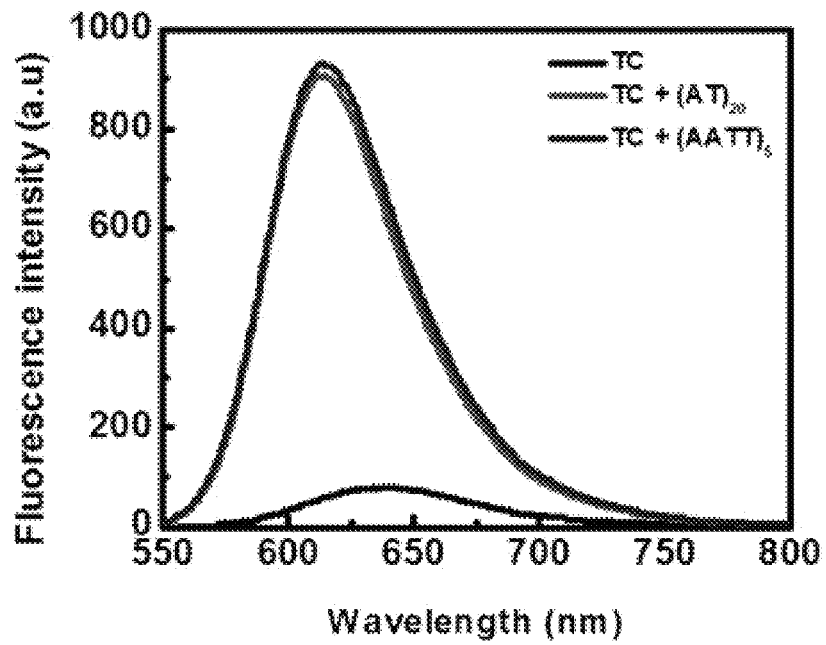

FIG. 28 depicts emission spectra of probe TC in presence of $(AT)_{20}$ and self complementary $d(AATT)_5$ DNA duplexes.

Figure 29:
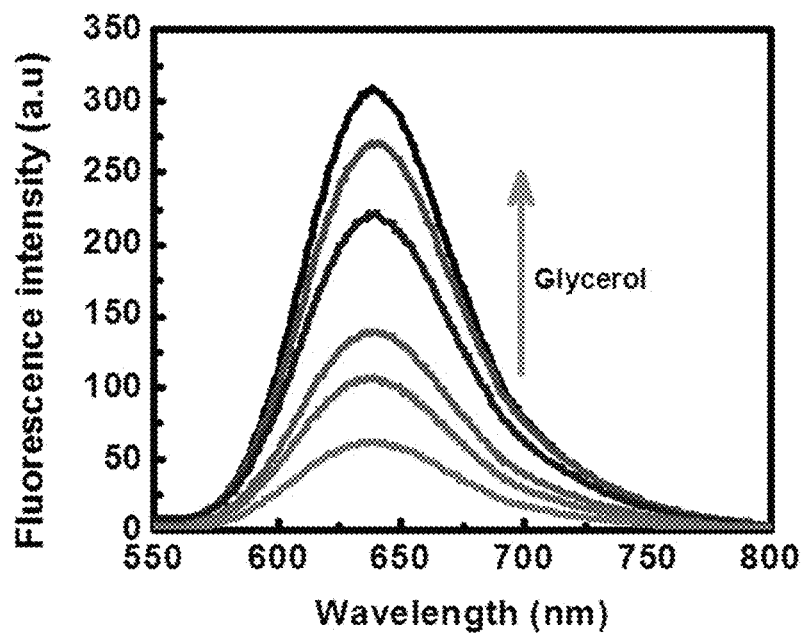

FIG. 29 depicts fluorescence emission spectra of TC (10 µM) in Tris-HCl (100 mM, pH=7.4) buffer solution with increasing glycerol percentage from 0 to 100/%.

Figure 30:
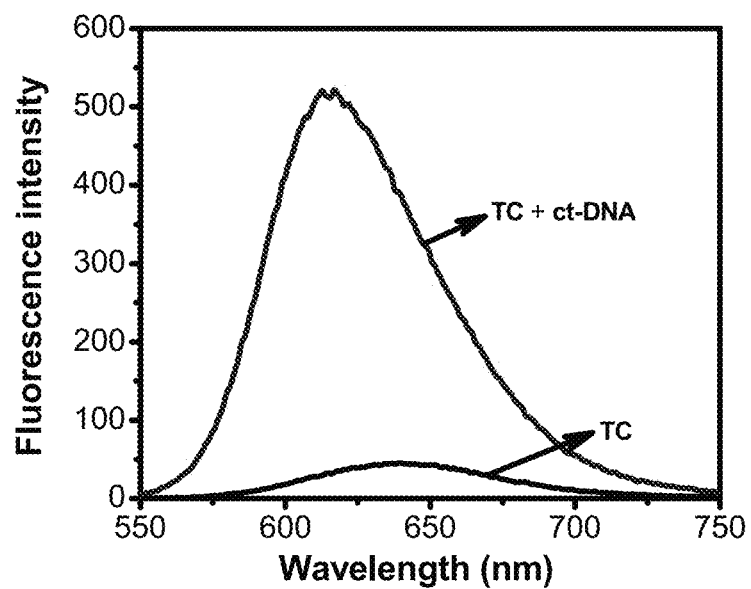

FIG. 30 depicts Fluorescence emission spectra of probe TC (10 µM) in presence of calf-thymus DNA (ct-DNA) (200 µg/mL) upon excitation at 521 nm.

Figure 31:
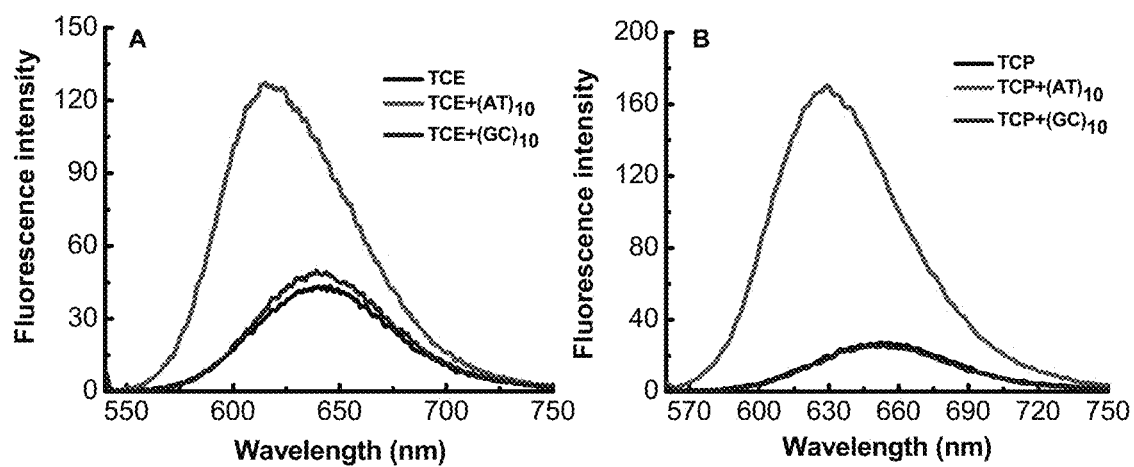

FIG. 31 depicts: Fluorescence spectra of probe TCE and TCP. A) Fluorescence spectra of probe TCE (10 µM) in presence of $(AT)_{10}$ and $(GC)_{10}$, B) Fluorescence spectra of probe TCP (10 µM) in presence of $(AT)_{10}$ and $(GC)_{10}$ in Tris-HCl buffer (100 mM, pH=7.4) solution.

Figure 32:
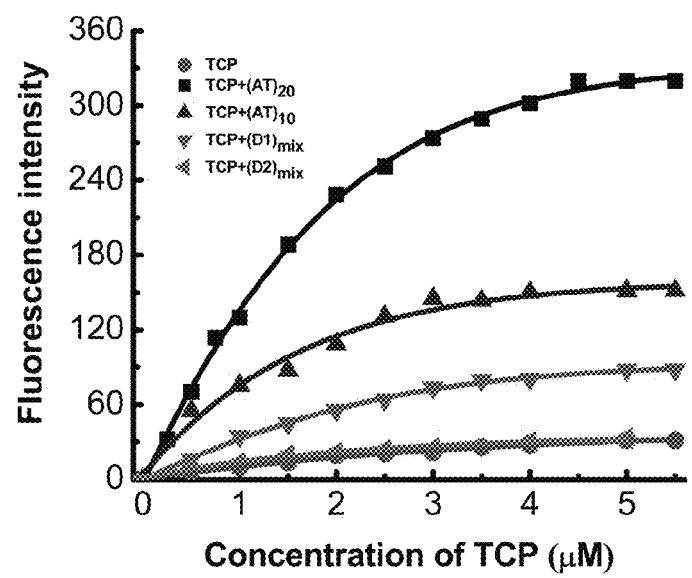

FIG. 32 depicts: Fluorescence response of probe TCP (10 µM) with increasing concentration of $(AT)_{20}$, $(AT)_{10}$, $(GC)_{10}$, $(D1)_{mix}$ and $(D2)_{mix}$ upon excitation at 521 nm.

Figure 33:
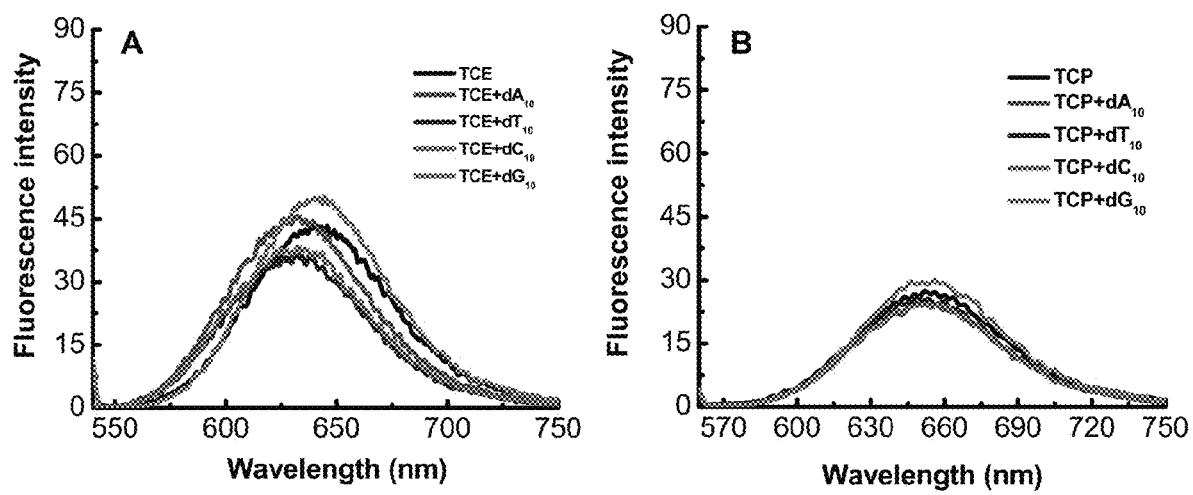

FIG. 33 depicts: A) & B) Fluorescence spectra of probe TCE (10 µM) and TCP (10 µM) in presence of ssDNA's $dA_{10}$, $dT_{10}$, $dC_{10}$ and $dG_{10}$ in Tris-HCl buffer (100 mM, pH=7.4) solution respectively.

Figure 34:
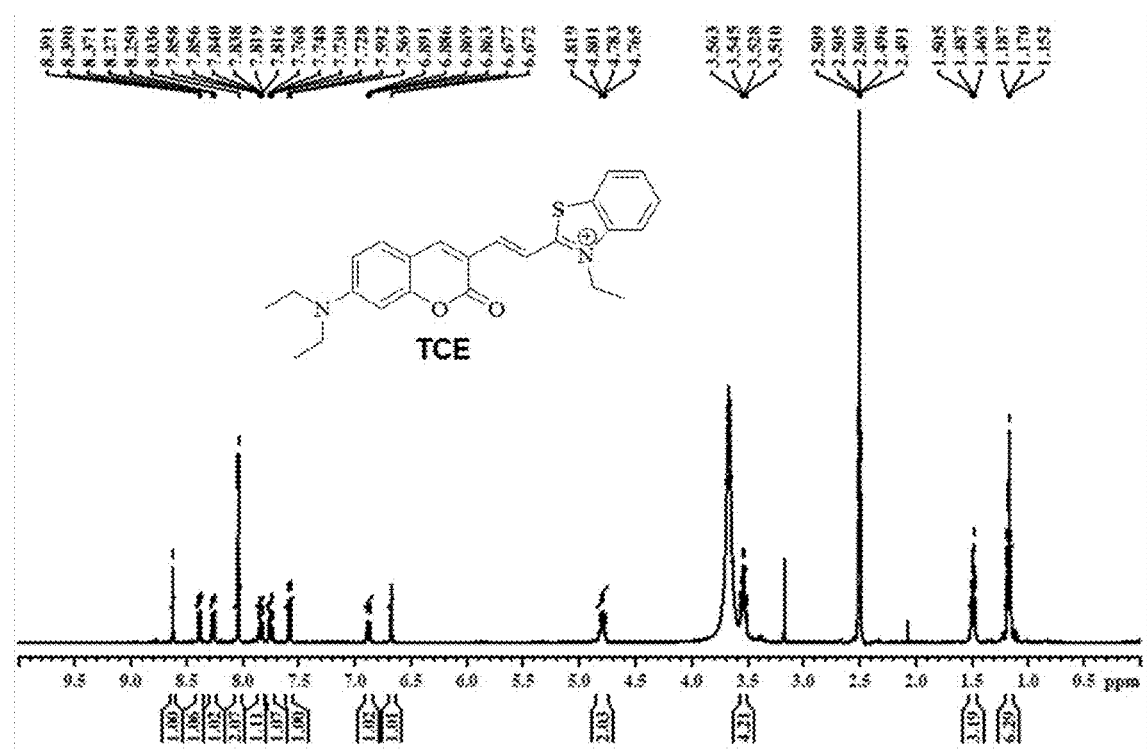
Figure 35:
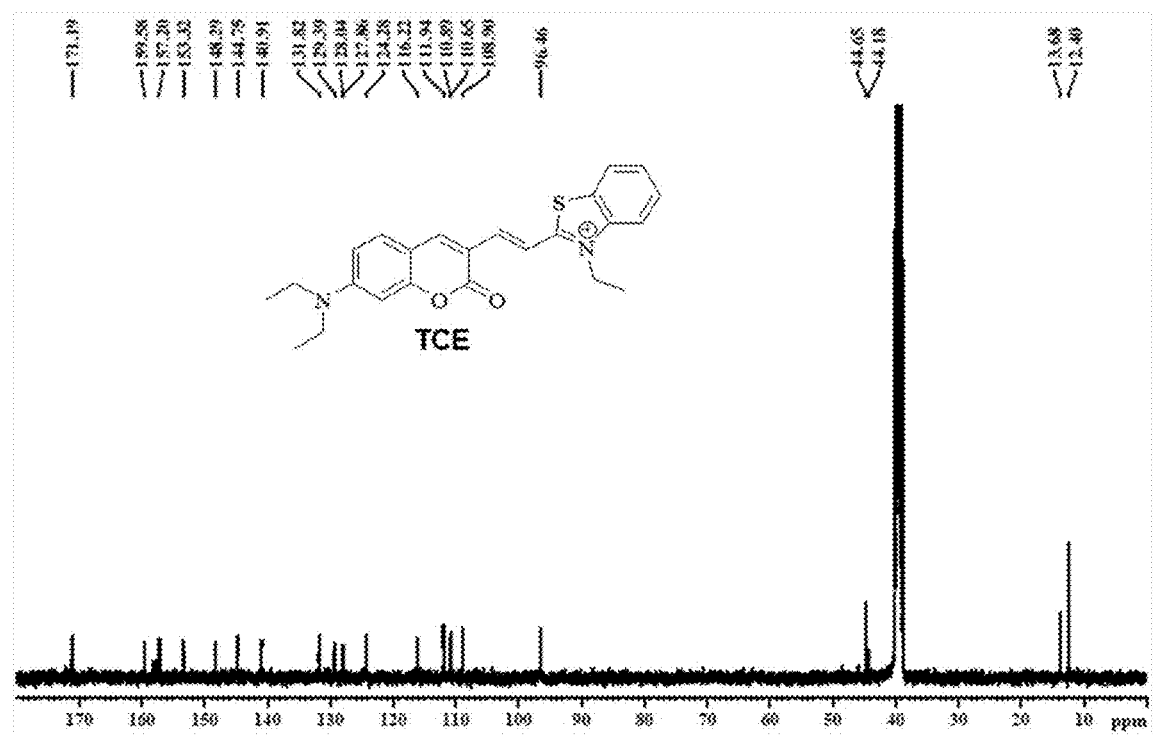

FIGS. 34 and 35 depict: $^1$H and $^{13}$C-NMR spectra of probe TCE.

Figure 36:
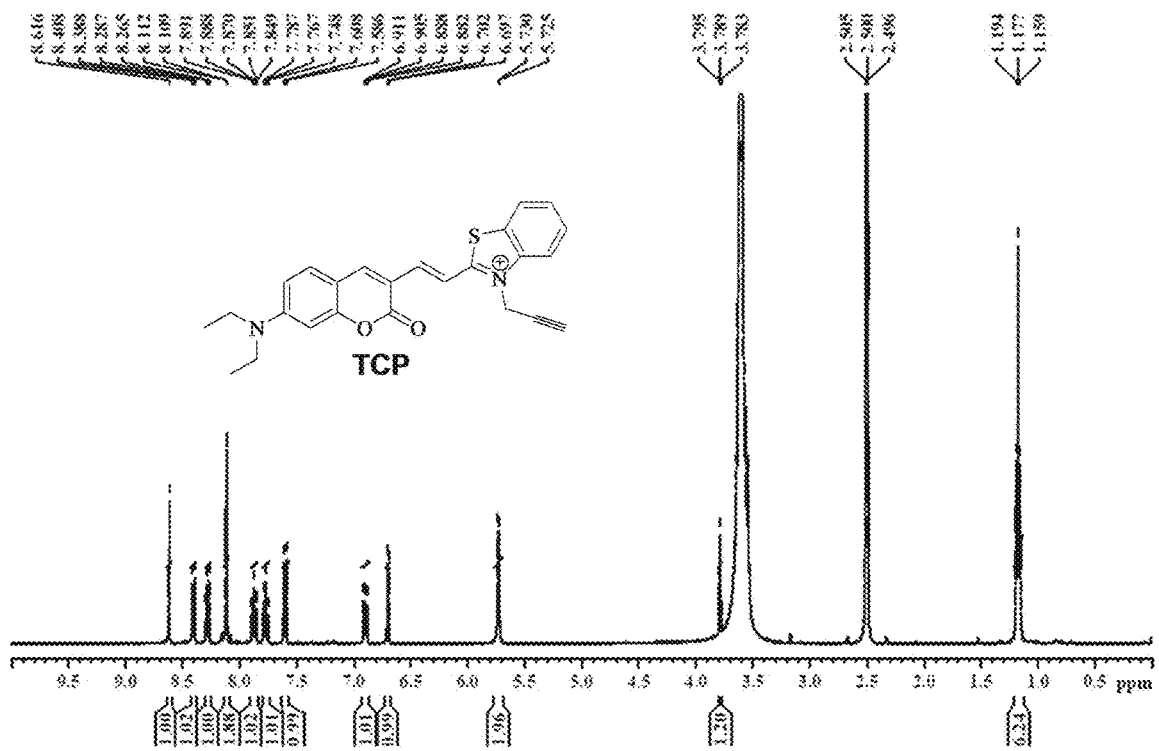
Figure 37:
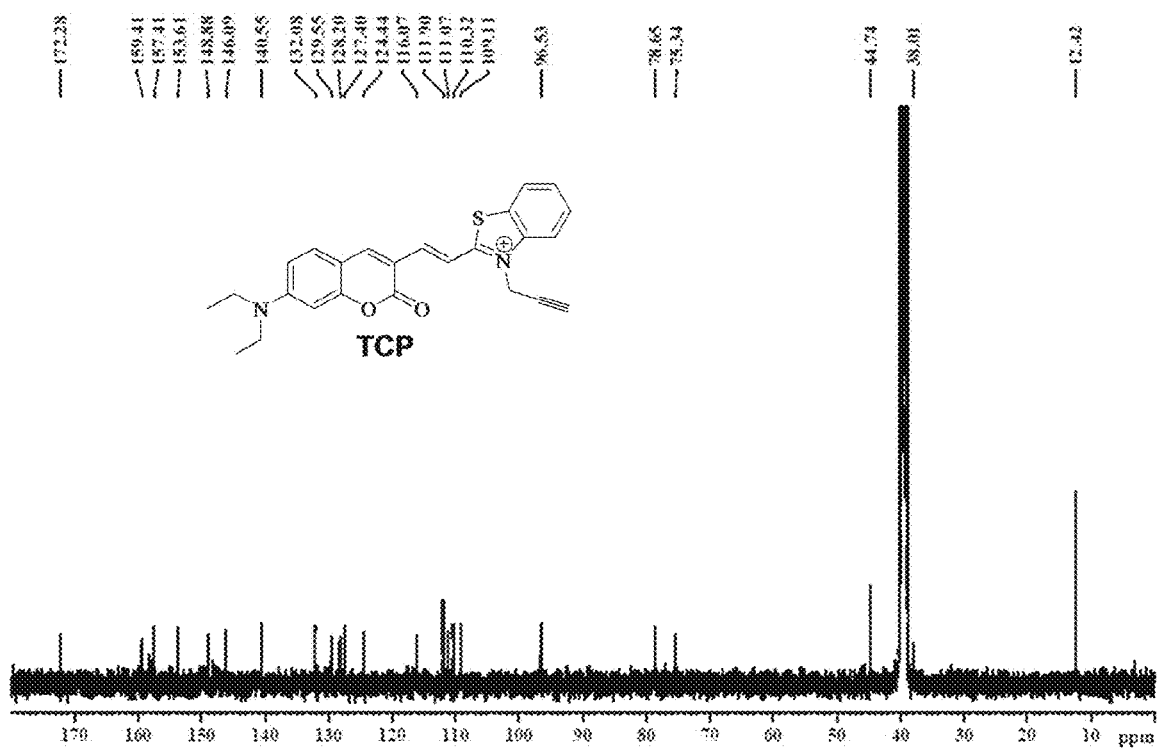

FIGS. 36 and 37 depict: $^1$H and $^{13}$C-NMR spectra of probe TCP.

Figure 38:
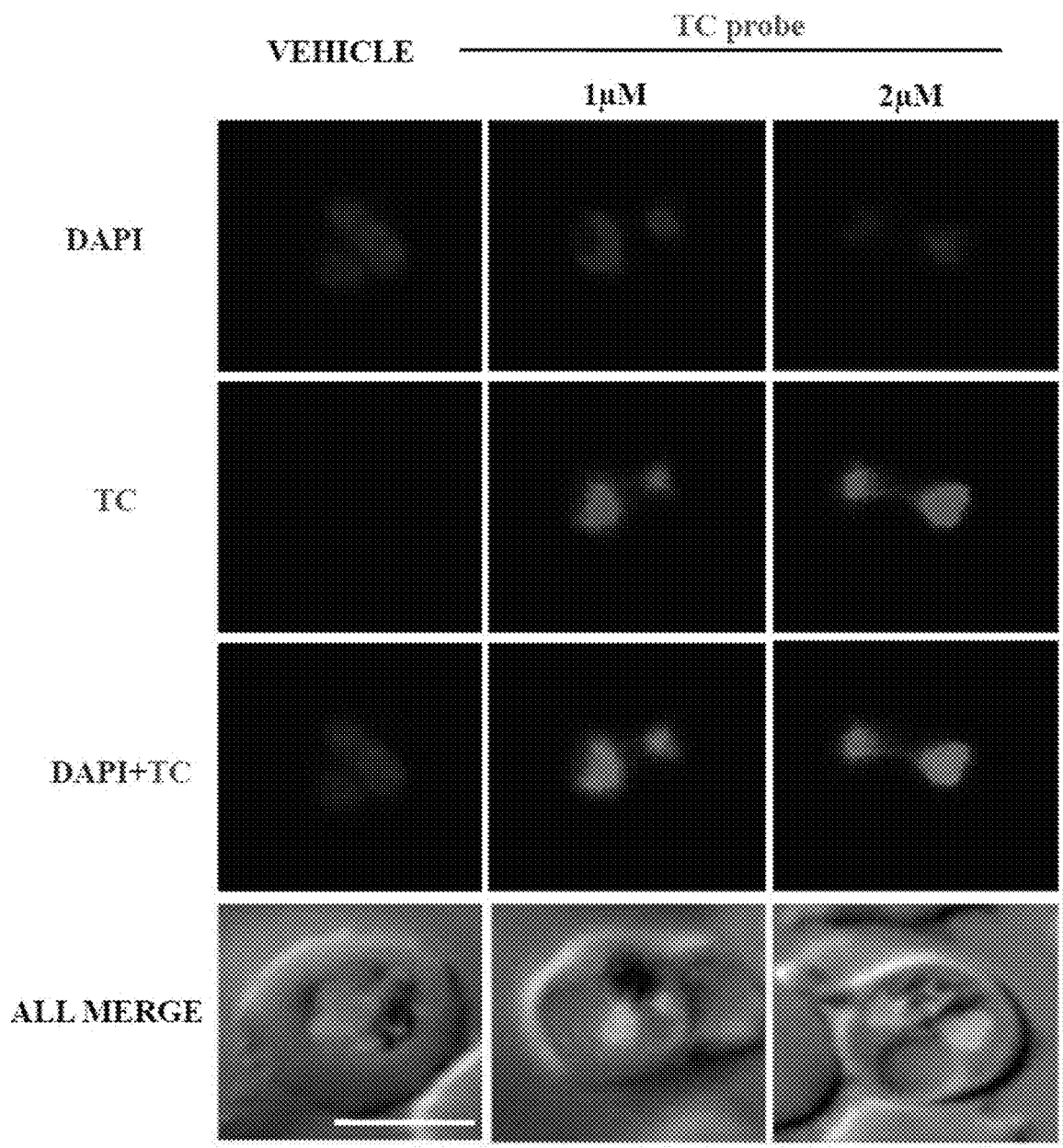

FIG. 38 depicts: Binding of probe TC to the AT rich genome of *Plasmodium falciparum*. Live cell fluorescence imaging showed probe TC is accumulated specifically in the nucleus of the parasitized red blood cell at 1 and 2 µM. Vehicle control (water) did not show any detectable fluorescence under the same experimental conditions. DAPI stains the nuclei and all merged panel shows phase images of the parasites along with DAPI and TC fluorescence signal. Scale bar: 2 µm.

Figure 39:
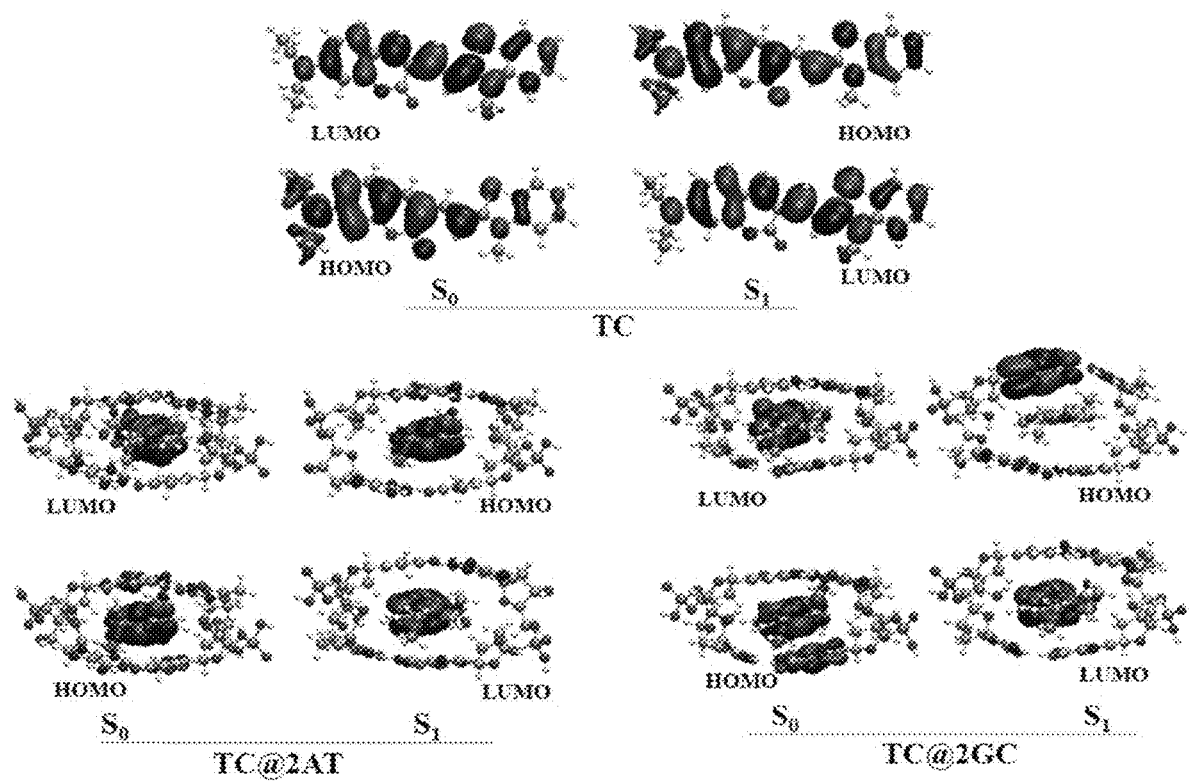
Figure 39:
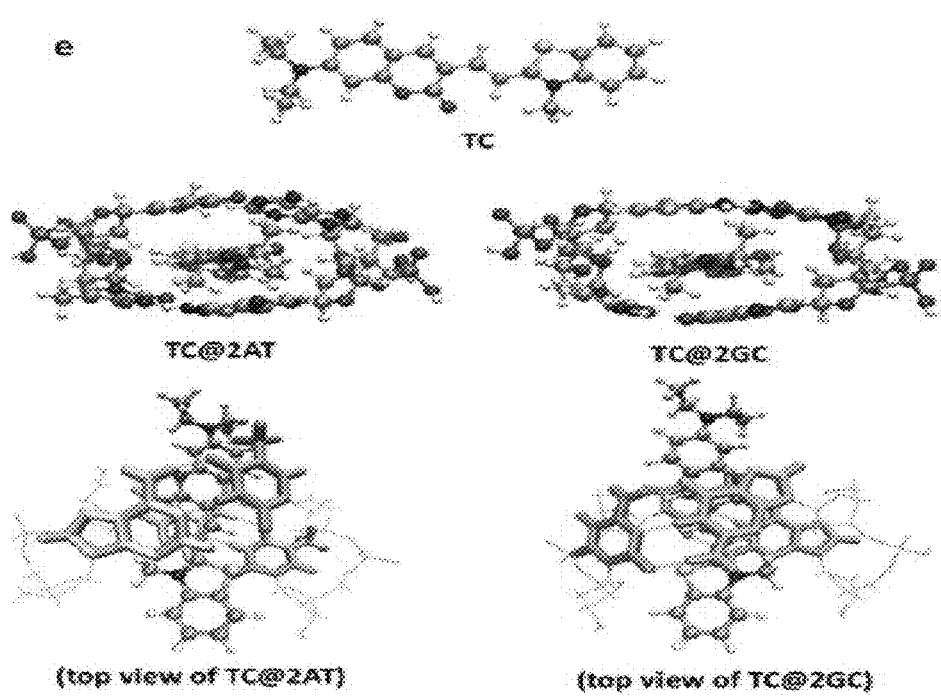

FIG. 39 depicts: The optimized structures of TC showing that intercalation is the most preferred binding mode for TC (FIG. 39B); and the transition occurring from the TC moiety to the guanine moiety of TC@2GC (FIG. 39A).

Figure 40:
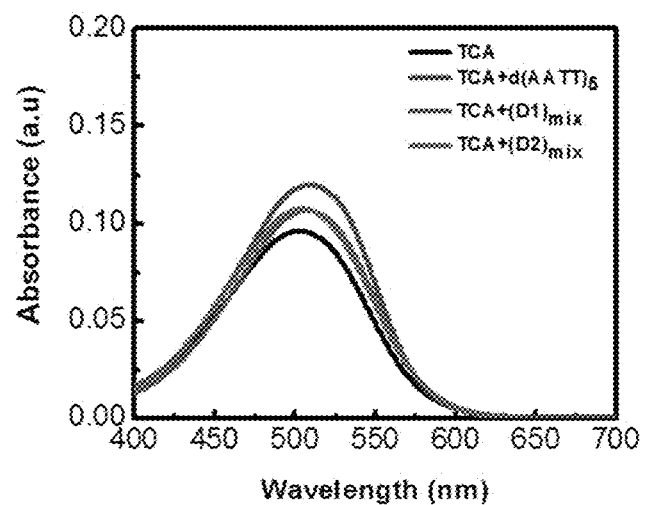

FIG. 40 depicts absorption spectra of probe TCA (10 µM) in presence of $d(AATT)_5$, $(D1)_{mix}$ and $(D2)_{mix}$ in Tris-HCl buffer (100 mM, pH=7.4) solution.

Figure 41:
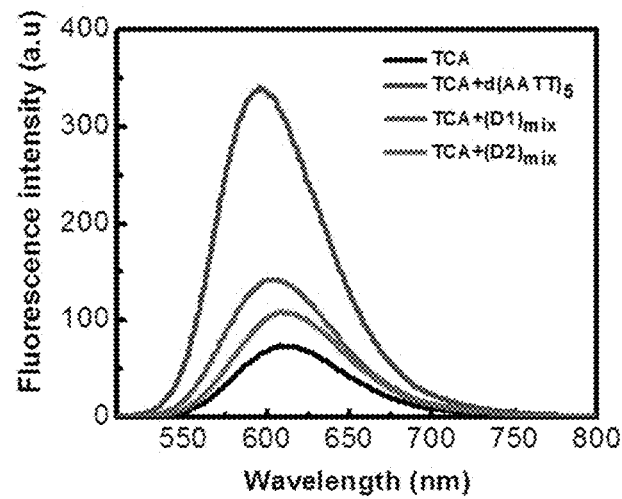

FIG. 41 depicts fluorescence spectra of probe TCA (10 µM) in presence of $d(AATT)_5$, $(D1)_{mix}$ and $(D2)_{mix}$ in Tris-HCl buffer (100 mM, pH=7.4) solution.

Figure 42:
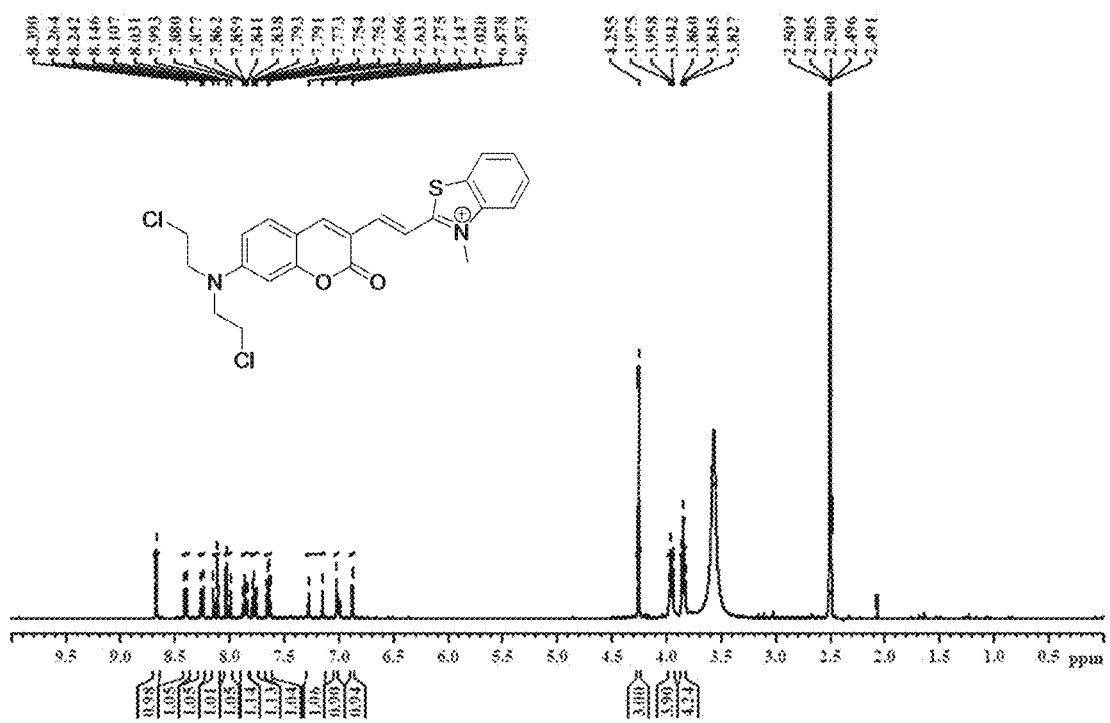
Figure 43:
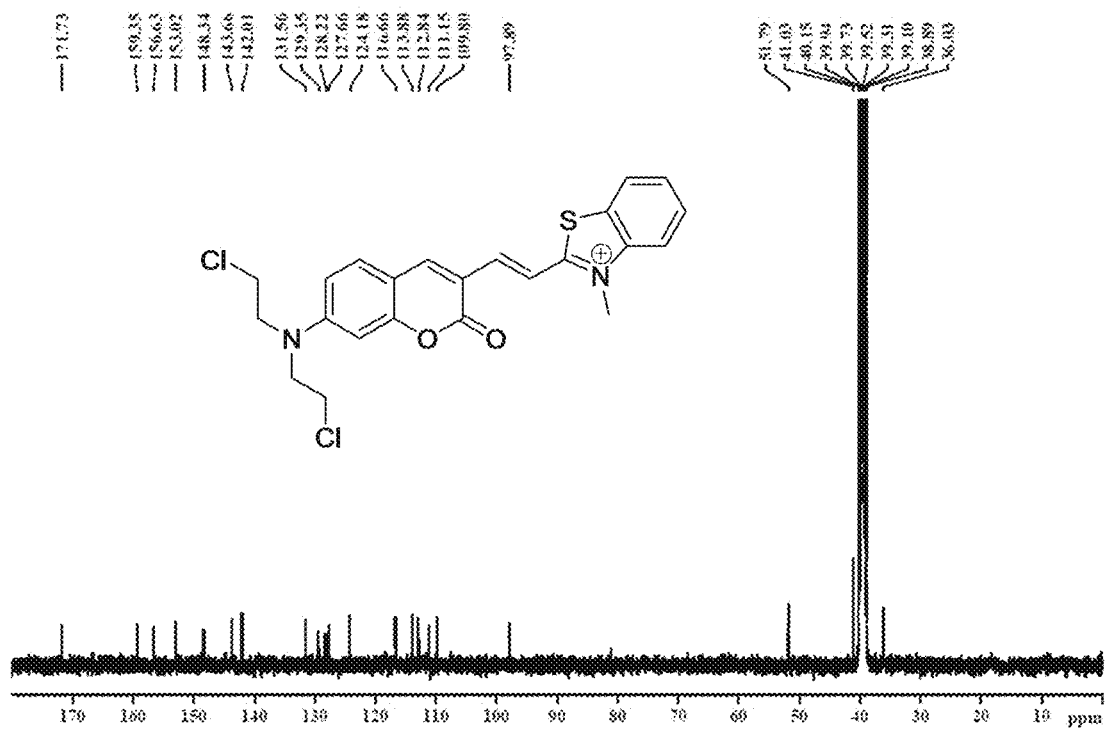
Figure 44:
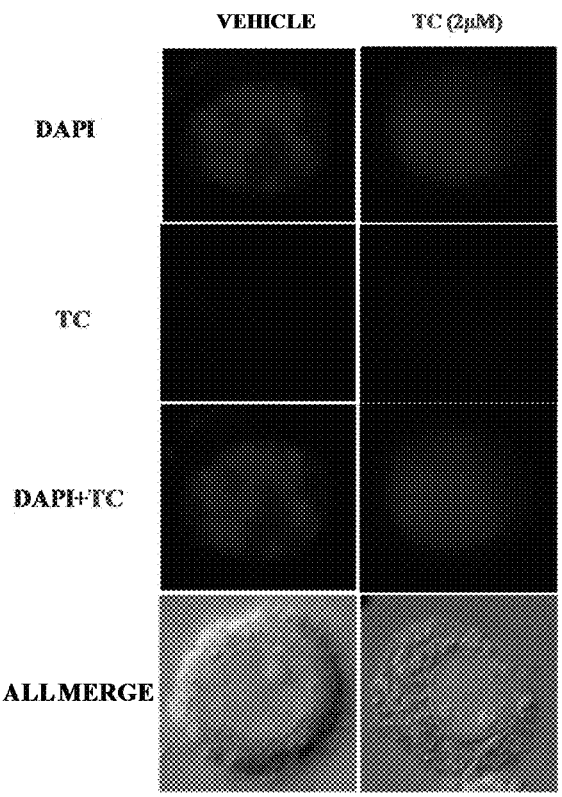

FIG. 42 depicts $^1$H NMR spectra of probe TCA.
FIG. 43 depicts $^{13}$C NMR spectra of probe TCA.
FIG. 44 depicts confocal fluorescence microscope images of mammalian HepG2 (human liver cancer cells) stained with very low concentration of probe TC (2 µM) and DAP1. No detectable uptake of probe TC is observed in HepG2 as seen in *P. falciparum* at the same concentration.

Figure 45:
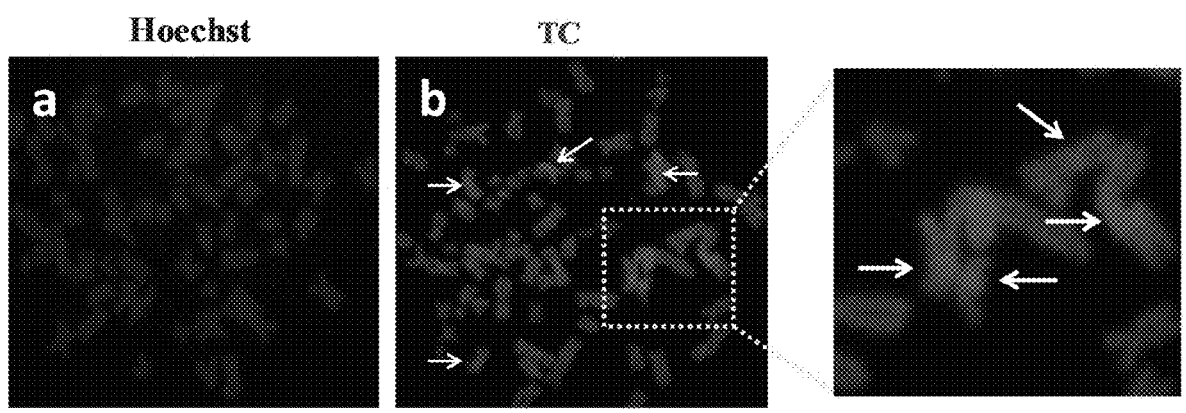

FIG. 45 depicts metaphase chromosomal staining with Hoechst and probe TC. FIG. 45 (A) shows the metaphase chromosomal plate prepared using U87 glioblastoma cell line and stained with Hoechst (10 μg/mL). FIG. 45 (B) probe TC (5 μM). Inset: Arrow shows the maximum centromere localization of probe TC.

Figure 46:
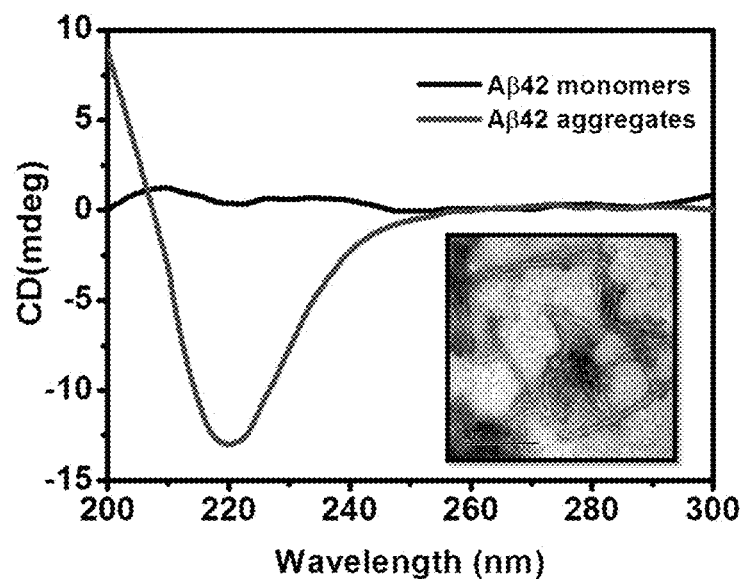

FIG. 46 depicts the CD measurements for Aβ aggregates showing β-sheet conformation when compared to $A\beta_{42}$ monomers (Inset: TEM image for $A\beta_{42}$ fibrillar aggregates).

Figure 47:
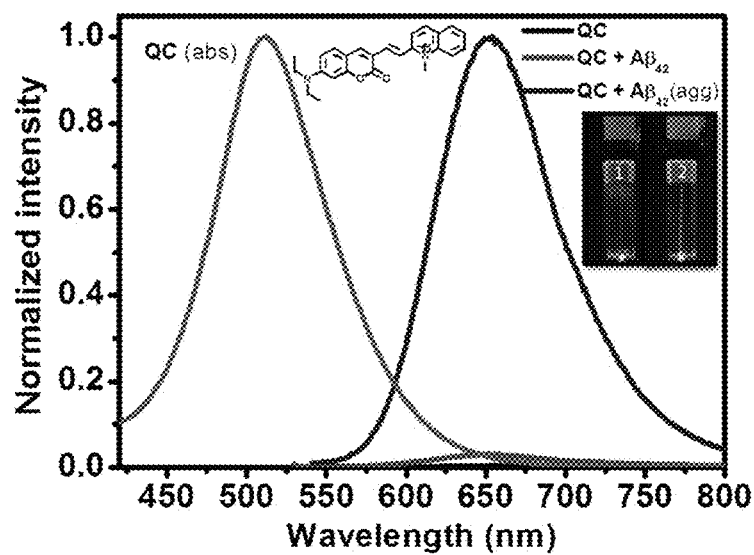

FIG. 47 depicts the normalized plot of absorption and emission ($\lambda_{em}$=521 nm) corresponding to probe QC (2 μM) in presence of Aβ42 monomers (10 μM) and Aβ42 (10 μM) aggregates ($\lambda_{em}$=654 nm) and absence of Aβ42 fibrils (Inset: structure of the molecule). Photographs of QC (1) and QC (2 μM)+Aβ42 (20 μM) (2) fibril samples are illuminated with laser emitting green light which shows a red beam in QC+Aβ42 sample solution.

Figure 48:
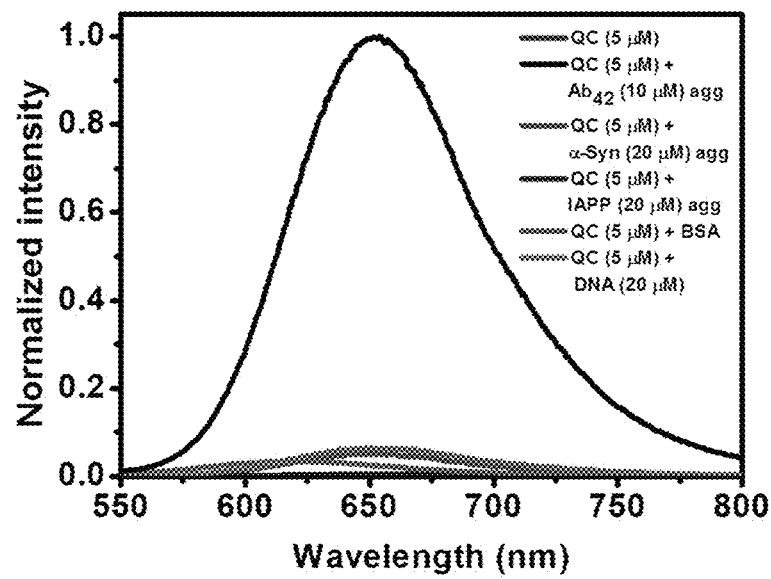

FIG. 48 depicts the Fluorescence intensity of QC upon interaction with Aβ42 fibrils (10 μM), α-Synuclein (α-Syn) peptide and islet amyloid polypeptide (IAPP), BSA and calf-thymus DNA (20 μM).

Figure 49:
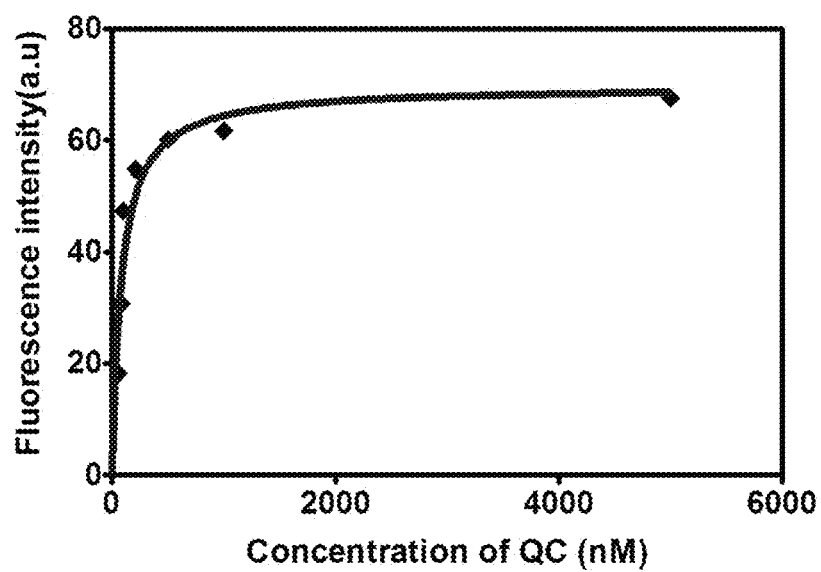

FIG. 49 depicts the plot of the fluorescence intensity as a function of the concentration of QC (0.052, 0.078, 0.210, 0.5, 1 and 5 μM) in the presence of $A\beta_{42}$ (10 μM) fibrils in solutions. Dissociation constants ($K_d$) are obtained as 82±2.3 nM (binding constant (Ka), 12.14±0.43 mM).

Figure 50:
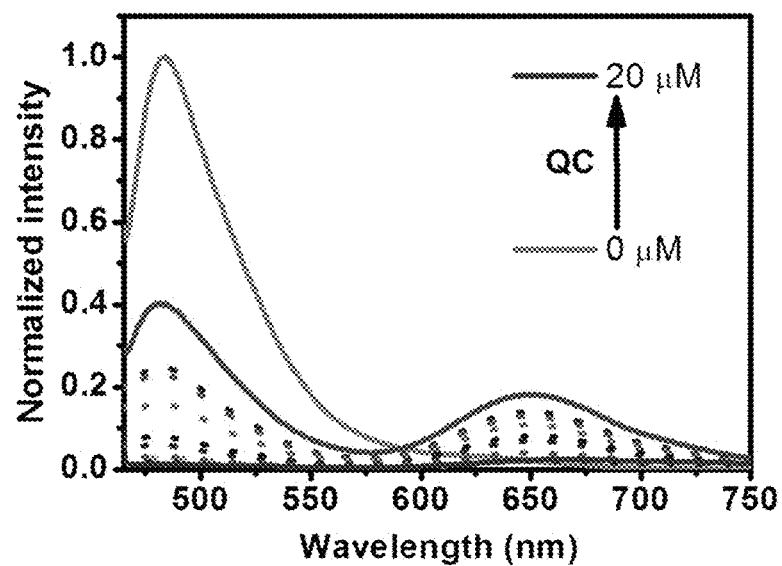

FIG. 50 depicts FRET and displacement assay with QC and ThT. Fluorescence intensities of ThT and QC ($\lambda_{em}$ at 450 nm; fluorescence at 483 nm and ~654 nm) upon titration of a ThT/Aβ42 complex (ThT, 10 μM/Aβ42 fibrils, 20 μM) with QC where the florescence intensities of QC (Arm at 521 nm; fluorescence measured at ~654 nm) upon titration of a ThT/Aβ42 fibrils complex with QC are also depicted.

Figure 51:
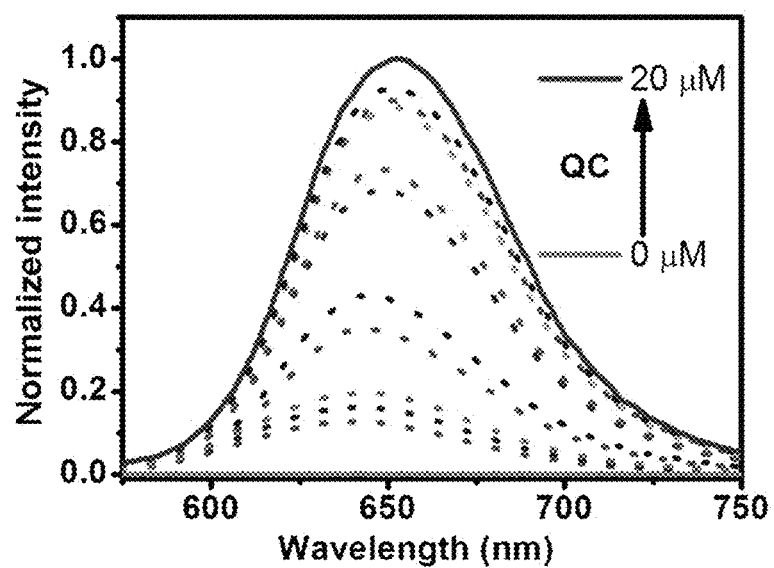

FIG. 51 depicts the FRET and displacement assay with QC and ThT. Florescence intensities of QC ($\lambda_{em}$ at 521 nm; fluorescence measured at ~654 nm) upon titration of a ThT/Aβ42 fibrils complex with QC are depicted.

Figure 52:
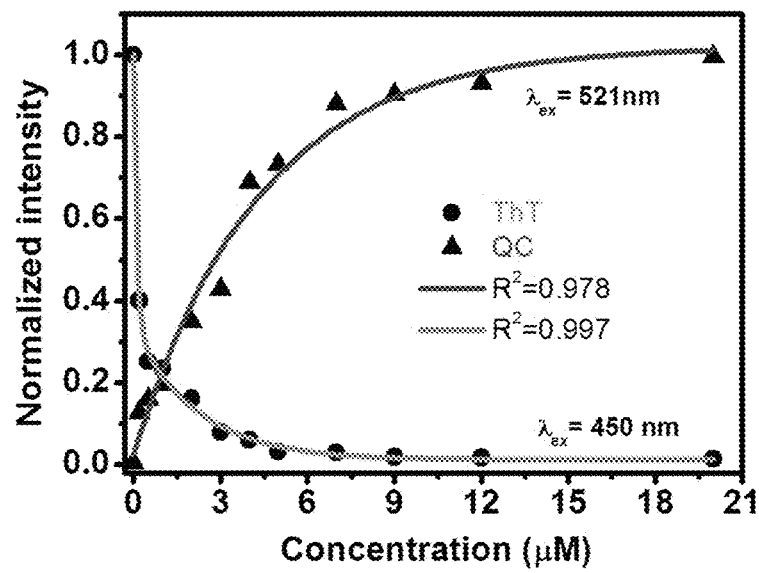

FIG. 52 depicts the FRET and displacement assay with QC and ThT. Dependence of fluorescence intensities of ThT ($\lambda_{em}$ at 450 nm; fluorescence at 483 nm and QC ($\lambda_{em}$ at 521 nm; fluorescence measured at ~654 nm) upon titration of a ThT/Aβ42 fibrils complex (ThT, 10 μM/Aβ42 fibrils, 20 μM) with QC. The dependence of the florescence intensity of QC ($\lambda_{em}$ at 450 nm; fluorescence measured at ~654 nm) upon titration of a ThT/Aβ42 fibrils complex with QC are also depicted.

Figure 53:
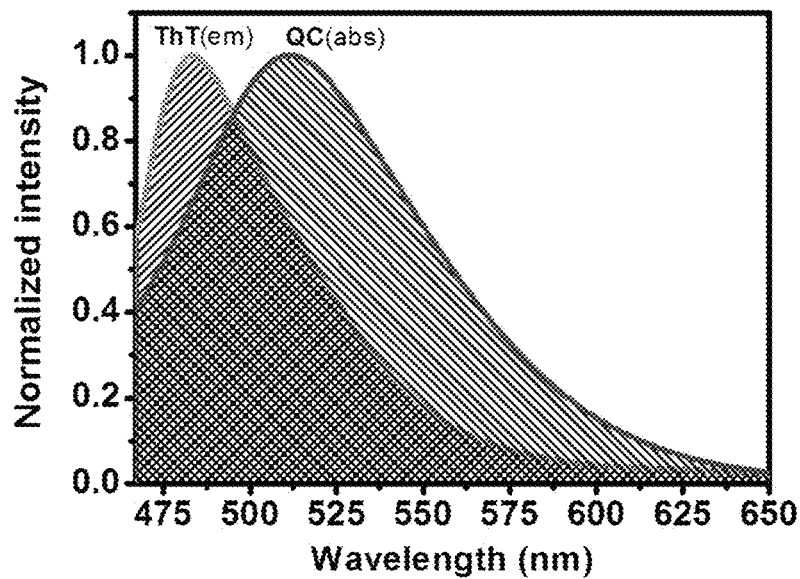

FIG. 53 depicts the spectral overlap for emission from ThT and absorption from QC, showing favorable condition for FRET from ThT to QC.

Figure 54:
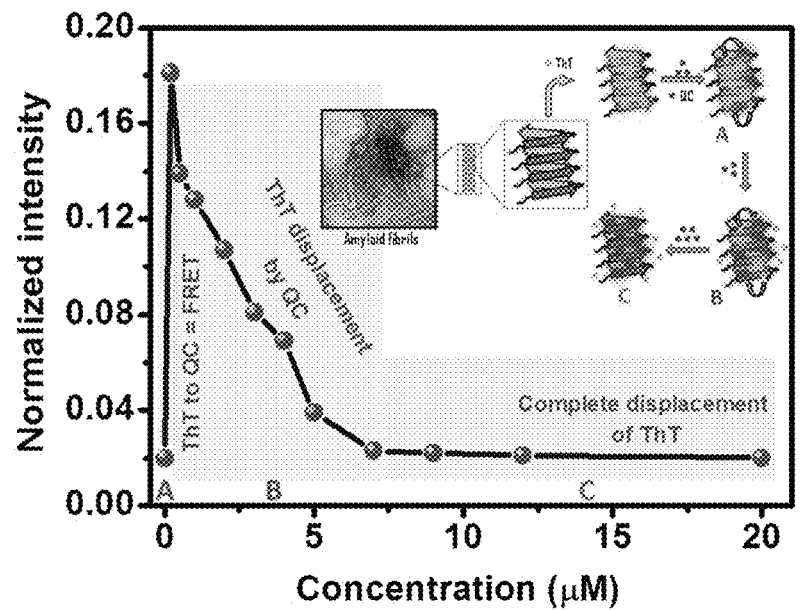

FIG. 54 depicts the FRET and displacement assay with QC and ThT, where the The dependence of the florescence intensity of QC ($\lambda_{em}$ at 450 nm; fluorescence measured at ~654 nm) upon titration of a ThT/Aβ42 fibrils complex with QC. (Inset figure shows proposed model for the FRET and displacement studies of QC towards ThT/Aβ42 fibrils complex).

Figure 55:
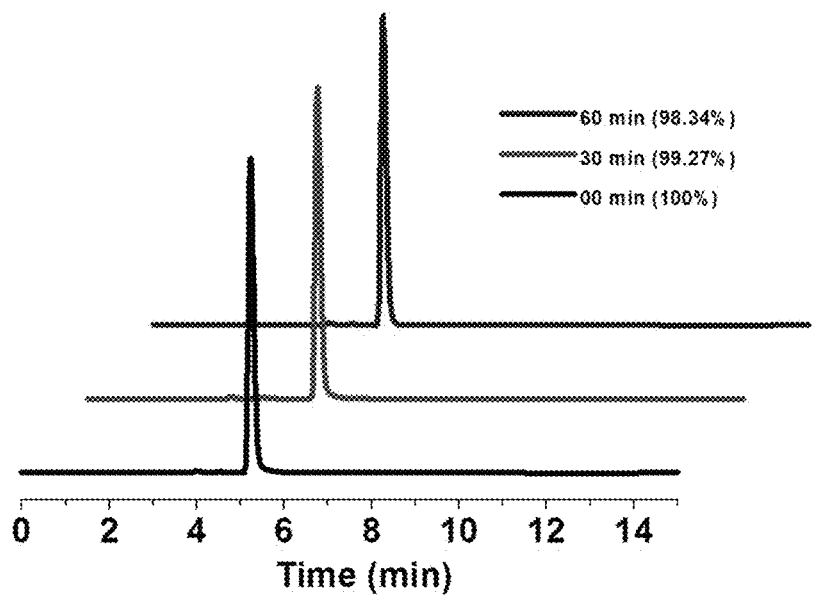

FIG. 55 depicts the in-vitro stability assay of QC. The study shows that QC has high in-vitro stability in human blood serum (HBS) and more than 97% of the probe is identified intact after 60 minutes of incubation with HBS at 37° C.

Figure 56:
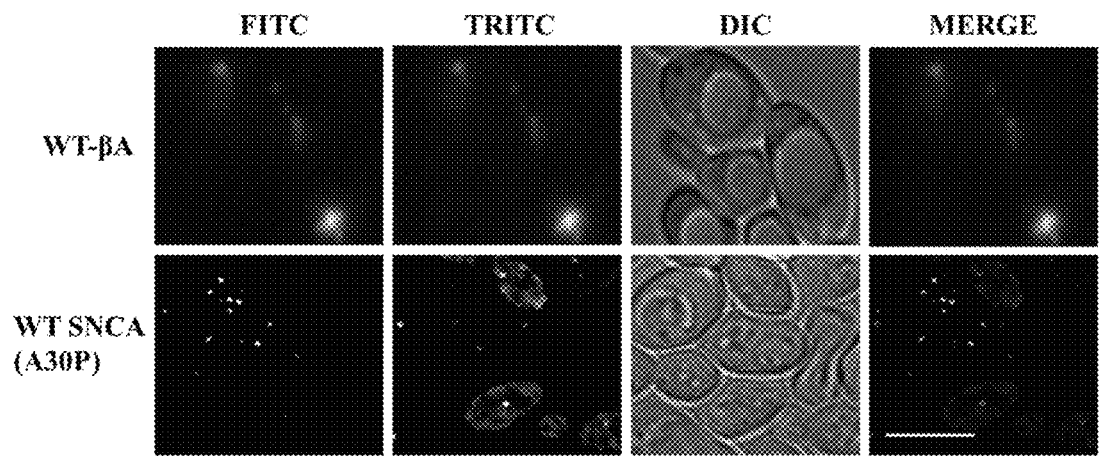

FIG. 56 depicts the β-amyloid and SNCA proteins (A30P) tagged with GFP, imaged in FITC channel whereas QC probe in TRITC. QC (0.1 μM) stains β-amyloid aggregates and not the α-Synuclein aggregates (5 μM).

Figure 57:
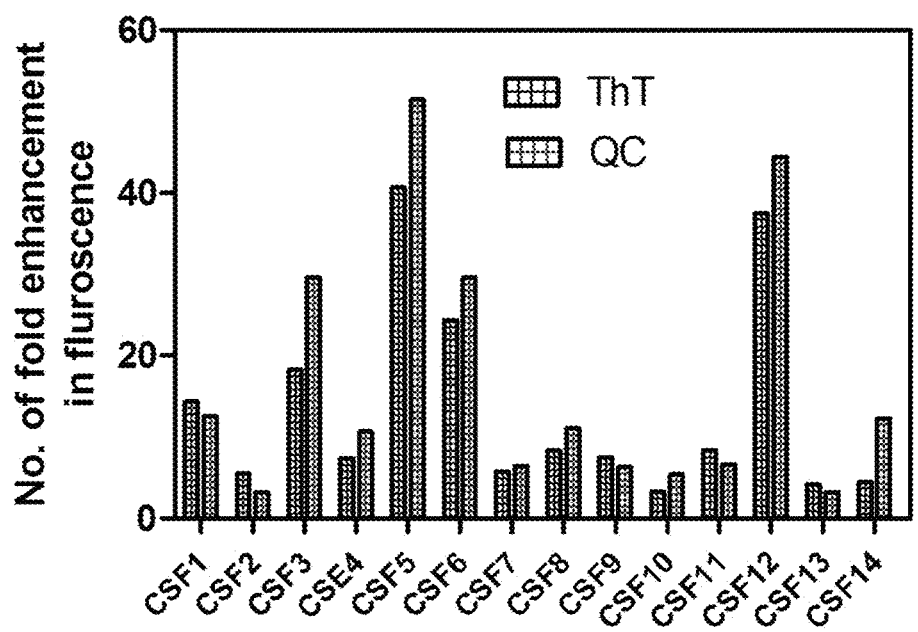

FIG. 57 depicts the CSF samples (300 mL) from different age group screened using ThT (5 mM) and QC (5 mM) to detect Aβ plaques.

Figure 58:
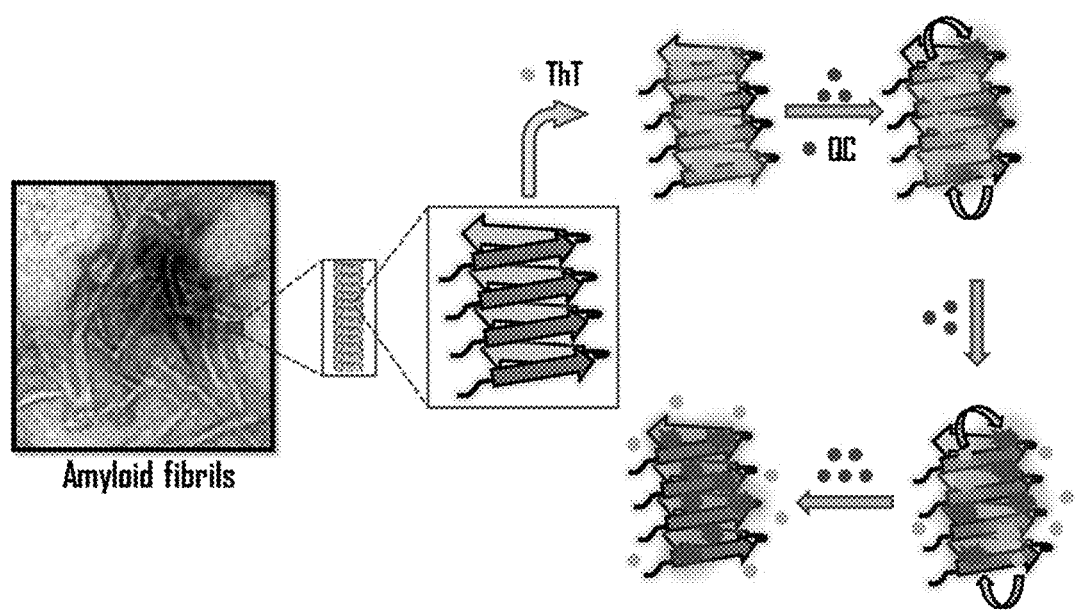

FIG. 58 depicts the proposed model for the FRET and displacement studies of QC towards ThT/Aβ42 fibrils complex.

Figure 59:
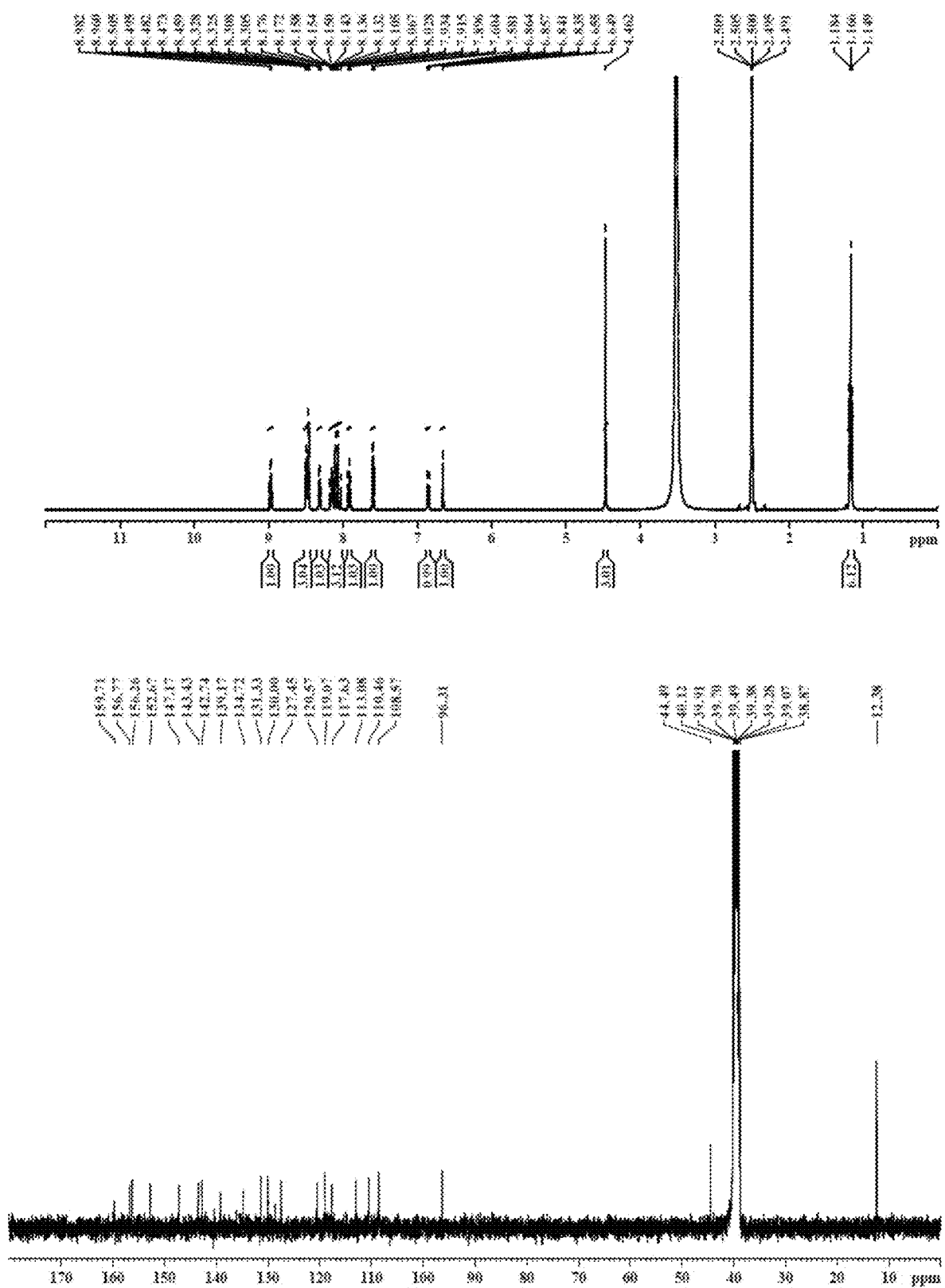

FIG. 59 depicts the NMR spectra of probe QC.

Figure 60:
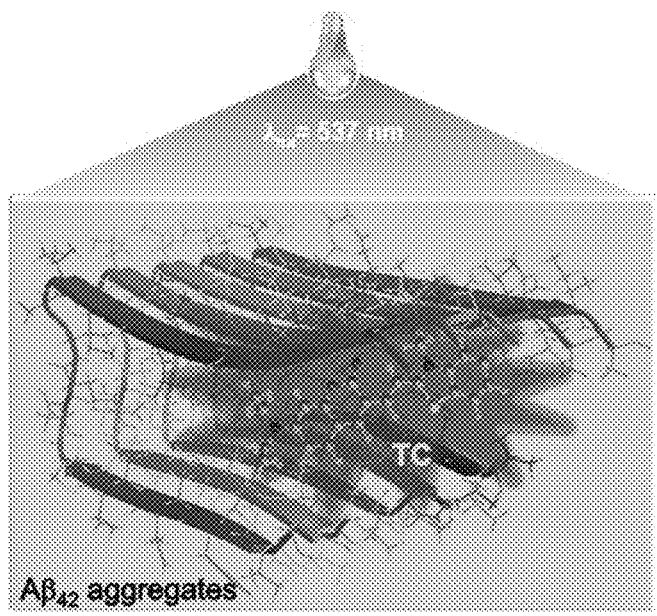

FIG. 60 depicts the structure of the probe TC intercalated with Aβ42 aggregate.

Figure 61:
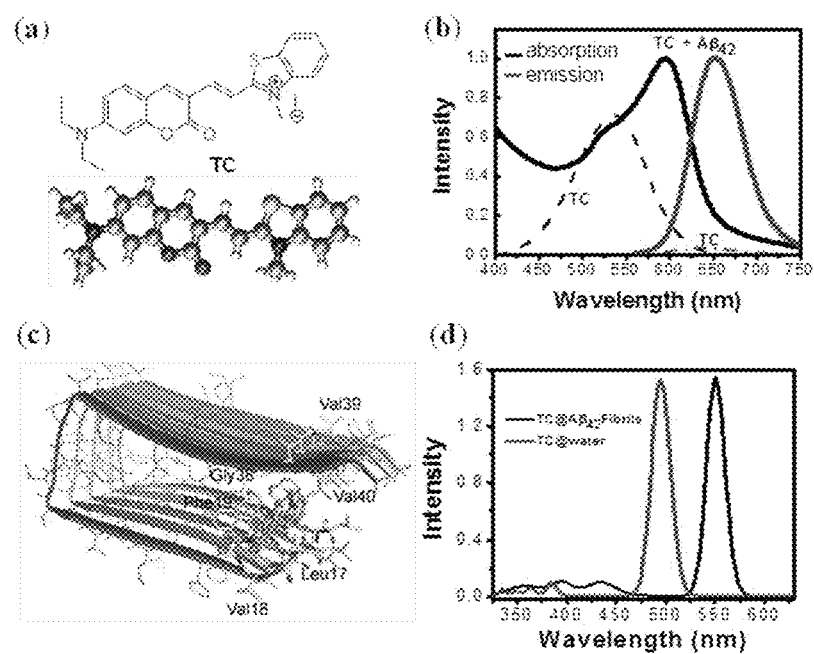

FIG. 61 depicts: the molecular and energy minimized structures of probe TC (FIG. 61(a)). Absorption and emission ($\lambda_{ex}$=537 nm) spectra of probe TC in presence and absence (doted lines) of $A\beta_{42}$ fibrillar aggregates (FIG. 61(b)). The binding mode of TC in the entry site of $A\beta_{42}$ fibril (FIG. 61(c)). The $A\beta_{42}$ fibril is shown in cartoon mode, the binding site residues in stick mode and TC in stick and ball mode (PyMol 1.3). The absorption spectra computed for TC@water and TC@ $A\beta_{42}$ fibril system using TD-DFT/MM models is also depicted (FIG. 61(d)).

Figure 62:
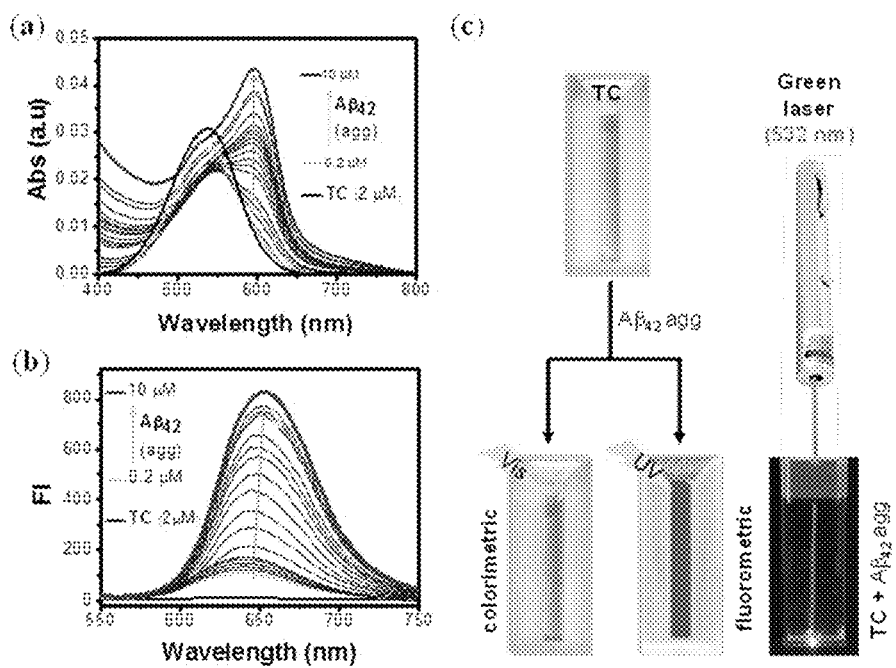

FIG. 62 depicts: Absorption (Abs) spectra of probe TC (2 μM) with increasing concentration of $A\beta_{42}$ fibrillar aggregates (0.2, 0.4, 0.6, 0.8, 1.0, 1.2, 1.4, 1.6, 1.8, 2.0, 2.5, 3.0, 3.5, 4.0, 4.5, 5.0, 6.0, 7.0 and 10.0 μM) as in FIG. 62(a). Emission (FI: fluorescence intensity) spectra ($\lambda_{ex}$=537 nm) of probe TC (2 μM) with increasing concentration of $A\beta_{42}$ fibrillar aggregates (0.2, 0.4, 0.6, 0.8, 1.0, 1.2, 1.4, 1.6, 1.8, 2.0, 2.5, 3.0, 3.5, 4.0, 4.5, 5.0, 6.0, 7.0 and 10.0 μM) is shown in FIG. 62(b). Photographs of TC and TC (2 μM)+ $A\beta_{42}$ fibrillar aggregates (15 μM) samples illuminated under visible and UV light (365 nm) and TC (2 μM)+$A\beta_{42}$ fibrillar (15 μM) illuminated with green laser (532 nm) shows a red beam in the sample solution as in FIG. 62(c).

Figure 63:
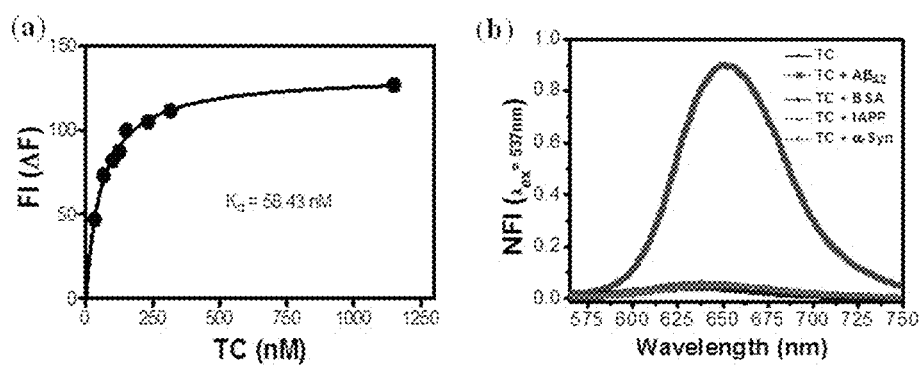

FIG. 63 depicts: The plot of the difference in fluorescence intensity (ΔF) as a function of the concentration of TC in the presence of Aβ42 fibrillar aggregates (2 μM) in solutions (10 mM PBS) in FIG. 63(a). Normalized fluorescence intensity (NFI) of TC upon interaction with aggregates of $A\beta_{42}$ (5 μM), α-synuclein (α-Syn) (20 μM), amylin (IAPP) (20 μM) and hydrophobic protein bovine serum albumin (BSA) are shown in FIG. 63 (b).

Figure 64:
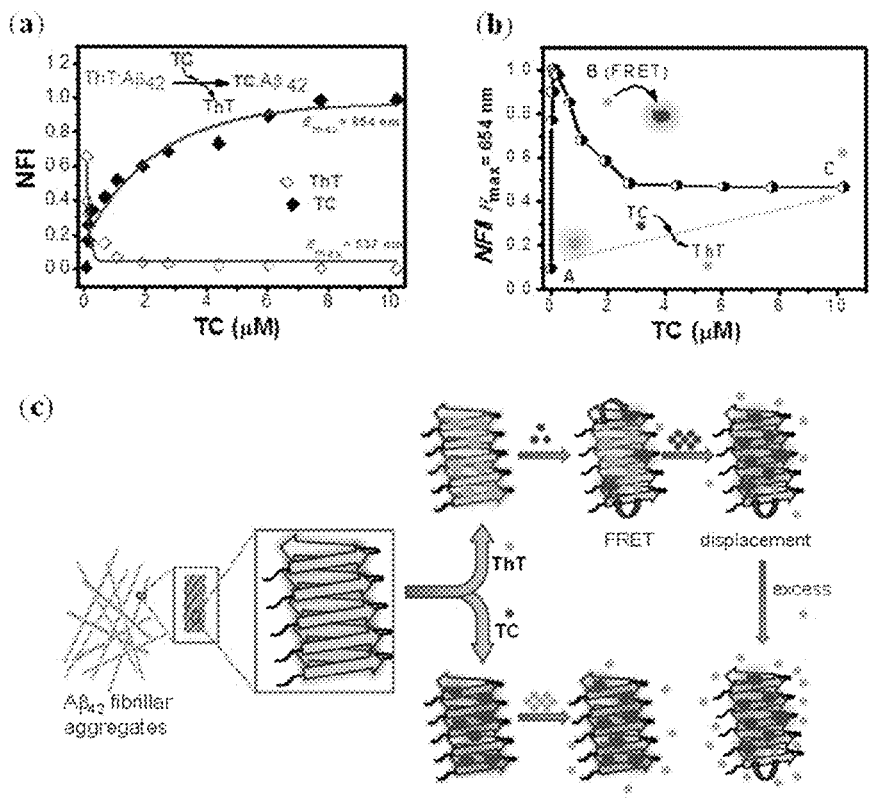

FIG. 64 depicts the Displacement assay wherein the FIG. 64(a) depicts the titration of TC to ThT/$A\beta_{42}$ fibrillar aggregate complex (ThT, 5 μM/$A\beta_{42}$ fibrils, 10 μM) in 10 mM PBS buffer solution. High affinity TC effectively displaces ThT from the ThT/$A\beta_{42}$ fibrillar aggregate complex, as monitored by the decrease in fluorescence emission at 483 nm (◇ green trace, $\lambda_{ex}$=450 nm) and corresponding increase in fluorescence emission at 654 nm (♦ red trace, $\lambda_{ex}$=537 nm). FIG. 64(b) shows the emission of TC monitored at 654 nm ($E_{max}$) upon excitation at 450 nm ($\lambda_{ex}$ of ThT). Region A: ThT/$A\beta_{42}$ fibrillar aggregate complex. Region B: TC/ThT/$A\beta_{42}$ fibrillar aggregate complex, at low concentration TC coexists with ThT leading FRET between them. Region C: TC displaces ThT, with residual ThT (possibly in the inner cleft of the $A\beta_{42}$ fibril) which leads to residual FRET. FIG. 64(c) depicts the proposed model for the TC displacement of ThT and FRET between them on the $A\beta_{42}$ fibrils. NFI: Normalized fluorescence intensity.

Figure 65:
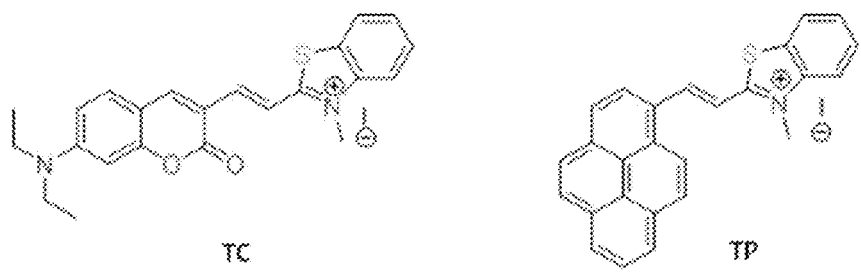

FIG. 65 depicts the molecular structures of probes TC and TP with their corresponding absorption and emission maxima in presence and absence Aβ42 aggregates, and other properties.

Figure 66:
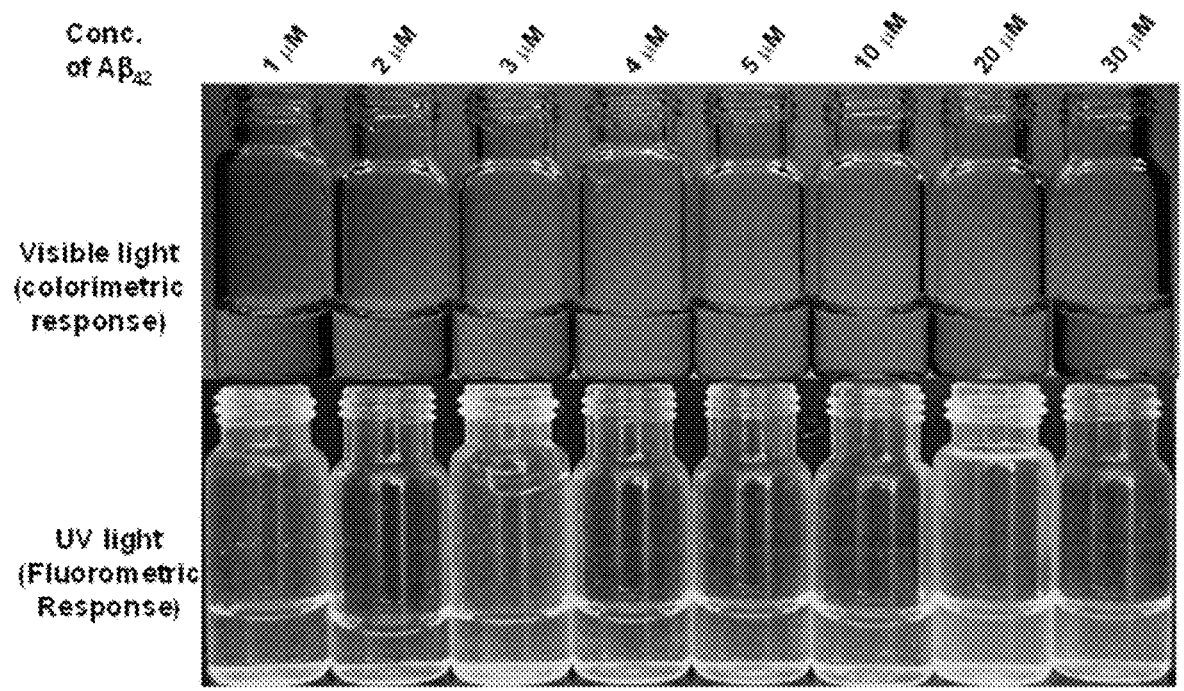

FIG. 66 depicts the photograph of TC (2 μM) exhibiting colorimetric and fluorometric changes with increasing concentration of Aβ42 aggregates.

Figure 67:
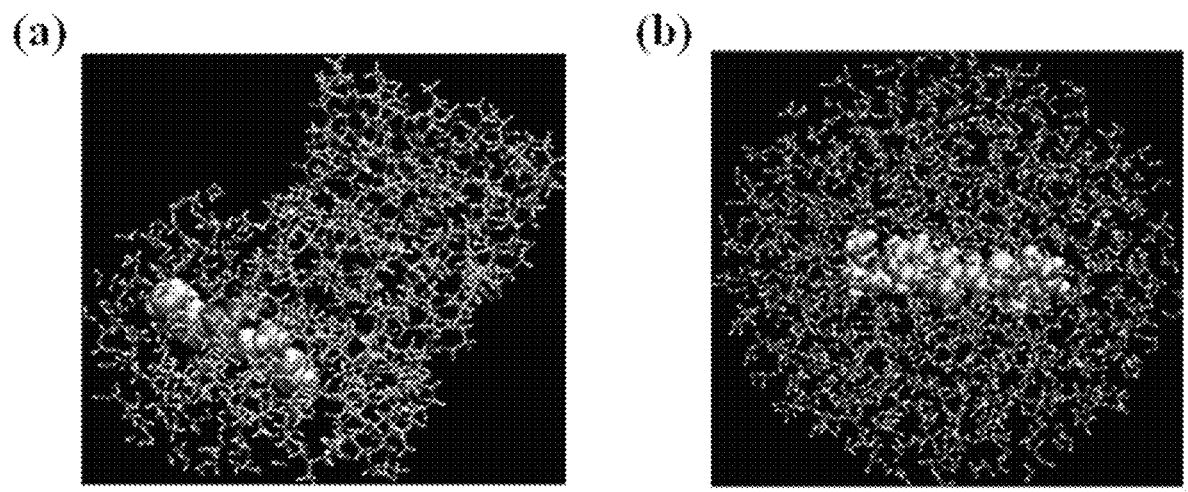

FIG. 67 depicts the representative snapshot configurations used in TD-DFT/MM calculation wherein FIG. 67(a)

depicts TC in Aβ$_{42}$ fibrils and FIG. 67(b) depicts TC in water. In both cases TC is described using density functional theory (DFT) using B3LYP functional and TZVP basis set. The environments namely Aβ$_{42}$ fibrils in water and water solvents are described using molecular mechanics force-fields.

Figure 68:
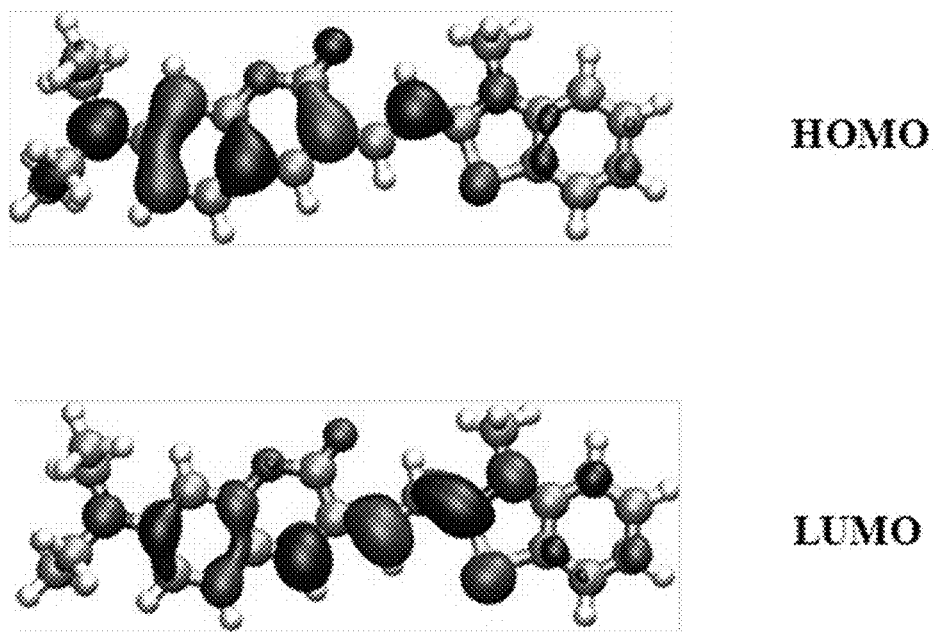

FIG. 68 depicts the HOMO and LUMO molecular orbitals of TC involved in the lowest energy excitation.

Figure 69:
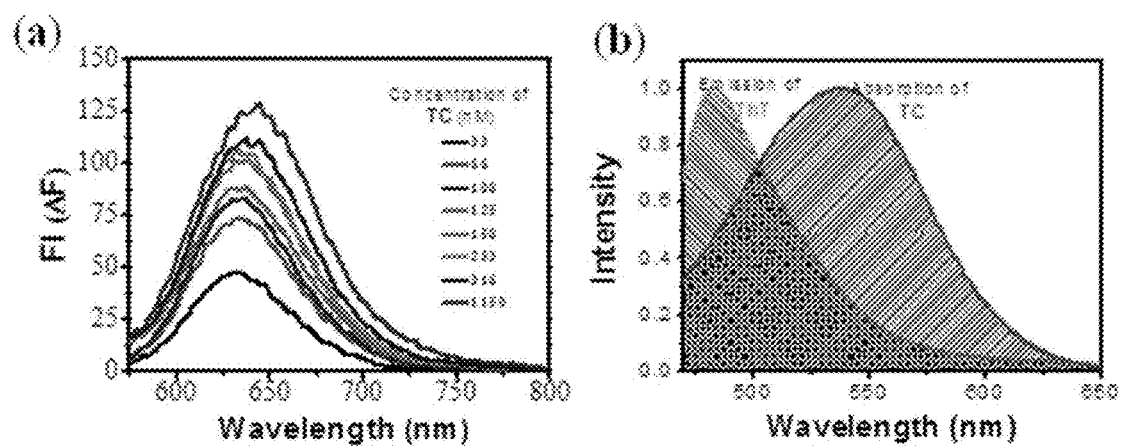

FIG. 69 depicts the difference fluorescence emission spectra of TC in PBS buffer and TC bound to Aβ42 aggregates (FIG. 69(a)). Excitation wavelength: $\lambda_{ex}$=537 nm. Fluorescence intensity (FI) data is used for calculation of binding constant. Spectral overlap for emission from ThT and absorption of TC, showing favourable condition for FRET from ThT to TC (FIG. 69(b)).

Figure 70:
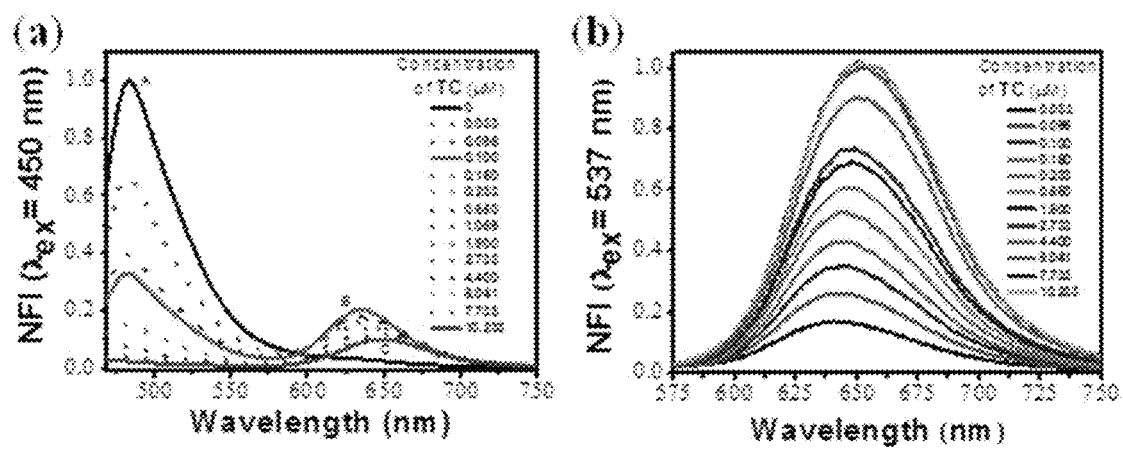

FIG. 70 depicts the FRET and displacement assay with TC and ThT. Normalized fluorescence intensities (NFI) of ThT and TC ($\lambda_{ex}$ at 450 nm; fluorescence at 483 nm and ~654 nm) upon titration of a ThT/Aβ42 aggregate complex (ThT, 5 μM/Aβ$_{42}$ aggregates, 10 μM) with TC are shown in FIG. 70(a). Normalized fluorescence intensities (NFI) of TC ($\lambda_{ex}$ at 537 nm; fluorescence measured at ~654 nm) upon titration of a ThT/Aβ42 aggregate complex with TC are shown in FIG. 70(b).

Figure 71:
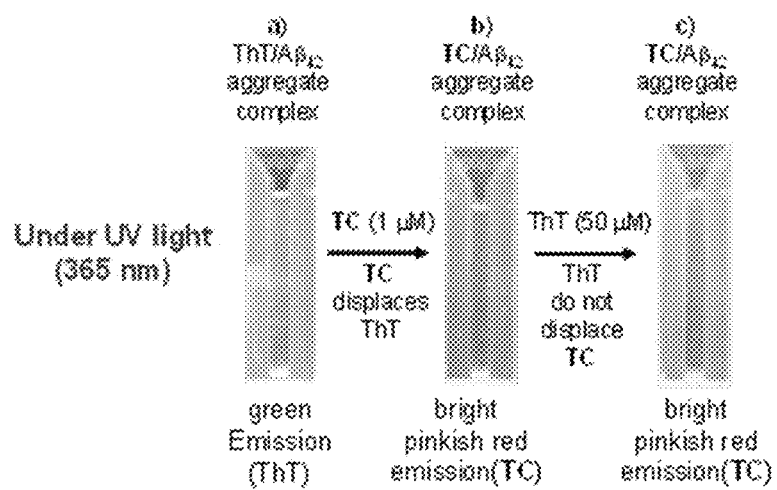

FIG. 71 depicts the photographs of ThT (10 μM)/Aβ42 aggregates complex (FIG. 71(a)), after adding TC (ThT displacement) and further addition of excess ThT in FIG. 71(b) and FIG. 71(c) respectively, illuminated under UV light (365 nm).

Figure 72:
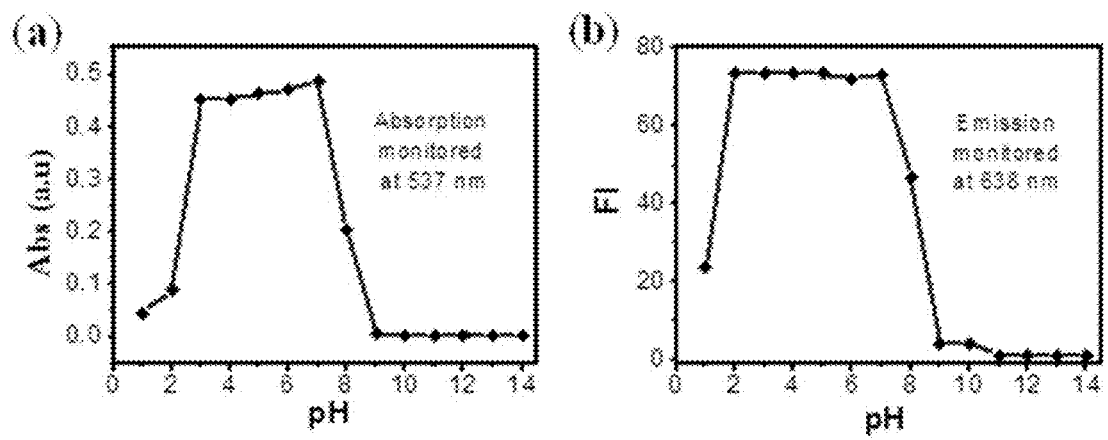

FIG. 72 depicts the colorimetric (absorbance at 537 nm) in FIG. 72(a) and fluorometric (emission at 639 nm) response of TC (10 μM) in presence of Aβ42 aggregates, monitored at different pH in PBS buffer in FIG. 72(b). Probe TC can be effectively used as a colorimetric and fluorometric probe for Aβ42 aggregates in the wide pH range of 2-8. Abs: Absorbance, FI: Fluorescence intensity.

Figure 73:
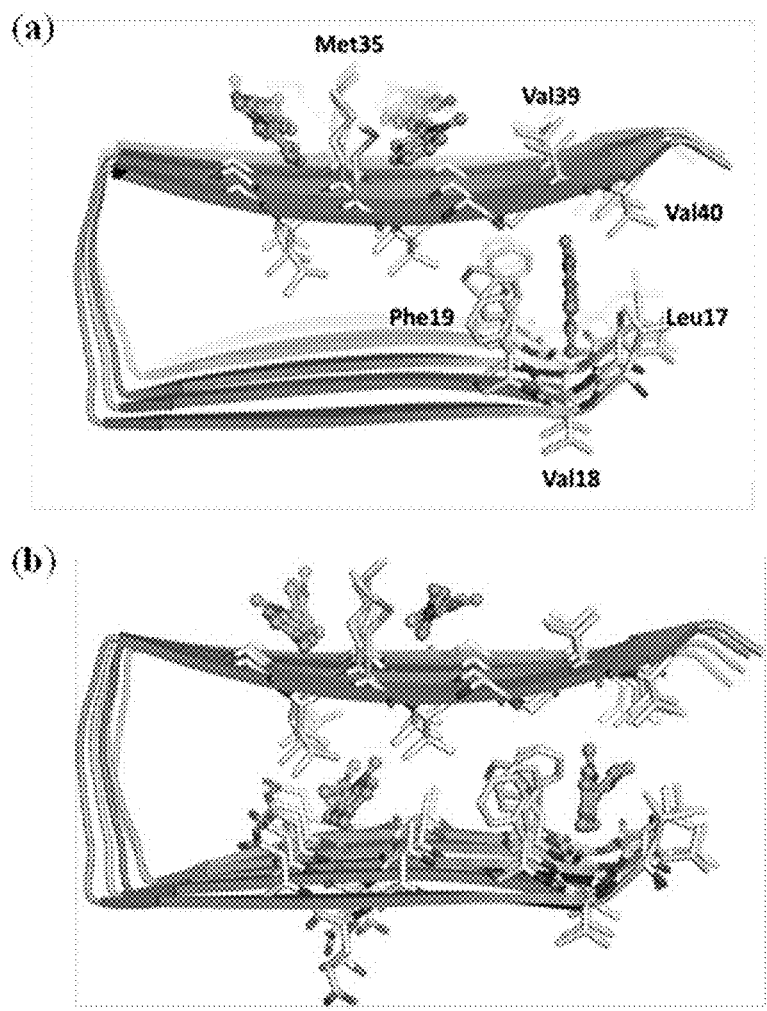

FIG. 73 depicts the docking results of TC as shown in FIG. 73(a) and ThT as shown in FIG. 73(b) with Aβ42 fibril (all binding sites are shown). The fibril is shown in cartoon mode, the binding site residues in stick mode and TC or ThT in stick and ball mode (This picture is rendered by PyMol 1.3 graphic system).

Figure 74:
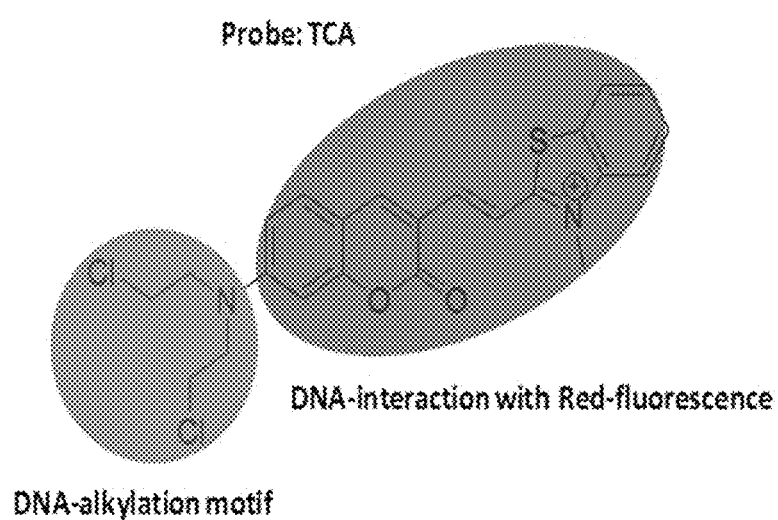

FIG. 74 depicts the interaction of probe TCA with DNA.

DETAILED DESCRIPTION OF THE DISCLOSURE

The present disclosure relates to a Compound of Formula I:

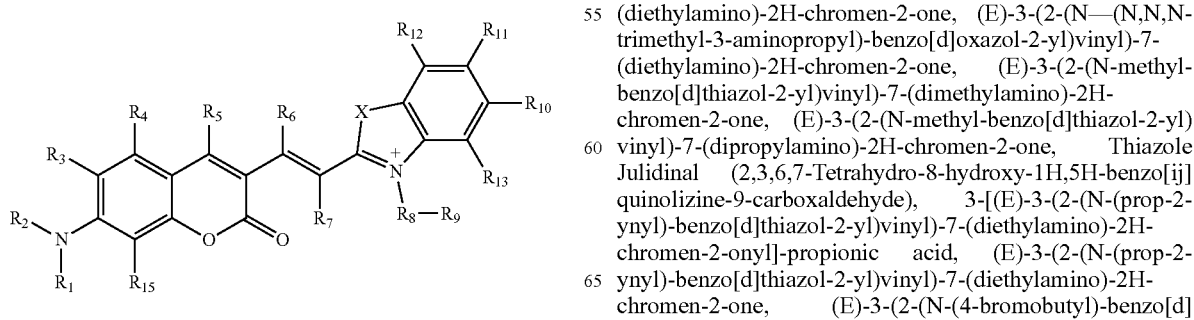

Wherein,
X is selected from group comprising Nitrogen, Oxygen, Sulphur, Se, —NH— and dimethylmethelene;
R1 and R2 are selected from group comprising H, alkyl chain (C1-C5) and substituted alkyl;
R3, R4 and R5 are selected from group comprising H, OH, halogen, alkyl or substituted alkyl; wherein, halogen is selected from a group comprising bromide, chloride and iodide;
R6 and R7 are selected from group comprising H, alkyl, aryl, nitrile/cyano, acid and halogen; wherein halogen is selected from a group comprising, Chloride, Fluoride, Bromide and Iodide; and wherein acid is carboxylic acid.
R8 is selected from group comprising H and —(CH$_2$)$_n$—, wherein 'n' is 1-6.
R9 is selected from group comprising hydrogen, aryl, halogen, methyl, amines, terminal alkynes, alkenes, alkyl acids, amine acids, —OH and sulfonates (SO$_3^-$).
R10, R11, R12 and R13 are selected from group comprising H, OH, Alkyl, aryl, halogen, Nitro, sulfonates (SO$_3^-$) and nitrile/cyano group.
R15 is selected from group comprising but not limiting to H, OH, halogen, alkyl or alkyl substituted with halogen or hydroxyl groups; wherein, halogen is selected from a group comprising bromide, chloride and iodide; Alkyl is selected from a group comprising methyl, ethyl, propyl and butyl; Alkyl substituted with halogen or hydroxyl groups is selected from group comprising CH2X and CH2OH, wherein X is either bromide, chloride or iodide.
Wherein, optionally R2 and R3, R1 and R15 form a cyclic structure;

In an embodiment of the present disclosure, the compound is selected from group comprising, (E)-3-(2-(N-methyl-benzo[d]thiazol-2-yl)vinyl)-7-(diethylamino)-2H-chromen-2-one, (E)-3-(2-(N-methyl-benzo[d]oxazol-2-yl)vinyl)-7-(diethylamino)-2H-chromen-2-one, (E)-3-(2-(N-methyl-benzo[d][1,3]selenazol-2-yl)vinyl)-7-(diethylamino)-2H-chromen-2-one, (E)-3-(2-(N-ethyl-benzo[d]thiazol-2-yl)vinyl)-7-(diethylamino)-2H-chromen-2-one, (E)-3-(2-(N-(prop-2-ynyl)-benzo[d]thiazol-2-yl)vinyl)-7-(diethylamino)-2H-chromen-2-one, (E)-3-(2-(N—(N,N,N-trimethyl-2-aminoethyl)-benzo[d]thiazol-2-yl)vinyl)-7-(diethylamino)-2H-chromen-2-one, (E)-3-(2-(N-(2-aminium ethyl)-benzo[d]thiazol-2-yl)vinyl)-7-(diethylamino)-2H-chromen-2-one, (E)-3-(2-(N—(N,N,N-trimethyl-3-aminopropyl)-benzo[d]thiazol-2-yl)vinyl)-7-(diethylamino)-2H-chromen-2-one, (E)-3-(2-(N-ethyl-benzo[d]oxazol-2-yl)vinyl)-7-(diethylamino)-2H-chromen-2-one, (E)-3-(2-(N-(prop-2-ynyl)-benzo[d]oxazol-2-yl)vinyl)-7-(diethylamino)-2H-chromen-2-one, (E)-3-(2-(N—(N,N,N-trimethyl-2-aminoethyl)-benzo[d]oxazol-2-yl)vinyl)-7-(diethylamino)-2H-chromen-2-one, (E)-3-(2-(N-(2-aminium ethyl)-benzo[d]oxazol-2-yl)vinyl)-7-(diethylamino)-2H-chromen-2-one, (E)-3-(2-(N—(N,N,N-trimethyl-3-aminopropyl)-benzo[d]oxazol-2-yl)vinyl)-7-(diethylamino)-2H-chromen-2-one, (E)-3-(2-(N-methyl-benzo[d]thiazol-2-yl)vinyl)-7-(dimethylamino)-2H-chromen-2-one, (E)-3-(2-(N-methyl-benzo[d]thiazol-2-yl)vinyl)-7-(dipropylamino)-2H-chromen-2-one, Thiazole Julidinal (2,3,6,7-Tetrahydro-8-hydroxy-1H,5H-benzo[ij]quinolizine-9-carboxaldehyde), 3-[(E)-3-(2-(N-(prop-2-ynyl)-benzo[d]thiazol-2-yl)vinyl)-7-(diethylamino)-2H-chromen-2-onyl]-propionic acid, (E)-3-(2-(N-(prop-2-ynyl)-benzo[d]thiazol-2-yl)vinyl)-7-(diethylamino)-2H-chromen-2-one, (E)-3-(2-(N-(4-bromobutyl)-benzo[d]thiazol-2-yl)vinyl)-7-(diethylamino)-2H-chromen-2-one and (E)-3-(N-Methyl2-(benzo[d]thiazol-2-yl)vinyl)-7(bis(2-chloroethyl)amino)-2H-chromen-2-one.

In another embodiment of the present disclosure, the compound exists in monomeric or dimeric form.

The present disclosure relates to a compound of Formula V having the structural formula:

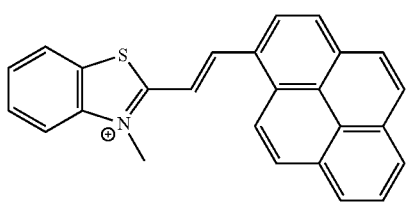

V

The present disclosure relates to a compound of Formula VI having the structural formula:

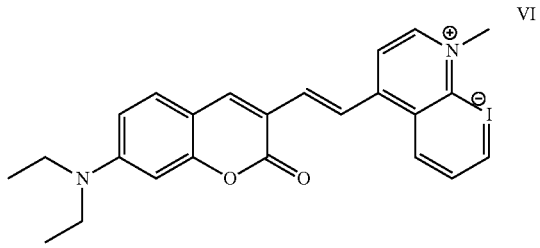

VI or its isomer.

In an embodiment of the present disclosure, the isomer is

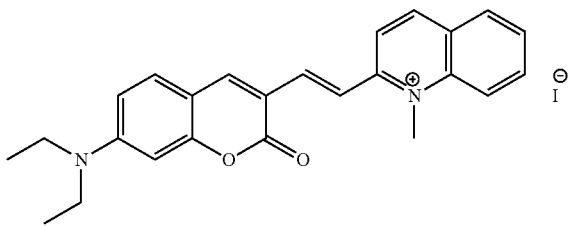 [SMILES: CCN(CC)c1ccc2cc(/C=C/c3ccc4ccccc4[n+]3C)c(=O)oc2c1 ; [I-]]

I

The present disclosure also relates to a process of preparing compound of Formula I, wherein the process comprises act of reacting a carbaldehyde derivative with heteroaryl derivative in presence of catalyst and solvent to obtain the compound.

In an embodiment of the present disclosure, the carbaldehyde derivative is 7-(dialkylamino)-2-oxo-2H-chromene-3-carbaldehyde or 7-(bis(2-chloroalkyl)amino)-2-oxo-2H-chromene-3-carbaldehyde.

In another embodiment of the present disclosure, the heteroaryl derivative is selected from group comprising N-alkylated 2-methyl benzthiazole, N-alkynylated 2-methyl benzthiazole, N-alkylated 2-methyl benzoxazole and 2-methyl benzoselinazole.

The present disclosure also relates to a process of preparing dimer of compound of Formula I, wherein the process comprises act of combining two monomers of formula I using linker.

The present disclosure also relates to a process of preparing compound of Formula V, wherein the process comprises act of reacting N-methylated benzothiazole and pyrene-1-carboxyaldehyde in presence of a catalyst and a solvent to obtain the compound.

The present disclosure also relates to a process of preparing compound of Formula VI, wherein the process comprises act of reacting carbaldehyde derivative with lepidine in presence of a catalyst and a solvent to obtain the compound.

The present disclosure also relates to a process of preparing the isomer of compound of Formula VI, wherein the process comprises act of reacting carbaldehyde derivative with 1-2 dimethylquinoline-1-ium in presence of a catalyst and a solvent to obtain the compound.

In an embodiment of the present disclosure, the carbaldehyde derivative is 7-(dialkylamino)-2-oxo-2H-chromene-3-carbaldehyde.

In another embodiment of the present disclosure, the catalyst is selected from group comprising base, acid, salt and combinations thereof.

In another embodiment of the present disclosure, the base is selected from group comprising piperidine, sodium acetate, sodium methoxide, potassium tert-butoxide and combinations thereof.

In another embodiment of the present disclosure, the solvent is selected from a group comprising ethanol, methanol, dichloromethane and combinations thereof.

In another embodiment of the present disclosure, the process is carried out at a temperature ranging from about 25° C. to about 90° C., and for a time period ranging from about 3 hours to about 10 hours.

In another embodiment of the present disclosure, the compound obtained is optionally purified.

The present disclosure relates to a method for detecting AT rich sequence in a sample comprising acts of;
a) incubating the sample with compound of Formula I, Formula V or Formula VI;
b) subjecting the incubated sample to fluorescence imaging for detecting the AT rich sequence.

The present disclosure relates to a method for detecting parasite in a sample comprising acts of:
a) incubating the sample with compound of Formula I, Formula V or Formula VI;
b) subjecting the incubated sample to fluorescence imaging for detecting the malarial parasite.

In an embodiment of the present disclosure, the parasite is selected from group comprising *P. falcipuram, P. vivax, P. ovale* and *P. malariae*.

In another embodiment of the present disclosure, the sample is selected from group comprising blood, urine, serum, plasma and saliva.

The present disclosure relates to a method for detecting Aβ aggregate in a sample comprising acts of:
a) incubating the sample with compound of Formula I or Formula VI;
b) subjecting the incubated sample to fluorescence imaging for detecting the Aβ aggregate.

In an embodiment of the present disclosure, upon said incubation, the compound of Formula I or Formula VI exhibits interaction selected from group comprising hydrophobic interaction with Leu17, Val39 of the A3 aggregate, n-n stacking interaction with the phenyl ring of Phe19 of the Aβ aggregate and a combination thereof.

The present disclosure also relates to a method for diagnosing disease selected from group comprising Alzheimer's disease, Frontotemporal Dementia and a combination thereof in a subject; wherein the method comprises acts of:
a) incubating sample obtained from the subject with compound of Formula I or Formula VI;

b) subjecting the incubated sample to fluorescence imaging for diagnosing said disease.

In an embodiment of the present disclosure, the subject is a mammal; and wherein the sample is selected from group comprising blood, urine, serum, plasma, cerebrospinal fluid and brain tissue.

The present disclosure relates to a compound of Formula I, Formula V or Formula VI for use in detecting AT rich sequence or Aβ aggregate.

The present disclosure also relates to a compound of Formula I, Formula V or Formula VI for use in diagnosing disease selected from group comprising malaria, Frontotemporal dementia and Alzheimer's disease or a combination thereof.

The present disclosure relates to a method of fluorescing AT rich DNA comprising act of incubating the DNA with compound of Formula I, Formula V or Formula VI.

The present disclosure also relates to a method of fluorescing Aβ aggregate comprising act of incubating the Aβ aggregate with compound of Formula I or Formula VI.

In an embodiment of the present disclosure, the compound of Formula I or Formula VI exhibits interaction selected from group comprising hydrophobic interaction with Leu17, Val39 of the Aβ aggregate, π-π stacking interaction with the phenyl ring of Phe19 of the Aβ aggregate and a combination thereof.

The present disclosure relates to a kit comprising compound of Formula I, Formula V or Formula VI and combinations thereof, optionally along with an instruction manual.

The present disclosure relates to hemicyanin compounds.

In a specific embodiment, the present disclosure provides for a compound of Formula I,

FORMULA I

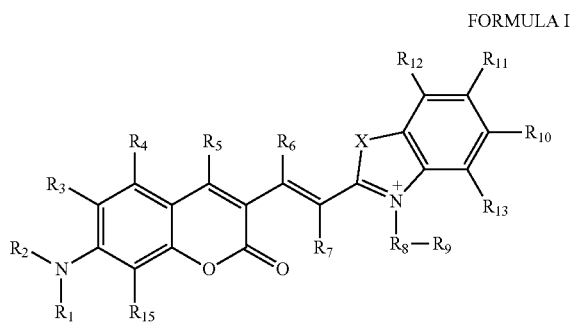

or its dimers,

Wherein,
- X is selected from a group comprising nitrogen, oxygen, sulphur, Se, —NH— and dimethylmethelene;
- R1 and R2 are selected from a group comprising H, alkyl chain (C1-C5) and substituted alkyl; preferably Halogen substituted alkyl;
- R3, R4 and R5 are selected from a group comprising H, OH, halogen, alkyl or substituted alkyl; wherein, halogen is selected from a group comprising bromide, chloride and iodide; and wherein the substituted alkyl is selected from group comprising alkyl substituted with halogen and alkyl substituted hydroxyl groups.
- R6 and R7 are selected from a group comprising H, alkyl, aryl, nitrile/cyano, acid and halogen; wherein halogen is selected from a group comprising, chloride, fluoride, bromide and iodide; and wherein acid is carboxylic acid.
- R8 is selected from a group comprising H and $-(CH_2)_n-$, wherein 'n' is 1-6.
- R9 is selected from a group comprising hydrogen, aryl, methyl, amines, substituted amines, terminal alkynes, alkenes, alkyl acids, amine acids, —OH, halogen and sulfonates ($SO_3^-$); wherein the substituted amine is alkyl substituted amine.
- R10, R11, R12 and R13 are selected from a group comprising H, OH, Alkyl, aryl, halogen, Nitro, sulfonates ($SO_3^-$) and nitrile/cyano group.
- R15 is selected from a group comprising H, OH, halogen, alkyl or substituted alkyl; wherein, halogen is selected from a group comprising bromide, chloride and iodide.
- Wherein, optionally R3 and R2, R1 and R15 form a cyclic structure.

In an embodiment, the compound of Formula I or its dimers is a small molecular probe.

In another embodiment, the compound of Formula I or its dimers is based on coumarin and is a small molecular fluorescent probe which detects AT-rich sequences in ds DNA.

In another embodiment of the present disclosure, the terms "compound", "probe" and "dye" are used interchangeably with each other.

In a preferred embodiment of the present disclosure, the compound of formula I and their dimers act as probe and hence finds application in fluorescence spectroscopy, diagnostics, bio-imaging, molecular and cell biology.

In an embodiment of the present disclosure, a substituted coumarin compound is provided:

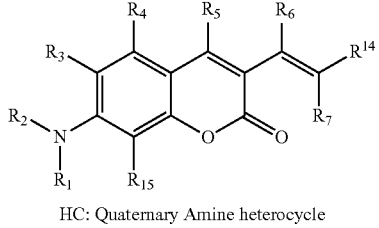

HC: Quaternary Amine heterocycle wherein:
$R^1$ and $R^2$ are either same or different and selected from a group comprising but not limiting to, H, alkyl (C1-C4), aryl and alkyl (C1-C4) substituted with halogen and alcohol groups and wherein:
  alkyl (C1-C4) is selected from a group comprising but not limiting to $CH_3$, $CH_2CH_3$ and $CH_2CH_2CH_3$.
  aryl is selected from a group comprising but not limiting to phenyl, naphthyl, thienyl and indolyl.
  alkyl (C1-C4) substituted with halogen and alcohol groups are selected from a group comprising but not limiting to $CH_2CH_2C$ $CH_2CH2Br$, $CH_2CH_2I$, and $CH_2CH_2OH$ groups.
$R^3$, $R^4$, $R^5$ and $R^{15}$ are same or different and are selected from a group comprising but not limiting to, H, OH, halogen, alkyl and alkyl substituted with halogen or hydroxyl groups and
wherein,
halogen is selected from a group comprising but not limiting to, chloride, iodide and bromide.
alkyl is selected from a group comprising but not limiting to methyl, alkyl, propyl and butyl.
aryl substituted with halogen or hydroxyl groups is selected from a group comprising but not limiting to, phenyl, naphthyl, thienyl and indolyl.

R⁶ and R⁷ are same or different and are selected from a group comprising but not limiting to H, alkyl, aryl or halogen and wherein, alkyl is selected from a group comprising but not limiting to, methyl, ethyl, propyl and butyl.

aryl is selected from a group comprising but not limiting to, phenyl, naphthyl, thienyl and indolyl.

halogen is selected from a group comprising but not limiting to, chloride, bromide and iodide.

In an embodiment of the present disclosure, substituted alkene bridge is provided:

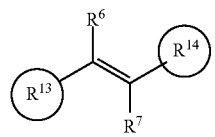

wherein:

R¹³ is selected from a group comprising but not limiting to coumarin, julolidine or aryl; and R¹⁴ is selected from a group comprising but not limiting to benzooxazol, Benzothiazol, picoline, chinalidine or lipidine.

In another embodiment of the present disclosure, the compound of formula I is classified into five groups based on the side groups.

Type 1: Basic Molecule is the Same Only X— Will Vary

Some non-limiting examples of Type-I compounds are provided below:

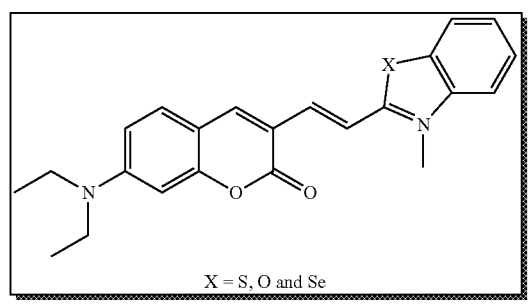

X = S, O and Se

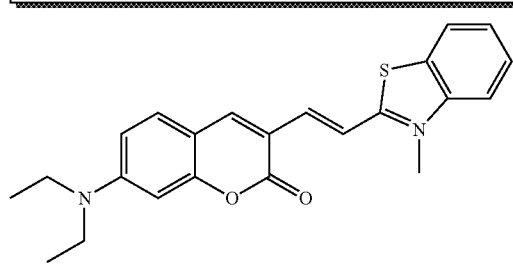

(E)-3-(2-(N-methyl-benzo[d]thiazol-2-yl)vinyl)-7-(diethylamino)-2 H-chromen-2-one (TC)

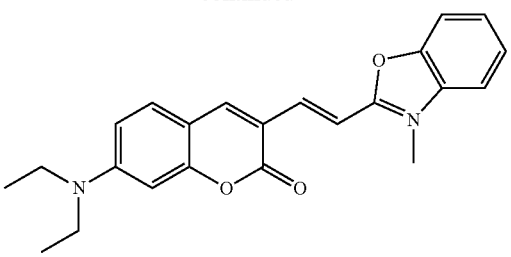

(E)-3-(2-(N-methyl-benzo[d]oxazol-2-yl)vinyl)-7-(diethylamino)-2 H-chromen-2-one

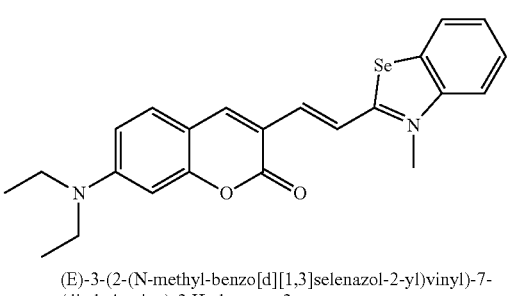

(E)-3-(2-(N-methyl-benzo[d][1,3]selenazol-2-yl)vinyl)-7-(diethylamino)-2 H-chromen-2-one Type 2: Basic Molecule is Same Only R— Will Vary

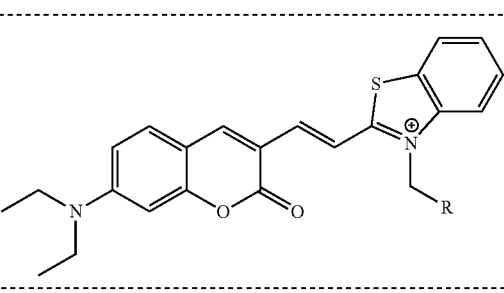

Some non-limiting examples of Type-2 compounds are provided below:

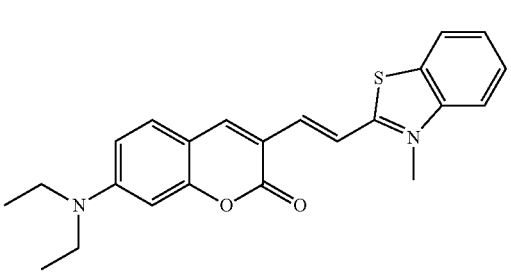

(E)-3-(2-(1-N-methyl-benzo[d]thiazol-2-yl)vinyl)-7-(diethylamino)-2 H-chromen-2-one (TC)

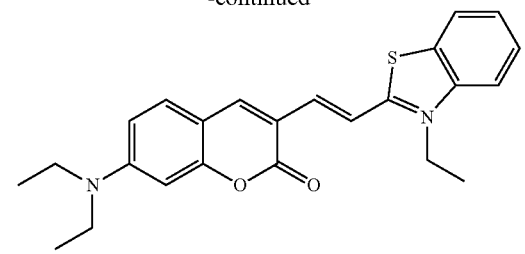

(E)-3-(2-(N-ethyl-benzo[d]thiazol-2-yl)vinyl)-7-(diethylamino)-2 H-chromen-2-one

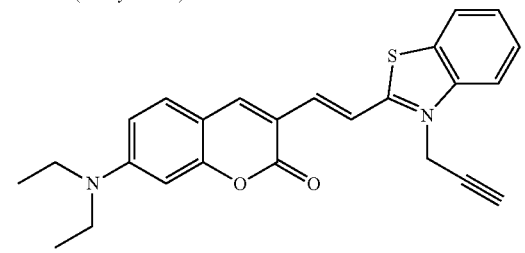

(E)-3-(2-(N-(prop-2-ynyl)-benzo[d]thiazol-2-yl)vinyl)-7-(diethylamino)-2 H-chromen-2-one

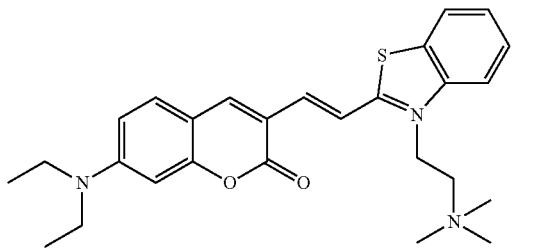

(E)-3-(2-(N-(N,N, N-trimethyl-2aminoethyl)-benzo[d]thiazol-2-yl)vinyl)-7-(diethylamino)-2 H-chromen-2-one

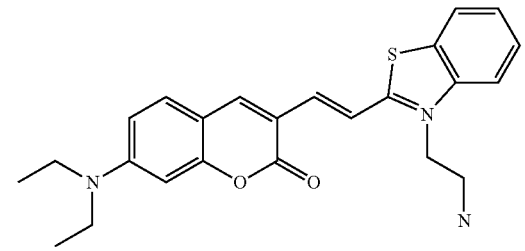

(E)-3-(2-(N-(2-aminium ethyl)-benzo[d]thiazol-2-yl)vinyl)-7-(diethylamino)-2 H-chromen-2-one

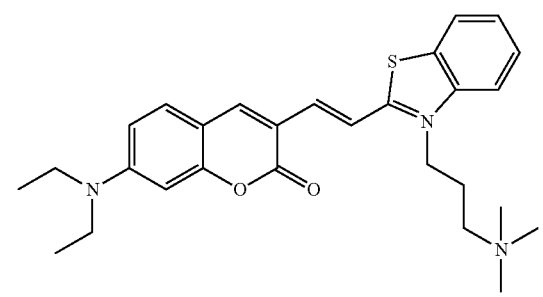

(E)-3-(2-(N-(N, N, N-trimethyl-3-aminopropyl)-benzo[d]thiazol-2-yl)vinyl)-7-(diethylamino)-2 H-chromen-2-one Type 2 Derivatives Examples: TCE and TCP

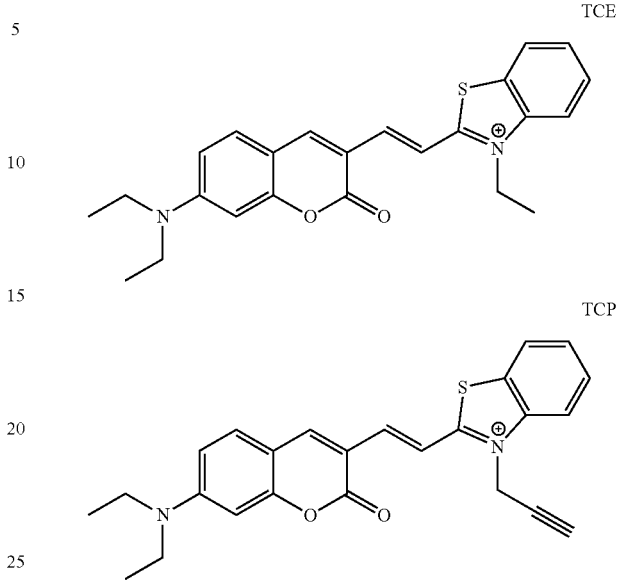

Type 3: Basic Molecule is Same Only R— Will Vary

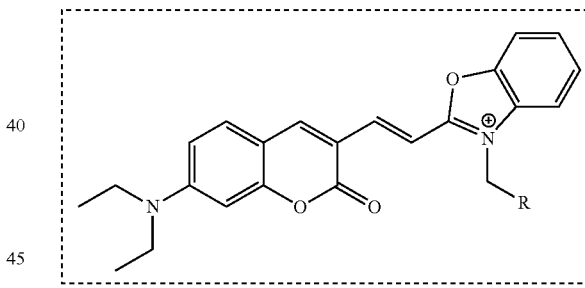

Some non-limiting examples of Type-3 compounds are provided below:

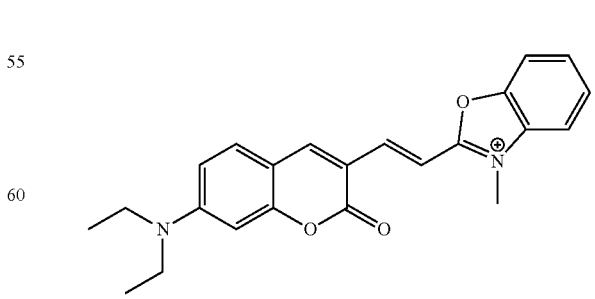

(E)-3-(2-(N-methyl-benzo[d]oxazol-2-yl)vinyl)-7-(diethylamino)-2H-chromen-2-one

-continued

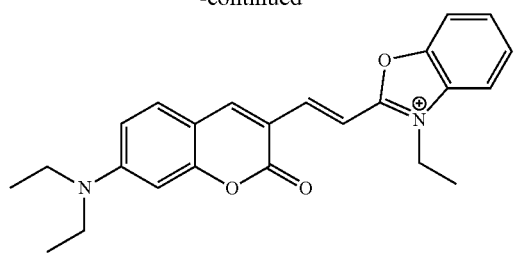

(E)-3-(2-(N-ethyl-benzo[d]oxazol-2-yl)vinyl)-7-(diethylamino)-2H-chromen-2-one

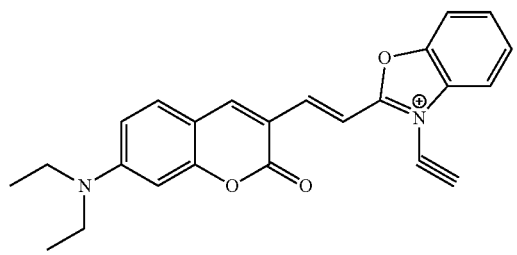

(E)-3-(2-(N-(prop-2-ynyl)-benzo[d]oxazol-2-yl)vinyl)-7-(diethylamino)-2H-chromen-2-one

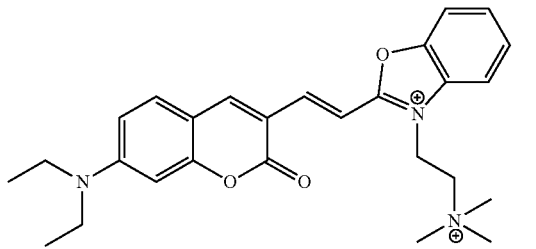

(E)-3-(2-(N-(N, N, N-trimethyl-2-aminoethyl)-benzo[d]oxazol-2-yl)vinyl)-7-(diethylamino)-2H-chromen-2-one

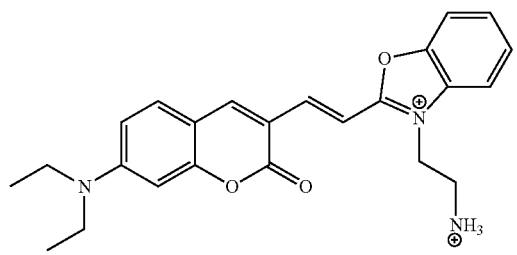

(E)-3-(2-(N-(2-aminium ethyl)-benzo[d]oxazol-2-yl)vinyl)-7-(diethylamino)-2H-chromen-2-one

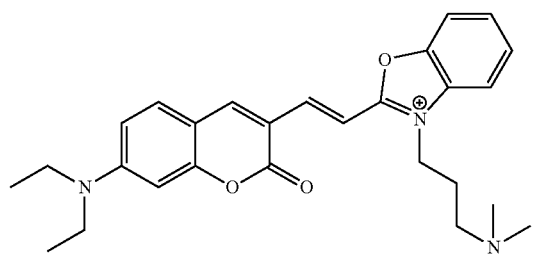

(E)-3-(2-(N-(N, N, N-trimethyl-3-aminopropyl)-benzo[d]oxazol-2-yl)vinyl)-7-(diethylamino)-2H-chromen-2-one Type 4: Basic Molecule is Same Only R— Will Vary Some non-limiting examples of Type-4 compounds are provided below:

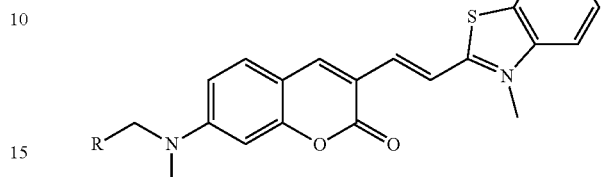

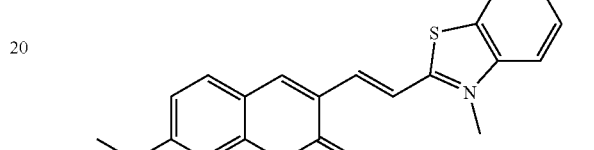

(E)-3-(2-(N-methyl-benzo[d]thiazol-2-yl)vinyl)-7-(dimethylamino)-2 H-chromen-2-one

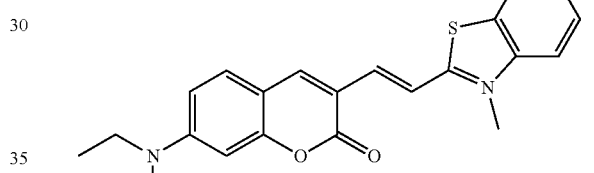

(E)-3-(2-(N-methyl-benzo[d]thiazol-2-yl)vinyl)-7-(diethylamino)-2 H-chromen-2-one(TC)

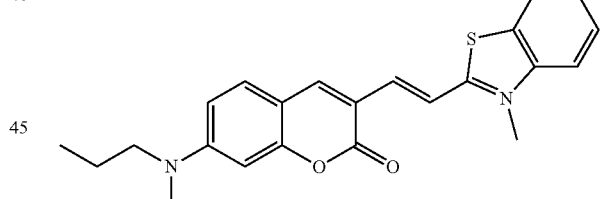

(E)-3-(2-(N-methyl-benzo[d]thiazol-2-yl)vinyl)-7-(dipropylamino)-2 H-chromen-2-one

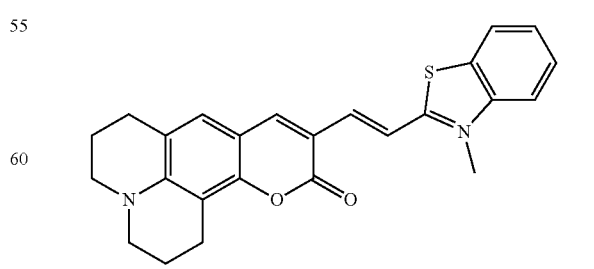

Thiazole Julidinal (TJ)

(2,3,6,7-Tetrahydro-8-hydroxy-1H,5H-benzo[ij]quinolizine-9-carboxaldehyde)

Some non-limiting examples for Type 4:

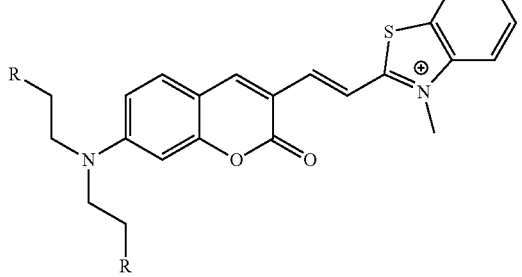

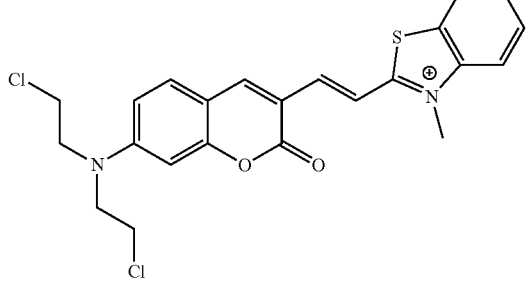

(E)-3-(N-Methyl2-(benzo[d]thiazol-2-yl)vinyl)-7 (bis(2-chloroethyl)amino)-2H-chromen-2-one

TCA

Type 5: Basic Molecule is Same Only R— Will Vary

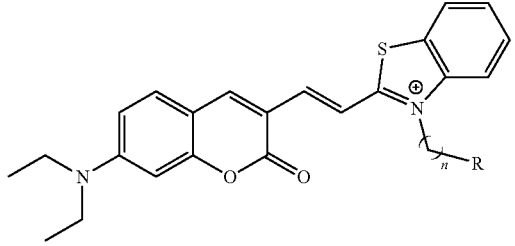

Some non-limiting examples of Type-5 compounds are provided below:

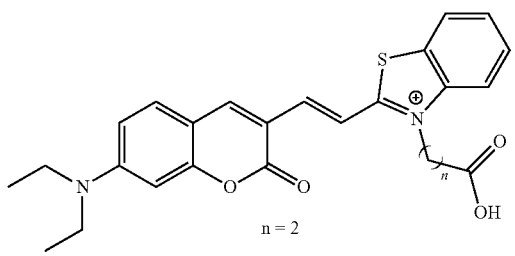

n = 2

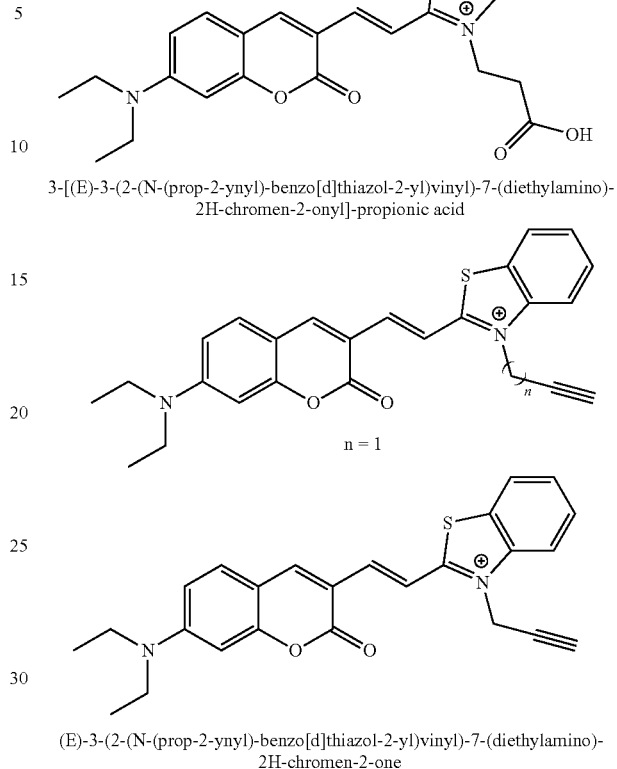

3-[(E)-3-(2-(N-(prop-2-ynyl)-benzo[d]thiazol-2-yl)vinyl)-7-(diethylamino)-2H-chromen-2-onyl]-propionic acid n = 1

(E)-3-(2-(N-(prop-2-ynyl)-benzo[d]thiazol-2-yl)vinyl)-7-(diethylamino)-2H-chromen-2-one

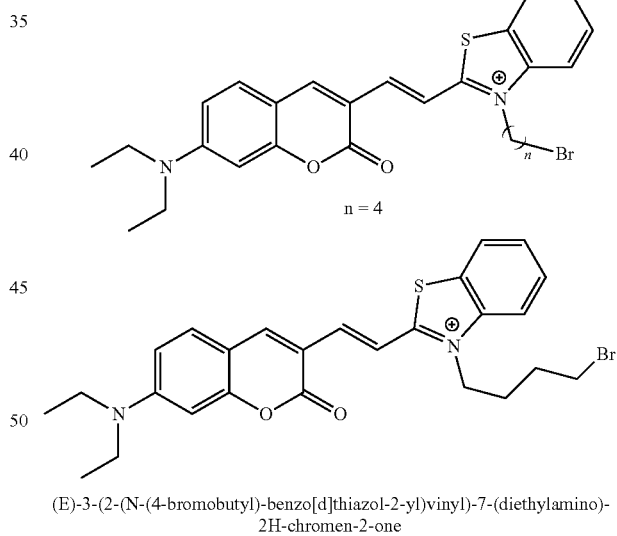

n = 4

(E)-3-(2-(N-(4-bromobutyl)-benzo[d]thiazol-2-yl)vinyl)-7-(diethylamino)-2H-chromen-2-one In an embodiment of the present disclosure, the side groups —Br, —COOH and alkynes of the probes can easily bind to DNA and protein aggregates through —N or —O alkylation, amide bond and triazole respectively.

In a preferred embodiment, the probes of the instant disclosure bind to AT rich sequences of DNA and Aβ aggregates and exhibit enhancement in fluorescence.

In yet another embodiment, the present disclosure provides a compound of formula II, III and IV which are dimers of compound of Formula I:

FORMULA II

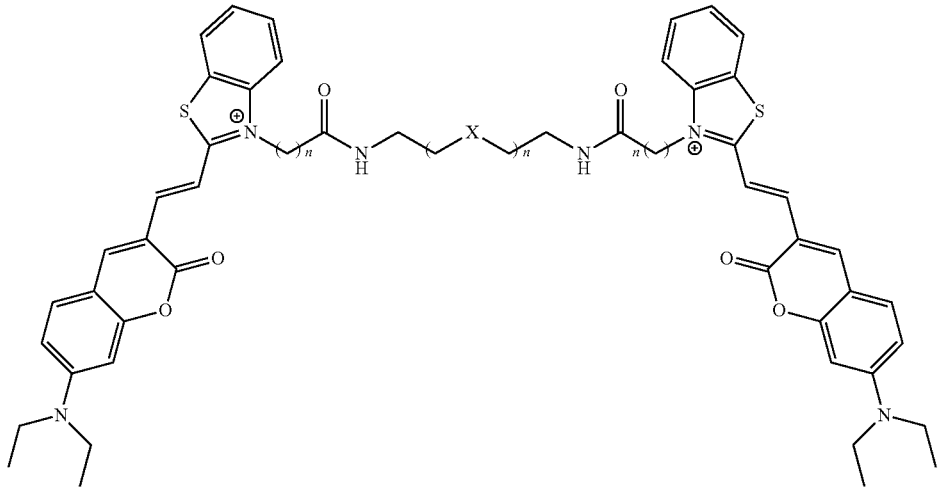

In an embodiment of the present disclosure, X is varied with various linkers selected from a group comprising, but not limited to, ethylene glycol, aliphatic, aromatic, polyamines and quaternary amine linkers; wherein aliphatic linkers are selected from group comprising but not limited to alkyl chain (C2 to C5); aromatic linkers are selected from group comprising but not limited to phenyl and naphthyl.

FORMULA III

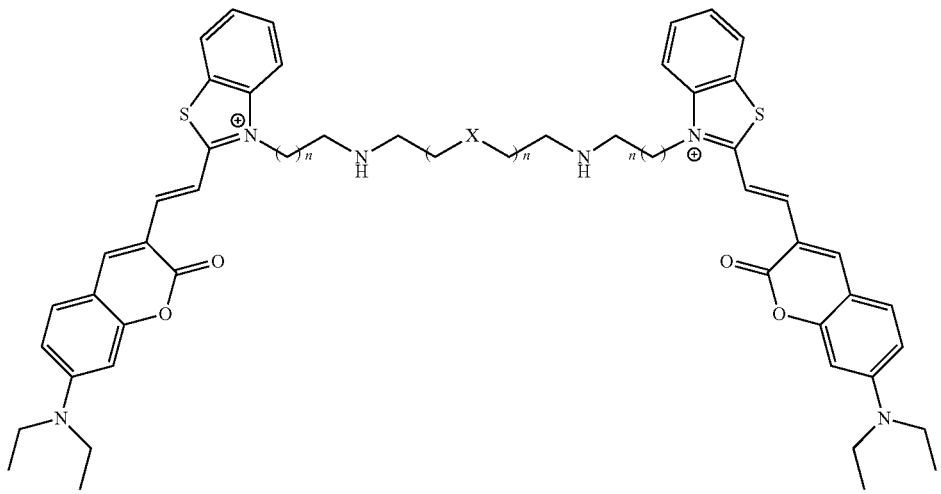

In an embodiment of the present disclosure, X is varied with various linkers selected from group comprising but not limited to ethylene glycol, aliphatic, aromatic, polyamine and quaternary amine linkers with N-alkylation and wherein the aliphatic linker is selected from group comprising but not limited to alkyl chain (C2 to C5); aromatic linkers are selected from group comprising but not limited to phenyl and naphthyl.

Formula IV

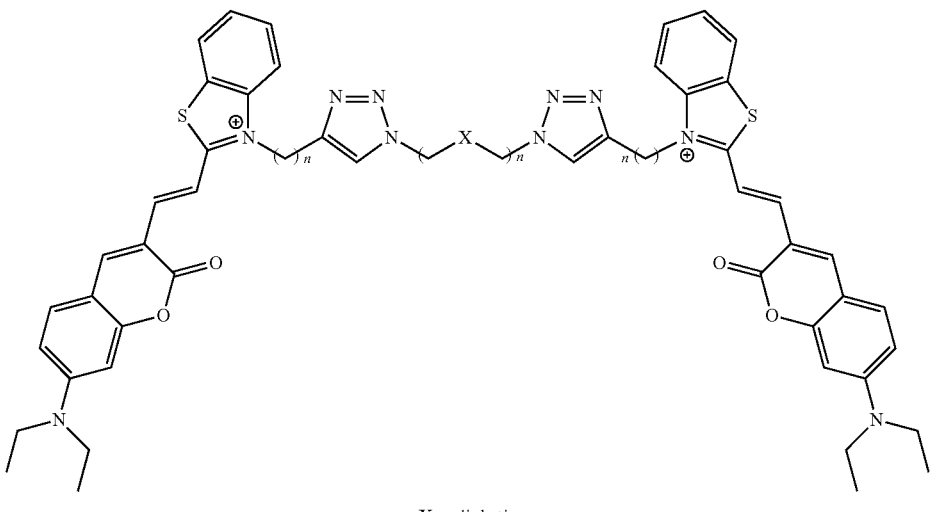

X = aliphatic

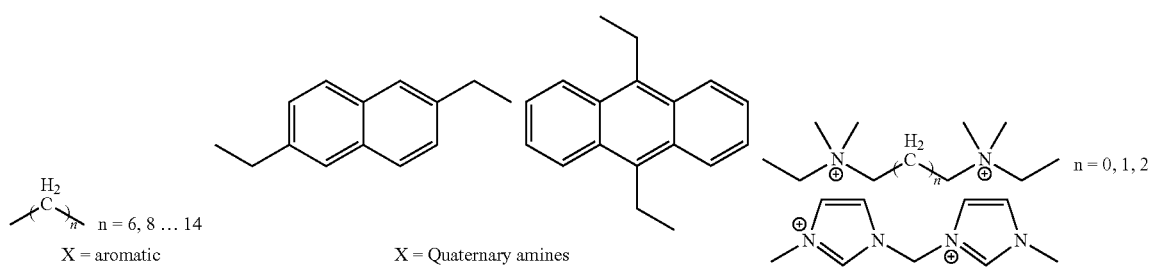

In an embodiment of the present disclosure, in compounds II, III and IV, X is varied with various linkers including but not limited to ethylene glycol, aliphatic, aromatic, polyamine and quaternary amine linkers using Click chemistry.

In yet another embodiment, the present disclosure provides a thiazole pyrene compound (TP) of formula V as provided below:

FORMULA V

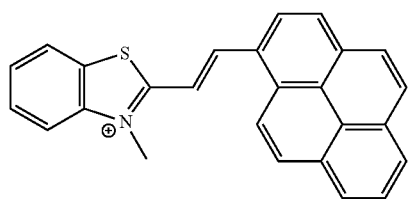

In yet another embodiment, the present disclosure provides a coumarin lepidine compound (CL) of formula VI as provided below:

FORMULA VI

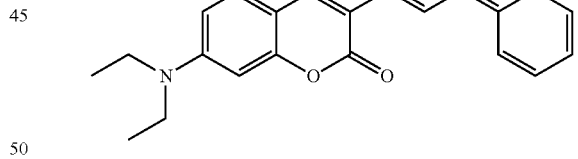

or its isomers.

In an embodiment, the isomer is Quinoline Coumarin (QC) of formula VII and the structural formula is provided below:

FORMULA VII

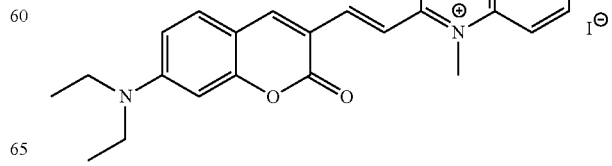

In yet another embodiment, the present disclosure provides use of any of compounds I to VII as fluorescent dyes or probes for detecting AT rich sequences in a DNA sample. Said compounds are red fluorescent dyes and highly specific to AT rich sequences on DNA. The compounds of the present disclosure are thus useful for detecting the presence of AT rich sequences in a double stranded DNA or a DNA sample.

In yet another embodiment, the present disclosure provides a method for detecting AT rich sequences in a DNA sample.

In an embodiment, the method of detecting AT rich sequence in DNA involves the interaction or incubation of the fluorescent dye (compounds of formula I to VII) with the sample containing DNA for about 5 seconds to about 90 seconds at a temperature ranging from about 20° C. to about 40° C., wherein the probes interact with AT-rich sequences of the DNA via intercalation.

In an exemplary embodiment, the incubation of the florescent dye with the sample containing DNA is carried out for about 60 seconds at a temperature of about 25° C.

In an embodiment, the probes of the present disclosure intercalates with AT-rich regions of DNA. In general, most of the cyanine dyes are non-fluorescent in buffer solution due to the "intramolecular twisting". Similarly, the probes of the present disclosure are also non-fluorescent in buffer solution mainly due to the intramolecular twisting. However, AT-regions of DNA provide favourable constrained environment to the probes by restricting their intramolecular twisting which results in enhancement in fluorescence.

In order to validate this concept, fluorescence studies in presence of Glycerol solution (also shown in FIG. 29) have been conducted. Glycerol is more viscous than Tris-HCl buffer solution itself and the viscous nature of glycerol helps in freezing the intramolecular rotation of probe TC to attain the planar molecular structure with maximum electron delocalization which results in the fluorescence enhancement of probe TC. Emission spectra of probe TC shows linear increase in fluorescence intensity with increasing percentage of glycerol content. This further confirms that the origin of the fluorescence enhancement of TC in presence of AT-regions of DNA is mainly due to restriction of intramolecular twisting of the probe TC.

In an embodiment of the present disclosure, the key criteria that a dye must possess to qualify as fluorescent DNA probe are to be non-fluorescent in unbound state and strongly fluoresce in bound state, exhibit longer excitation/emission wavelengths, non-toxicity and increased cell permeability.

The present disclosure relates to hemicyanin compounds for detecting AT rich sequences in DNA or a biological sample containing DNA.

Accordingly, in the present disclosure, new cell-permeable, non-toxic and highly AT-base pair selective red fluorescent hemicyanine-based compounds (compounds of formula I to IV) along with compounds TP, CL and QC are disclosed as probes for DNA recognition and nuclear staining in live cells.

In another embodiment of the present disclosure, compounds of formula I to IV, compound of formula V(TP), compound of formula VI (CL) and compound of formula VII (QC) exhibit strong fluorescence enhancements in presence of DNA containing AT-base pairs while non-fluorescent with DNA containing only GC-bases pairs, single-stranded DNA, RNA and proteins. The exponential increase in fluorescence of the compounds of the present disclosure as a function of consecutive AT-base pairs also suggests AT-rich regions are the preferable binding sites.

In still another embodiment of the present disclosure, the fluorescence staining in HeLa S3 and HEK293 cells and nuclease enzyme digestion studies reveal the selective staining of cell nucleus by the compounds of the present disclosure over cytoplasmic region.

Accordingly, the compounds of the present disclosure are promising AT-selective red fluorescent probes for DNA recognition and nuclear staining in live cells and find application in fluorescence spectroscopy, diagnostics and bio-imaging.

In an embodiment of the present disclosure, sequence-specific recognition (AT-rich) of DNA by small switch-on fluorescence probe is a promising tool for bio-imaging, bio-analytical and biomedical applications.

In yet another embodiment of the present disclosure, in the presence of DNA containing AT-base pairs, Hoechst33258 and the compounds of the present disclosure act as a donor-acceptor pair enabling their use as fluorescence resonance energy transfer (FRET) probes.

In another embodiment of the present disclosure, Fluorescence-activated cell sorting (FACS) analysis by flow cytometry demonstrates the application of the compounds of the present disclosure in cell cycle analysis in HEK 293 cells.

In yet another embodiment, the present disclosure provides use of any of compounds I to IV, VI and VII as fluorescent dyes or probes for detecting Aβ aggregates in a sample. Said compounds are red fluorescent dyes and highly specific to Aβ aggregates. The compounds of the present disclosure are thus useful for detecting the presence of Aβ aggregates in a sample when compared to other protein aggregates.

In yet another embodiment, the present disclosure provides a method for detecting Aβ aggregates in a sample.

In an embodiment, the method for detecting Aβ aggregates involves the interaction or incubation of the fluorescent dye/probe (any of compounds of formula I to IV, VI or VII) with the sample for about 5 seconds to about 90 seconds at a temperature ranging from about 20° C. to about 40° C.

In an exemplary embodiment, the incubation of the florescent dye with the sample containing Aβ aggregates is carried out for about 60 seconds at a temperature of about 25° C.

In an embodiment, the probes (any of compounds of formula I to IV, VI or VII) interact with Aβ aggregates through intercalation.

In a specific embodiment, the probes (any of compounds of formula I to IV, VI or VII) exhibit interaction selected from group comprising hydrophobic interaction with Leu17, Val39 of the Aβ aggregate, π-π stacking interaction with the phenyl ring of Phe19 of the Aβ aggregate and a combination thereof.

In an embodiment of the present disclosure, the key criteria that a dye must possess to qualify as fluorescent probe are to be non-fluorescent in unbound state and strongly fluoresce in bound state, exhibit longer excitation/emission wavelengths, non-toxicity and increased cell permeability.

The present disclosure relates to hemicyanin compounds for detecting Aβ aggregates in a biological sample.

Accordingly, in the present disclosure, non-toxic, biocompatible, serum stable and highly specific red fluorescent hemicyanine-based compounds (compounds of formula I to IV) along with compounds CL (formula VI) and QC (formula VII) are disclosed as probes for detection of Aβ aggregates.

In another embodiment of the present disclosure, compounds of formula I to IV, compound of formula VI (CL) and compound of formula VII (QC) exhibit strong fluorescence enhancements in presence of Aβ aggregates while non-fluorescent to other protein aggregates. The exponential increase in fluorescence of the compounds of the present disclosure in the presence of Aβ aggregates enable their use as markers for diagnosing diseases characterized by Aβ aggregates since they do not show enhancement in fluorescence with other protein aggregates which are characteristics of other disorders.

In an embodiment, the disease characterized by Aβ aggregates is selected from group comprising Alzheimer's disease (AD) and Frontotemporal Dementia.

In an embodiment, the present disclosure relates to a process for preparing a compound of formula I, said process comprising step of:
 a) adding base to a solution of heteroaryl derivative in solvent to obtain a reaction mixture;
 b) adding carbaldehyde derivative in solvent to the reaction mixture of step a) followed by stirring and evaporating the solvent to obtain the compound of formula I; and
 c) optionally purifying the compound of formula I.

In an embodiment, the heteroaryl derivative is selected from group comprising N-alkylated 2-methyl benzthiazole, N-alkynylated 2-methyl benzthiazole, N-alkylated 2-methyl benzoxazole and 2-methyl benzoselinazole.

In an embodiment, the carbaldehyde derivative is 7-(dialkylamino)-2-oxo-2H-chromene-3-carbaldehyde or 7-(bis(2-chloroalkyl)amino)-2-oxo-2H-chromene-3-carbaldehyde.

In a preferred embodiment, the carbaldehyde derivative is 7-(diethylamino)-2-oxo-2H-chromene-3-carbaldehyde or 7-(bis(2-chloroethyl)amino)-2-oxo-2H-chromene-3-carbaldehyde.

In an embodiment, the base is selected from group comprising piperidine, sodium acetate, sodium methoxide, potassium tert-butoxide and combinations thereof; preferably the base is piperidine.

In an embodiment, the solvent is selected from a group comprising ethanol, methanol, dichloromethane and combinations thereof.

In an embodiment, said process is carried out at a temperature ranging from about 25° C. to about 90° C., and for a time period ranging from about 3 hours to about 10 hours.

In an embodiment, the purification is carried out by chromatographic technique.

In an embodiment, the present disclosure relates to a process for preparing dimer of compound of formula I, said process comprising act of combining two monomers of compound of formula I by a suitable linker.

In an embodiment, the present disclosure relates to a process for preparing a compound of formula V (TP), said process comprising step of:
 a) adding base to a solution of N-methylated benzothiazole in solvent and stirring to obtain a reaction mixture;
 b) adding pyrene-1-carboxyaldehyde in solvent to the reaction mixture of step a) followed by stirring and evaporating the solvent to obtain the compound of formula V; and
 c) optionally purifying the compound of formula V.

In an embodiment, the catalyst, solvent, temperature, time period and purification technique are the same as provided for the preparation of compound of Formula I.

In an embodiment, the present disclosure relates to a process for preparing a compound of formula VI (CL), said process comprising step of:
 a) adding base to a solution of lepidine in solvent and stirring to obtain a reaction mixture; b) adding carbaldehyde derivative in solvent to the reaction mixture of step a) followed by stirring and evaporating the solvent to obtain the compound of formula VI; and
 c) optionally purifying the compound of formula VI.

In an embodiment, the catalyst, solvent, temperature, time period and purification technique are the same as provided for the preparation of compound of Formula I.

In an embodiment, the carbaldehyde derivative is 7-(dialkylamino)-2-oxo-2H-chromene-3-carbaldehyde.

In a preferred embodiment, the carbaldehyde derivative is 7-(diethylamino)-2-oxo-2H-chromene-3-carbaldehyde.

In an embodiment, the present disclosure relates to a process for preparing a compound of formula VII (QC), said process comprising step of:
 a) adding base to a solution of 1-2 dimethylquinoline-1-ium in solvent to obtain a reaction mixture;
 b) adding carbaldehyde derivative in solvent to the reaction mixture of step a) followed by stirring and evaporating the solvent to obtain the compound of formula VII; and
 c) optionally purifying the compound of formula VII.

In an embodiment, the catalyst, solvent, temperature, time period and purification technique are the same as provided for the preparation of compound of Formula I.

In an embodiment, the carbaldehyde derivative is 7-(dialkylamino)-2-oxo-2H-chromene-3-carbaldehyde.

In a preferred embodiment, the carbaldehyde derivative is 7-(diethylamino)-2-oxo-2H-chromene-3-carbaldehyde.

The present disclosure provides for a method of detecting and diagnosing diseases or conditions in a subject, wherein the method comprises the act of contacting the compounds of the present disclosure with a sample obtained from the subject.

The present disclosure also provides a method for detecting AT rich sequence in a sample comprising acts of; incubating the sample with any of the compounds of the present disclosure; and subjecting the incubated sample to fluorescence imaging.

In an embodiment, the sample is a DNA containing sample.

In a preferred embodiment, the sample is AT-rich DNA containing sample.

In another embodiment, the sample is selected from group comprising artificially synthesized DNA, microbial cell, mammalian cell, blood, serum, urine, saliva and plasma.

The present disclosure also provides a method for detecting parasite/pathogen in a sample, comprising acts of: incubating the sample with any of the compounds of the present disclosure and subjecting the incubated sample to fluorescence imaging.

In an embodiment, the parasite is selected from group comprising *P. falcipuram, P. vivax, P. ovale* and *P. malariae*.

In another embodiment, the sample is selected from group comprising blood, urine, serum, plasma and saliva.

The present disclosure also provides a method for detecting Aβ aggregate in a sample comprising acts of: incubating the sample with any of compounds of formula I to formula IV or compound of formula VI or compound of VII subjecting the incubated sample to fluorescence imaging for detecting the Aβ aggregate.

In an embodiment, the sample is Aβ containing sample.

In another embodiment, the sample is selected from group comprising blood, urine, serum, plasma, saliva, cerebrospinal fluid and brain tissue.

The present disclosure also provides a method for diagnosing diseases selected from group comprising Alzheimer's disease and Frontotemporal Dementia in a subject comprising acts of: incubating sample obtained from the subject with any of compounds of formula I to formula IV or compound of formula VI or compound of VII and subjecting the incubated sample to fluorescence imaging for diagnosing the disease.

In an embodiment, the subject is a mammal including human being.

In another embodiment, the sample is selected from group comprising plasma, urine, blood, serum, Cerebrospinal fluid (CSF), brain tissue and saliva.

The present disclosure also relates to use of compounds of Formula I to VII for detecting AT rich sequence.

In another embodiment, compounds of the present disclosure are useful for diagnosing disease conditions including but not limiting to malaria.

The present disclosure also relates to use of any of compounds of formula I to formula IV or compound of formula VI or compound of VII for detecting Aβ aggregate.

In another embodiment, any of compounds of formula I to formula IV or compound of formula VI or compound of VII are useful for diagnosing disease conditions including Alzheimer's disease and Frontotemporal dementia.

The present disclosure also relates to a method of fluorescing AT rich DNA using the compounds of Formula I to VII as well as a method of fluorescing Aβ aggregate using any of compounds of formula I to formula IV or compound of formula VI or compound of VII.

The present disclosure also relates to a kit comprising compounds of Formula I to VII either alone or in combination optionally along with an instruction manual.

In an embodiment, the kit of the present disclosure is used for detecting AT rich sequences of DNA or for detecting Aβ aggregates in a sample.

In another embodiment, the kit of the present disclosure is used for diagnosing disease conditions selected from group comprising malaria, Frontotemporal dementia and Alzheimer's disease.

In another embodiment, the kit is used for any combinations of the above mentioned aspects.

The present disclosure is further described with reference to the following examples, which are only illustrative in nature and should not be construed to limit the scope of the present disclosure in any manner.

EXAMPLES

Standard Parameters:

All the chemicals, reagents, oligos ($dA_{20}$, $dT_{20}$, $dA_{10}$, $dT_{10}$, $dG_{10}$ and $dC_{10}$), control probes (Hoechst 33258, ethidium bromide and propidium iodide), primary antibody, Alexa A488 coupled secondary antibody, DNase I and RNase are purchased from Sigma-aldrich. $^1$H and $^{13}$C-NMR spectra are recorded on a Bruker AV-400 MHz spectrometer with chemical shifts reported as parts per million (ppm) (in CDCl3/DMSO-d6, tetramethylsilane as internal standard) at 20° C. UV-vis absorption and emission spectra are measured in quartz cuvette of 1 cm path length. The absolute fluorescence quantum yields are determined using an integrating sphere for the samples on FLSP920 spectrometer (Edinburgh Instruments). High resolution Mass spectra (HRMS) are obtained on Agilent Technologies 6538 UHD Accurate-Mass Q-TOF LC/MS spectrometer. All air and moisture sensitive reactions are carried out under an argon atmosphere.

Sample Preparation for UV-Vis and Fluorescence-Measurements

Stock solutions of TC and CL are prepared in double distilled water in the order of $10^{-3}$ M. Stock solution of TP (thiazole-pyrene) is prepared by dissolving in HPLC-grade dimethyl sulfoxide (DMSO) in the order of $10^{-3}$ M. These stock solutions are completely covered with aluminum foil to avoid photo-bleaching and stored at about −10° C.

DNA-stock solutions are prepared by dissolving oligo samples in double distilled water in the order of $10^{-4}$ M. Double stranded (ds) DNA samples are prepared by mixing equimolar concentrations of complementary strands in Tris-HCl (100 mM, pH=7.4) buffer solution and subjected to annealing by heating the sample to about 85° C. for about 15 minutes and cooled to room temperature for about 7 hours and stored in refrigerator for about 4 hours.

Absorption and Emission Spectra:

The UV-vis absorption spectra are recorded on a Perkin Elmer Model Lambda 900 spectrophotometer. Emission spectra are recorded on Perkin Elmer Model LS 55 spectrophotometer. Temperature dependent absorption measurements (UV-Vis melting studies) are carried out using Cary 5000 UV-vis-NIR spectrophotometer equipped with Cary temperature controller in the range of about 10° C. to about 90° C. with ramp rate of about 1° C./min.

Circular Dichroism (CD) Spectroscopy:

Circular dichroism measurements are carried out using a Jasco J-815 spectrometer equipped with Peltier-type temperature controller (CDF-4265/15) under nitrogen atmosphere to avoid water condensation. Scans are performed over the range of about 200-700 nm with a speed of about 100 nm/min and the spectra represent an average of three scans. A blank sample containing buffer solution (Tris-HCl, 100 mM, pH=7.4) is treated in the same manner and subtracted from the collected data.

Thermal Denaturation Studies:

Thermal denaturation studies of double stranded DNA samples in the absence and presence of probe TC are recorded in the temperature range of about 10° C. to about 90° C. with heating rate of about 1° C./min. The variable temperature/wavelength mode is used. Absorption is monitored at about 260 nm of about 5° C. interval. Melting temperatures (Tm) of DNA samples are calculated from the first derivatives of the absorption vs. temperature curves (thermal denaturation or melting curves) obtained by monitoring at about 260 nm.

Gel Electrophoresis Studies:

Agarose gel electrophoresis experiments are performed on custom-made horizontal gel system using 3% agarose gel at about 100 V for about 1 h at about 25° C. Then the dsDNA bands are visualized on the agarose gels by soaking in aqueous solution of TC or EtBr for about 30 minutes.

*Plasmodium falciparum* Culture and Probe TC Treatment:

*P. falciparum* 3D7 strain is grown at about 4-10% parasitemia in RPMI 1640 medium supplemented with 0.5% albumax (Invitrogen), 5% NaHCO3, 50 mg/mL gentamicin and 50 mg/mL ampicillin at about 37° C. The culture is synchronized by incubating ringstaged parasites for about 5 minutes with 5% sorbitol. Probe TC (resuspended in Mili-Q water) is added to parasites (3065 hpi) at a final concentration of 1 and 2 mM, and the parasites are incubated for about 30 minutes at about 37° C. Milli-Q water is used as a vehicle control. Fluorescence images are captured using Carl Zeiss AXIO Imager Z1 and the software used for image capturing is AxioVision Rel. 4.8.

Example 1: Preparation of Fluorescence Probes

Inspired by the basic core-structure of cyanine probes, three hemicyanine-based molecular probes compounds of formula I, coumarin-lepidine (CL), thiazole-pyrene (TP) and compounds of formula II to IV are designed with the objective of finding a superior DNA staining reagent. TP, CL and TC are depicted in FIG. 1. To elucidate the role of prudent positively charged quaternary amine group in benozothiazole-based probes, the benzothiazole group is replaced with quinoline moiety in CL. Similarly, coumarin group is substituted with hydrophobic pyrene in TP to understand the role of heterocyclic fluorophore moieties (coumarin/quinoline) in the benzothiazole-based probes. The choice of using coumarin chromophore in the probes is owing to its excellent fluorescence properties in the visible region. Further, these probes display excitation and emission in the longer wavelength of visible region owing to extended conjugation, an essential prerequisite to avoid auto-fluorescence and DNA photo-damaging during cellular imaging. One of the main characteristic optical property of a dye to qualify as a potential DNA binding and staining reagent is, it must be non-fluorescent or weekly fluorescent in unbound state and show highly enhanced fluorescence in the longer wavelength of visible region (red) upon interaction with DNA.

a) Synthesis of Compound 1

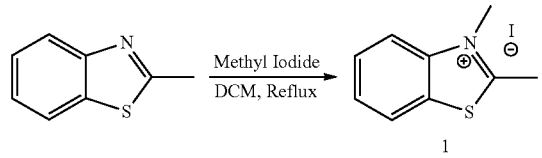

To a stirred solution of 2-methyl benzothiazole (7.0 mmol) in dichloromethane (10 mL), methyl iodide (14.0 mmol) is added drop wise and allowed to reflux for overnight. Completion of the reaction is monitored with TLC. After completion of the reaction, white color precipitate is formed. The precipitate is filtered and washed with copious amount of diethyl ether for removing unreacted benzothiazole. The obtained product is dried under vacuum and then used without further purification.

b) Synthesis of Compound 2

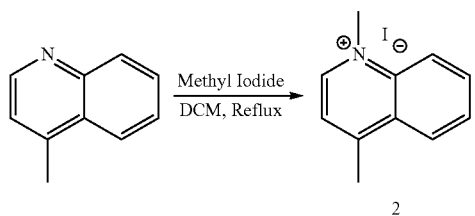

To a stirred solution of lepidine (5.0 mmol) in dichloromethane (10 mL), Methyl iodide (10.0 mmol) is added drop wise and allowed to reflux for overnight. After completion of the reaction, yellow color precipitate is formed. The precipitate is filtered and washed with more amount of dichloromethane for removing unreacted Lepidine. The obtained product is dried under vacuum and then used without further purification.

The compounds 1 and 2 are further used in the preparation of the compounds of the instant disclosure.

General Synthetic Procedure for Probe TC and CL 7-(Diethylamino)-2-oxo-2H-chromene-3-carbaldehyde (CCA) is prepared as per the well-known synthetic procedures in the art. To a stirred solution of compound 1 (N-methylated benzothiazole) or 2 (lepidine) (1.2 eq.) in ethanol, piperidine (0.2 eq.) is added and allowed to stir for 10 min. 7-(Diethylamino)-2-oxo-2H-chromene-3-carbaldehyde (1 eq.) in ethanol solution is added dropwise to the above reaction mixture. The color of the solution immediately changes from yellow to purple color and the reaction mixture is allowed to stir 4 h for completion. After completion of the reaction, solvent is evaporated under vacuum. The crude product is purified using column chromatography on silica gel using $CHCl_3$/MeOH as an eluent to afford probe in good yields.

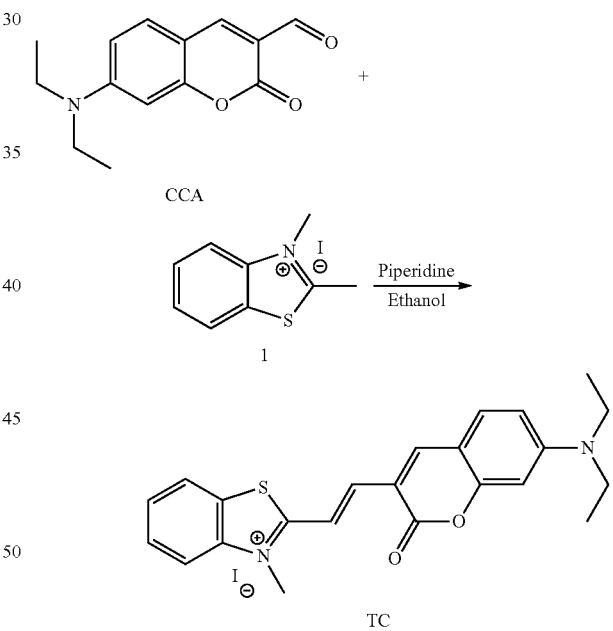

Probe TC:

Brown color powder, yield 50%.[2] $^1$H-NMR (DMSO-$d_6$, 400 MHz) δ 8.59 (s, 1H), 8.37 (dd, J=0.8 Hz, J=8 Hz, 1H), 8.21 (d, J=8.4 Hz, 1H), 8.02 (dd, J=8 Hz, J=15.6 Hz, 2H), 7.83 (m, 1H), 7.74 (td, J=1.2 Hz, J=7.6 Hz, 1H), 7.57 (d, J=9.2, 1H), 6.87 (dd, J=2.4 Hz, J=9.2 Hz, 1H), 6.67 (d, J=2.4 Hz, 1H), 4.22 (s, 3H), 3.53 (q, 4H, J=7.2 Hz), 1.17 (t, 6H, J=7.2 Hz). $^{13}$C-NMR (DMSO-$d_6$, 100 MHz) δ 171.6, 159.5, 157.1, 153.3, 148.3, 144.3, 142.0, 131.8, 129.2, 128.0, 127.4, 124.1, 116.5, 112.0, 111.3, 110.9, 108.9, 96.4, 44.6, 35.8, 12.4. (FIG. 20)

HRMS (ESI-MS): calcd for $C_{23}H_{23}N_2O_2SI$ [M–I]$^-$ m/z=391.1475, found 391.1456. (FIG. 23)

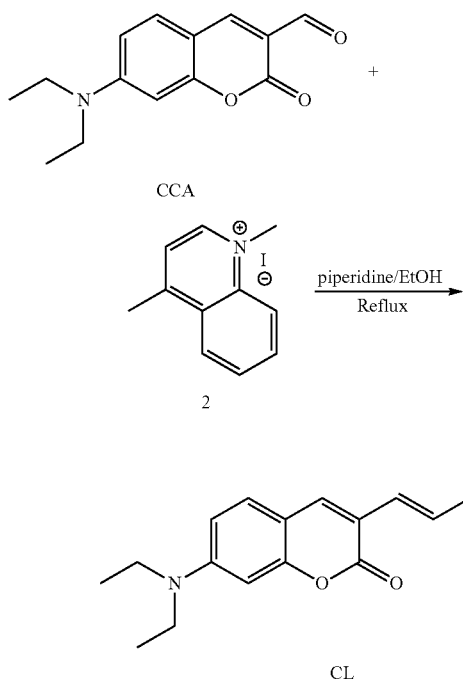

Probe CL:

Violet color powder, yield 60%. $^1$H-NMR (DMSO-$d_6$, 400 MHz) δ 9.25 (d, J=6.4 Hz, 1H), 8.72 (d, J=8 Hz, 1H), 8.43 (m, 4H), 8.24 (m, 1H), 8.02 (m, 2H), 7.54 (d, J=9.2 Hz, 1H), 6.82 (dd, J=2.4 Hz, J=9.2 Hz, 1H), 6.61 (d, J=2.4 Hz, 1H), 4.46 (s, 3H). $^{13}$C-NMR (DMSO-$d_6$, 100 MHz) δ 160.0, 158.2, 157.8, 152.4, 152.1, 147.7, 145.1, 138.7, 138.2, 134.8, 130.9, 129.3, 126.0, 125.6, 119.4, 118.4, 115.3, 114.8, 113.9, 110.2, 108.6, 96.3, 44.4, 12.4. (FIG. 21)

HRMS (ESI-MS): calcd for $C_{25}H_{23}IN_2O_2[M-I]^+$ m/z=385.1911, found 385.1902. (FIG. 24)

Synthesis of Probe TP

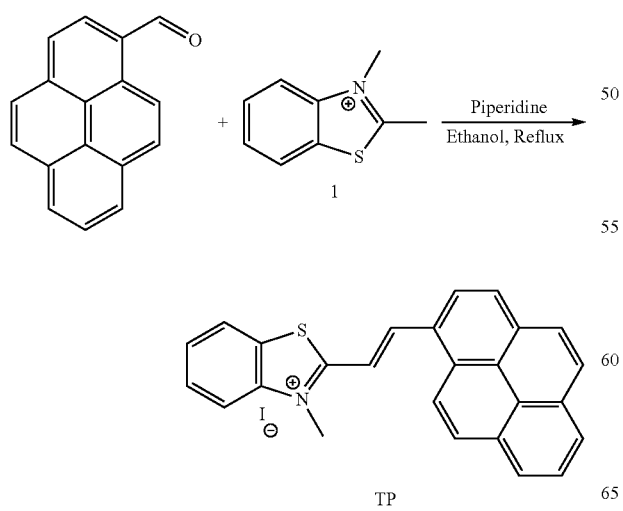

To a stirred solution of compound 1 (N-methylated benzothiazole) (164 mg, 5.65 mmol) in ethanol, piperidine (60 μL, 5.65 mmol) is added and allowed to stir for 10 min. Pyrene-1-carboxaldehyde (100 mg, 4.347 mmol) in ethanol solution is added drop wise to the reaction mixture with pressure equalizer and stirred under reflux conditions for 7 h. The completion of reaction is monitored with TLC. After completion of the reaction, solvent is evaporated under vacuum. The crude product is purified using column chromatography on silica gel using DCM/MeOH (98/2) as an eluent to afford probe TP. Brown color powder, yield 78%.

$^1$H-NMR (DMSO-$d_6$, 400 MHz) δ 9.19 (d, J=15.6 Hz, 1H), 8.97 (d, J=8.4 Hz, 1H), 8.88 (d, J=9.6 Hz, 1H), 8.39 (m, 9H), 8.18 (t, J=7.6 Hz, 1H), 7.92 (m, 1H), 7.84 (td, J=0.8 Hz, J=7.6 Hz, 1H), 4.46 (s, 3H). $^{13}$C-NMR (DMSO-$d_6$, 100 MHz) δ 171.5, 144.1, 142.0, 133.7, 130.8, 130.3, 130.1, 129.9, 129.5, 128.5, 128.1, 127.4, 127.3, 127.0, 126.7, 125.7, 125.5, 124.2, 124.0, 123.5, 122.6, 116.9, 115.4, 36.5. (FIG. 22)

HRMS (ESI-MS): calcd for $C26H_{18}INS$ $[M-I]^+$ m/z=376.1154, found 376.1156 (FIG. 25).

Synthesis of Compound 3

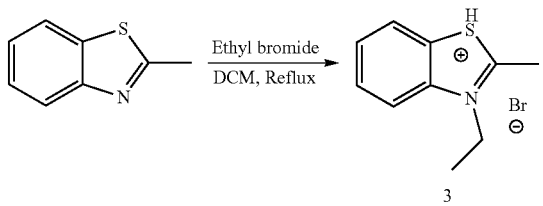

2-Methylbenzothiazole (1 equiv.) and ethyl bromide (4 equiv.) are stirred under $N_2$ atmosphere in DCM (6 mL) and allowed to reflux for 2 days. The completion of reaction is monitored with TLC. After completion of the reaction solvent is evaporated under vacuum. The obtained precipitate is washed with diethyl ether to get pure product.

Synthesis of Compound 4

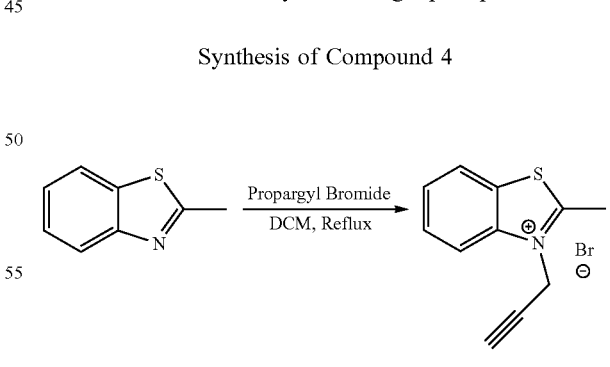

2-Methylbenzothiazole (1 equiv.) and propargyl bromide (4 equiv.) are stirred under $N_2$ atmosphere in DCM (6 mL) and allowed to reflux for 24 h. The completion of reaction is monitored with TLC. After completion of the reaction solvent is evaporated under vacuum. The obtained precipitate is washed with diethyl ether to get pure product.

Synthetic Procedure of 'Type 2' Derivatives TCE and TCP

Synthesis of Probe TCE {(E)-3-(2-(N-ethyl-benzo[d]thiazol-2-yl)vinyl)-7-(diethylamino)-2H-chromen-2-one)}

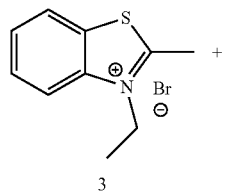

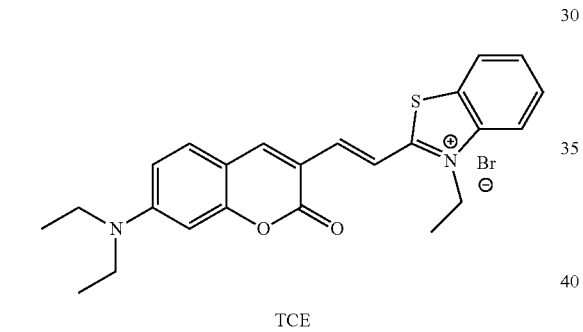

To a stirred solution of compound 3 (1.5 equiv.) in Methanol (2 mL), Piperidine (about 5 μL) is added. After about 10 minutes, 7-(diethylamino)-2-oxo-2H-chromene-3-carbaldehyde (CCA) (1 equiv.) in dichloromethane (DCM) (2 mL) solution is added to above reaction mixture and stirring is continued at about 50° C. for about 3 hours under $N_2$ atmosphere. After completion of reaction, solvent is evaporated. The crude product is purified using column chromatography on silica gel using Methanol\Dichloromethane (5:95) as an eluent to get red colored fluorescent solid compound. Red color solid, yield 62%.

$^1$H NMR (400 MHz, DMSO-$d_6$) δ ppm 1.17 (t, J=7.0 Hz, 6H), 1.49 (t, J=7.2 Hz, 3H), 3.54 (q, J=7.1 Hz, 4H), 4.79 (q, J=7.2 Hz, 2H), 6.67 (d, J=2 Hz, 1H), 6.88 (dd, J=2.4 Hz, 9.2 Hz, 1H), 7.58 (dd, J=9.2 Hz, 1H), 7.74 (m, 1H), 8.04 (s, 2H), 8.26 (d, J=8.4 Hz, 1H), 8.38 (d, J=7.6 Hz, 1H), 8.62 (s, 1H). $^{13}$C NMR (100 MHz, DMSO-d) δ ppm 12.4, 13.7, 44.2, 44.7, 96.5, 108.9, 110.7, 110.9, 111.9, 116.2, 124.3, 127.9, 128.0, 129.4, 131.8, 140.9, 144.8, 148.3, 153.3, 157.2, 159.6, 171.2. HRMS (ESI-MS): calcd for $C_{24}H_{25}N_2O_2SBr$ [M−Br]$^+$ m/z=405.1631, found 405.1619. (FIG. 34 and FIG. 35).

Synthesis of probe TCP (E)-3-(2-(N-(prop-2-ynyl)-benzo[d]thiazol-2-yl)vinyl)-7-(diethylamino)-2H-chromen-2-one)

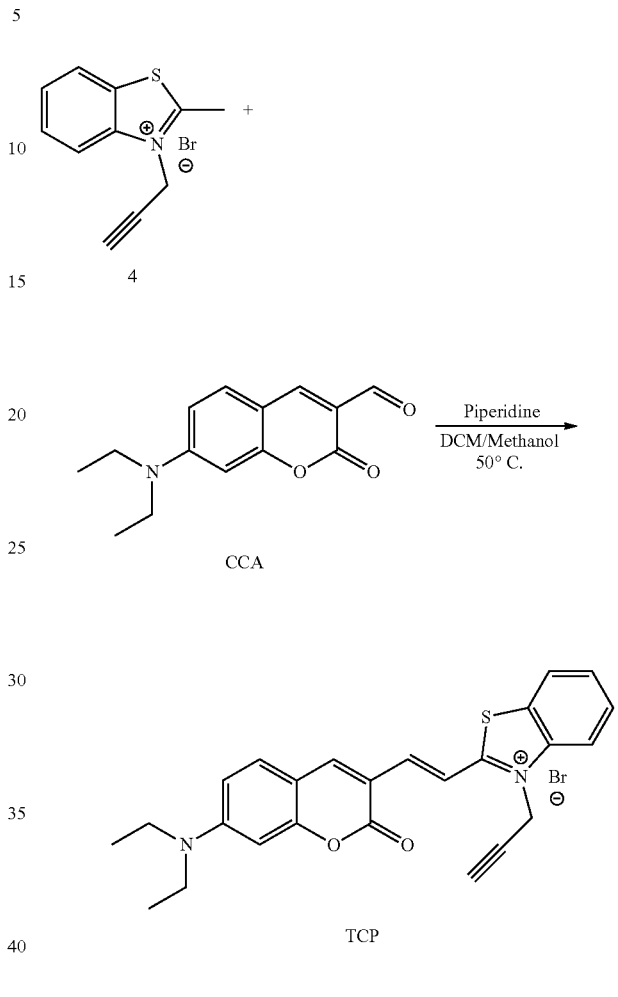

To a stirred solution of compound 4 (1.5 equiv.) in Methanol (2 mL), Piperidine (about 5 μL) is added. After about 10 minutes, 7-(diethylamino)-2-oxo-2H-chromene-3-carbaldehyde (CCA) (1 equiv.) in dichloromethane (DCM) (2 mL) solution is added to above reaction mixture and stirring is continued at about 50° C. for about 3 hours under $N_2$ atmosphere. After completion of reaction, solvent is evaporated. The crude product is purified using column chromatography on silica gel using Methanol\Dichloromethane (5:95) as an eluent to get red colored fluorescent solid compound. Red color solid, Yield 65%.

$^1$H NMR (400 MHz, DMSO-$d_6$) δ$_{ppm}$ 1.18 (t, J=7.2 Hz, 6H), 3.79 (t, J=2.4 Hz, 1H), 5.73 (d, J=2 Hz, 2H), 6.70 (d, J=2 Hz, 1H), 6.90 (dd, J=2.4 Hz, 9.2 Hz, 1H), 7.60 (d, J=8.8 Hz, 1H), 7.77 (t, J=8 Hz, 1H), 7.87 (dt, J=0.8 Hz, 7.2 Hz, 1H), 8.11 (d, J=1.2 Hz, 2H), 8.27 (d, J=8.8 Hz, 1H), 8.40 (d, J=8 Hz, 1H), 8.62 (s, 1H). $^{13}$C NMR (100 MHz, DMSO-$d_6$) δ$_{ppm}$ 12.4, 38.0, 44.7, 75.3, 78.6, 96.5, 109.1, 110.3, 111.1, 111.9, 116.1, 124.4, 127.4, 128.2, 129.6, 132.1, 140.6, 146.1, 148.9, 153.61, 157.4, 159.4, 172.3. HRMS (ESI-MS): calcd for $C_{25}H_{23}N_2O_2SBr$ [M−Br]$^-$ m/z=415.1475, found 415.1463. (FIG. 36 and FIG. 37)

Synthesis of (E)-3-(N-Methyl 2-(benzo[d]thiazol-2-yl)vinyl)-7-(bis(2-chloroethyl)amino)-2H-chromen-2-one (TCA)

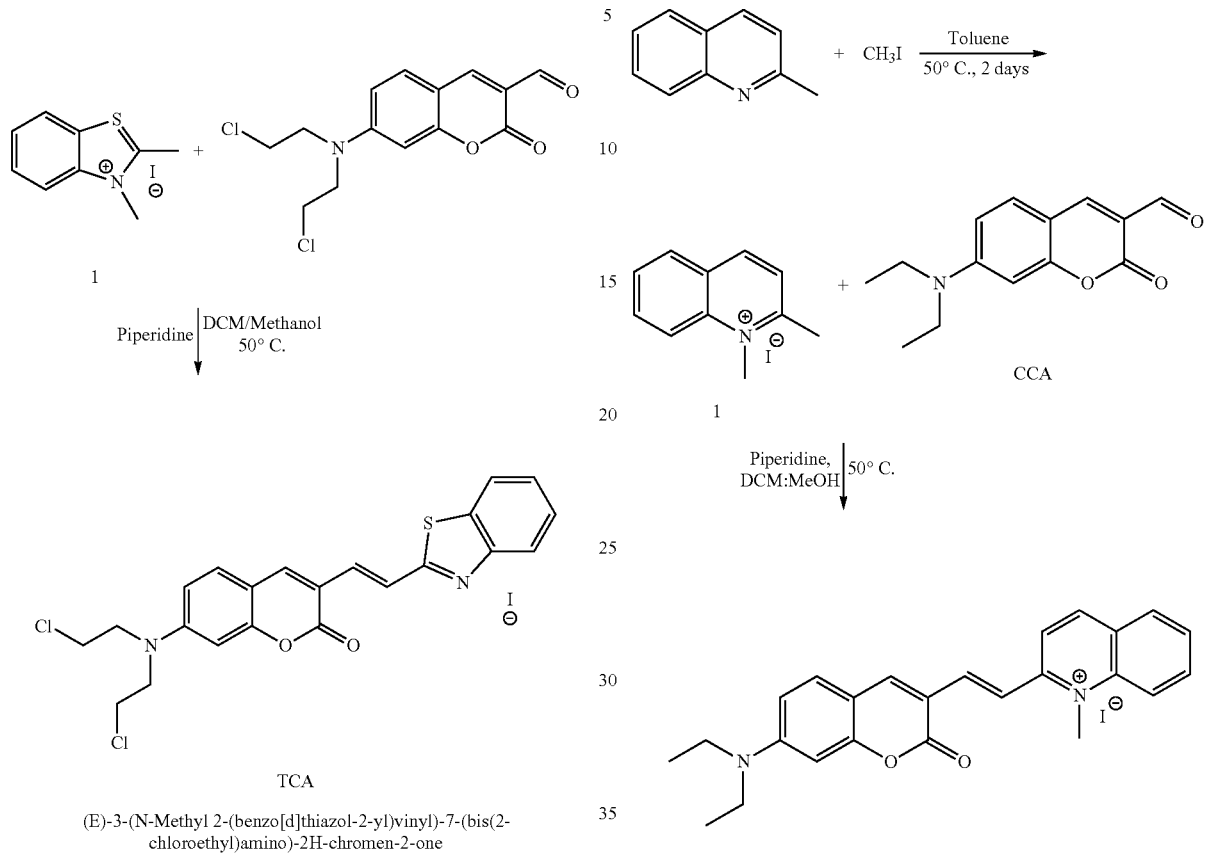

TCA (E)-3-(N-Methyl 2-(benzo[d]thiazol-2-yl)vinyl)-7-(bis(2-chloroethyl)amino)-2H-chromen-2-one To a stirred solution of compound 1 (about 70 mg, 0.24 mmol) in Methanol (about 5 mL), Piperidine (6 μL) is added. After about 15 minutes, 7-(bis(2-chloroethyl)amino)-2-oxo-2H-chromene-3-carbaldehyde (about 50 mg, 0.16 mmol) in DCM (about 5 mL) solution is added to above reaction mixture and stirring is continued at about 50° C. for about 6 hours under $N_2$ atmosphere. After completion of reaction, solvent is evaporated. The crude product is purified using column chromatography on silica gel using Methanol\Dichloromethane (3:97) as an eluent to get brown coloured powder, Yield 55%.

TCA is designed based on two strategies. The coumarin-thiazole part helps in bind the AT-rich sequences in intercalation mode and bis(2-chloroethyl)-N linkers helps in alkylating the DNA in covalent cross linking to DNA-base pairs and acts as anticancer drug (FIG. 74).

$^1$H NMR (400 MHz, DMSOd$_6$) $\delta_{ppm}$ 3.84 (t, J=6.4 Hz, 4H), 3.96 (t, J=6.4 Hz, 4H), 4.25 (s, 3H), 6.87 (d, J=2 Hz, 1H), 7.02 (d, J=2 Hz, 1H), 7.64 (d, J=9.2 Hz, 1H), 7.77 (td, J=0.8 Hz, 8 Hz, 1H), 7.86 (td, J=1.2 Hz, 8.4 Hz, 1H), 8.01 (d, J=15.2 Hz, 1H), 8.12 (d, J=15.6 Hz, 1H), 8.25 (d, J=8.8 Hz, 1H), 8.40 (dd, J=0.8 Hz, 8 Hz, 1H), 8.67 (s, 1H). $^{13}$C NMR (100 MHz, DMSO-d$_6$) $\delta_{ppm}$ 36.0, 41.0, 51.8, 97.9, 109.8, 111.1, 112.8, 113.9, 116.7, 124.2, 127.7, 128.2, 129.3, 131.6, 142.0, 143.7, 148.3, 153.0, 156.6, 159.3, 171.7 HRMS (ESI-MS): calcd for $C_{23}H_{21}Cl_2N_2O_2SI$ [M–I]$^+$ m/z=459.0695, found 459.0674 (FIG. 42 & FIG. 43)

Synthetic Procedure of QC (Formula VII)

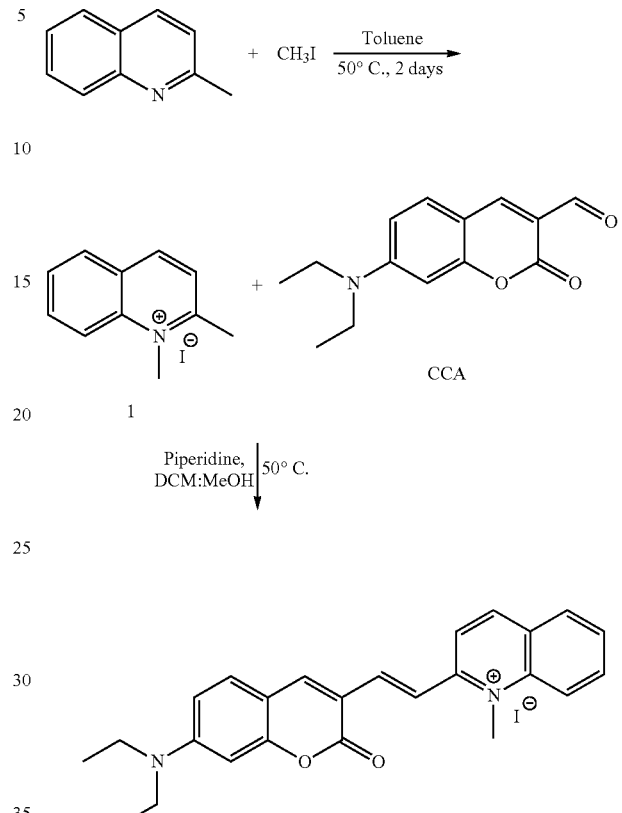

Synthesis of 1,2-dimethylquinolin-1-ium Iodide (Compound 1)

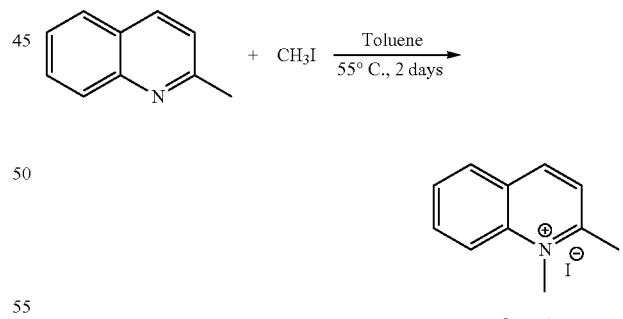

2-methylquinoline (about 1 ml, about 7 mmol) and Iodomethane (about 2 ml, about 28 mmol) are stirred under N2 atmosphere in Toluene (about 10 ml) at about 55° C. for about 2 days. The completion of reaction is monitored with TLC. After completion of the reaction, the solvent is evaporated under vacuum. The unreacted starting material is extracted using Dichloromethane. The yellow-colored crude product is directly used in next without any further purification.

Synthesis of 2-(2-(7-(diethylamino)-2-oxo-2H-chromen-3-yl)vinyl)-1-methylquinolin-1-ium Iodide (QC)

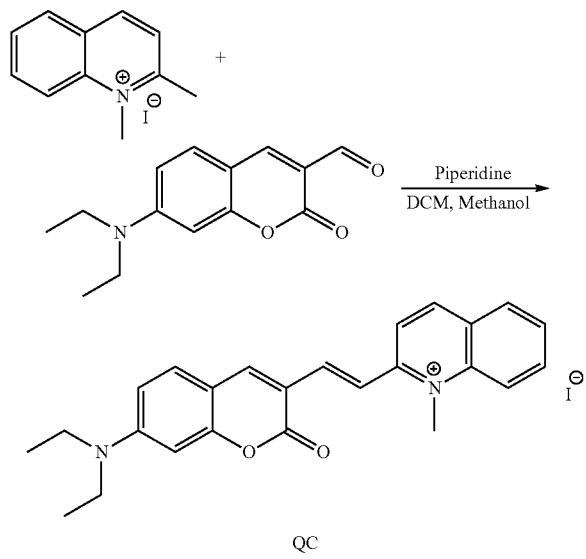

To a stirred solution of compound 1 (about 40 mg, about 0.14 mmol) in Methanol (about 2 mL), Piperidine (about 5 µl) is added. After about 10 minutes, 7-(diethylamino)-2-oxo-2H-chromene-3-carbaldehyde (CCA) (about 20 mg, about 0.08 mmol) in DCM (about 2 mL) is added to above reaction mixture. It is stirred at about 50° C. under N2 atmosphere for about 3 hours. After completion of reaction, the solvent is evaporated. The crude product is purified using column chromatography on silica gel using compound in good yield of about 70%.

1H NMR (DMSO d6, 400 MHz); 13C NMR (DMSO d6, 100 MHz) δ 159.7, 156.7, 156.2, 152.6, 147.1, 143.4, 142.7, 139, 134.7, 131.3, 130, 127.4, 120.5, 119, 117.6, 113, 110.4, 108.5, 96.3, 44.4, 12.3; HRMS (ESI-MS): calcd for C25H25IN2O2 [M−I]$^+$ m/z=385.1911, found 385.1916 (FIG. 59).

Synthesis of Compound of formula II

Step-1

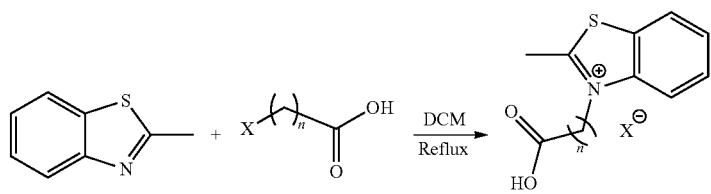

Step-2

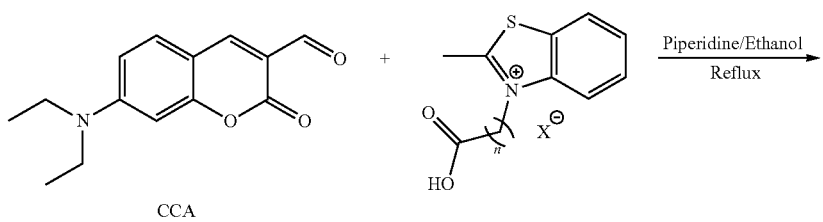

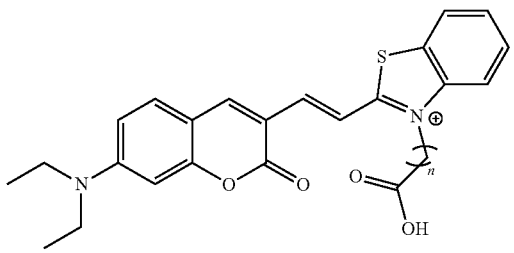

-continued
Step-3
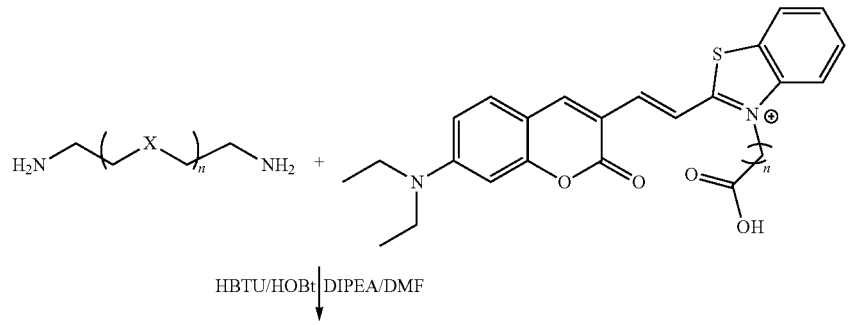
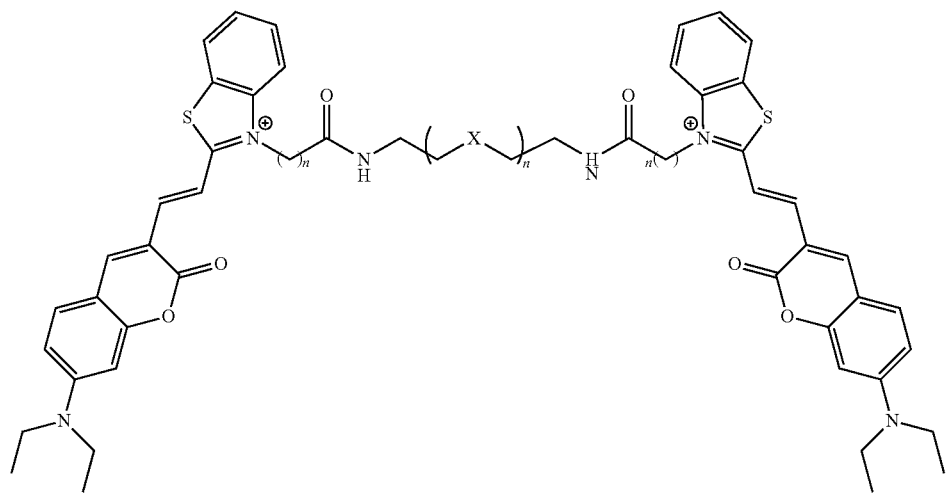
Synthesis of Compound of formula III
Step-1
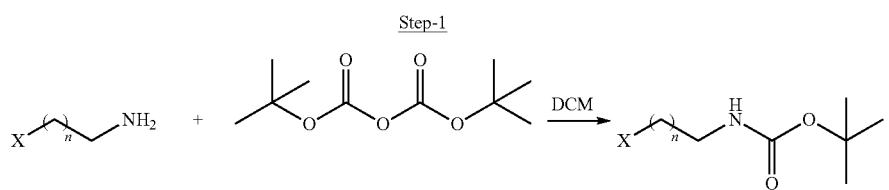
Step-2
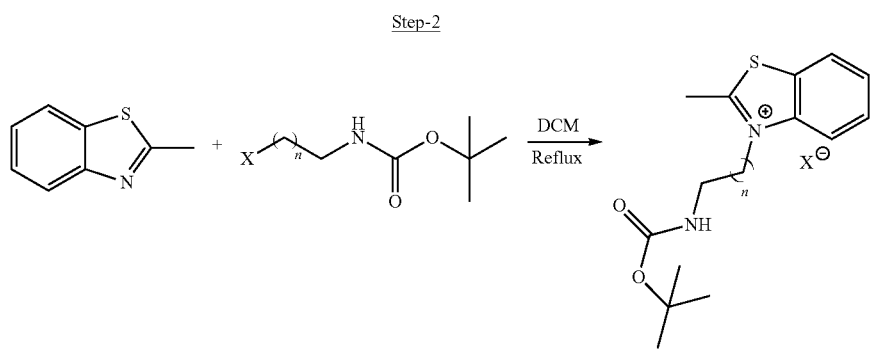

-continued
Step-3
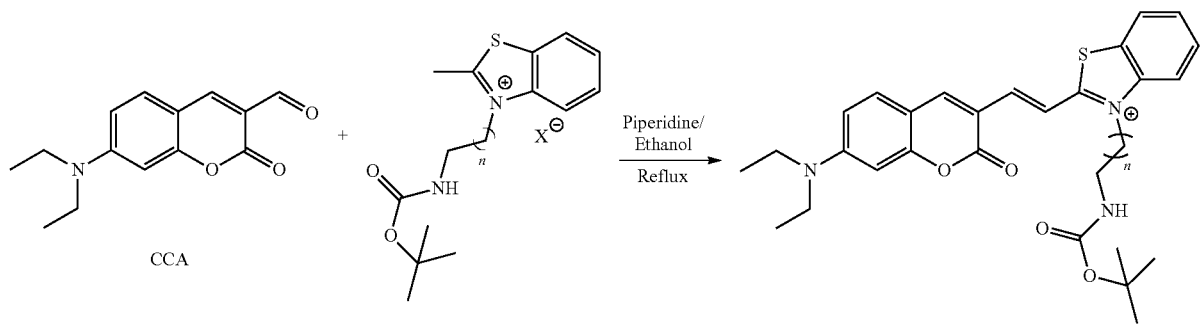
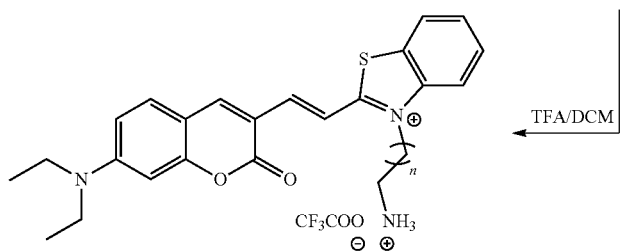
Step-4
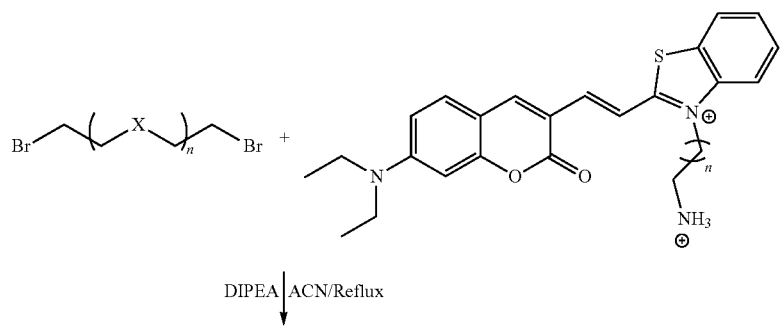
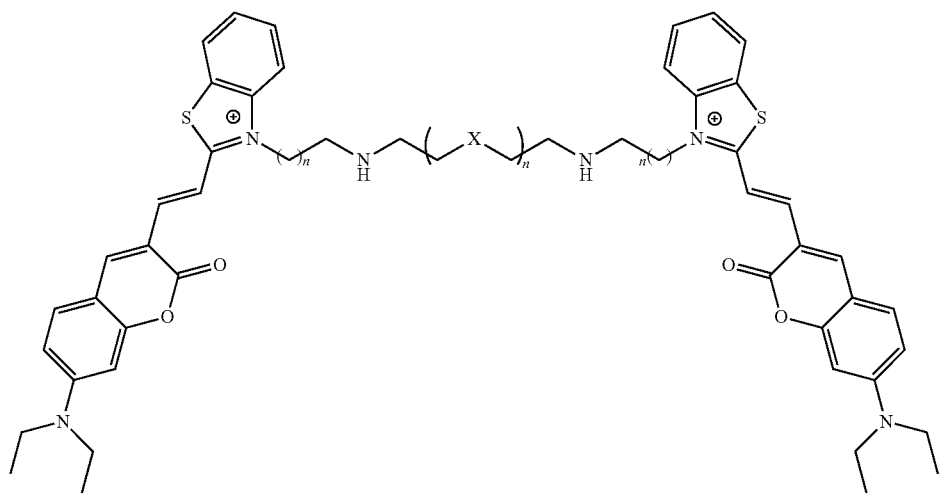

Synthesis of Compound of formula IV
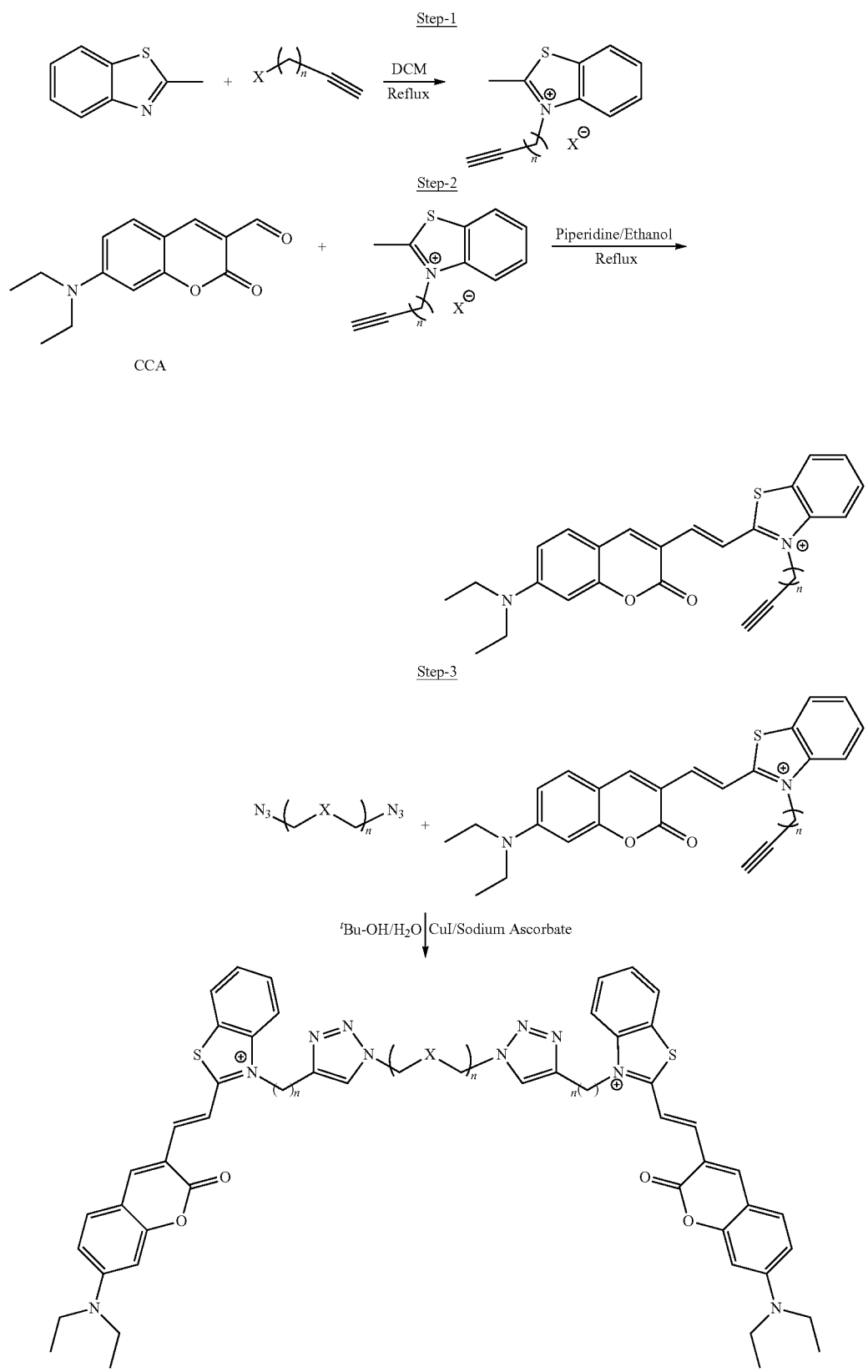

DNA Based Studies

Example 2: Molecular Interactions Studies

Molecular interactions of TC, CL and TP in the absence and presence of DNA through photophysical (absorption and emission) measurements in Tris-HCl buffer (100 mM, pH=7.4) solution are studied.

The samples for molecular interaction studies are prepared as per the standard parameters of Sample preparation for UV-Vis and Fluorescence-measurements of the present disclosure.

Figure 8:
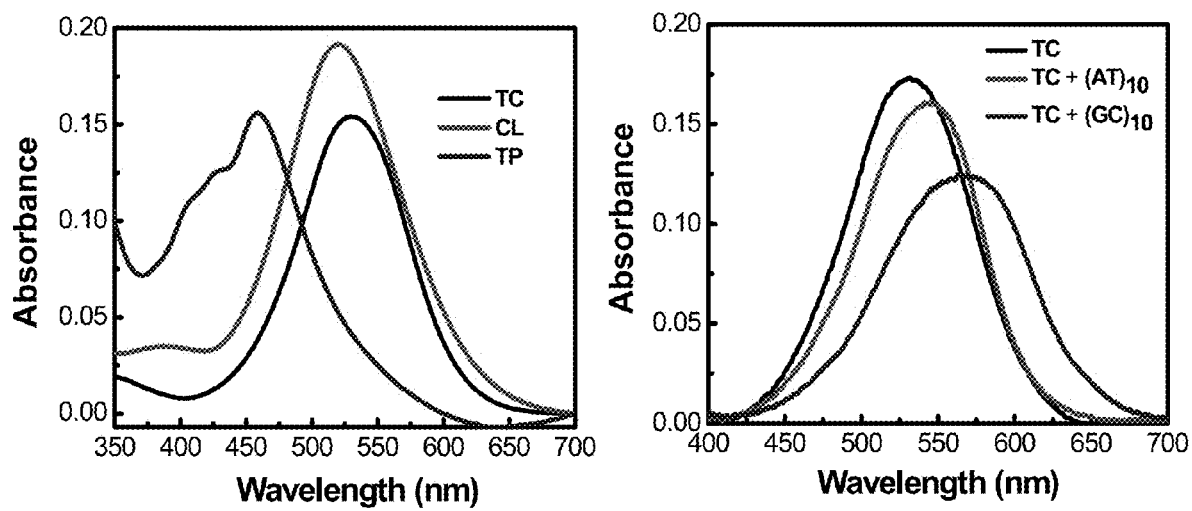
FIG. 8 depicts (A) UV-vis absorption spectra of probes (10 µM) TC, CL and TP in Tris-HCl buffer (100 mM, pH=7.4). (B) UV-vis absorption spectra of probe TC (10 µM) in the presence of $(AT)_{10}$ and $(GC)_{10}$.

Absorption Spectral Studies:

TC, CL and TP show absorption in the visible region with absorption maxima at 528, 519 and 460 nm respectively (FIG. 8a). Interestingly, the absorption spectrum of TC in the presence of dsDNA $(AT)_{10}$ shows bathochromic shift along with hypochromic shift (FIG. 8b), wherein the change in absorption maxima of probe TC before and after the addition of dsDNA $(AT)_{10}$ is $\Delta\lambda=14$ nm.

Figure 2:
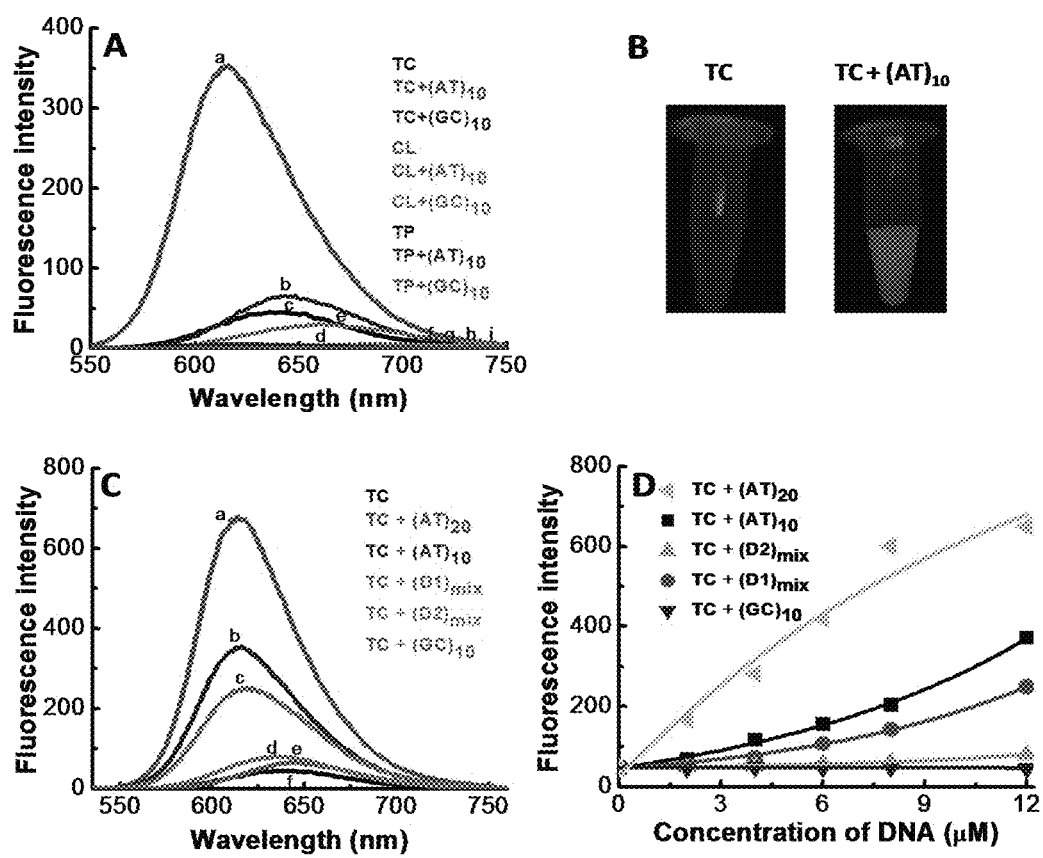

Emission Spectral Studies:

Emission spectra of TC, CL and TP show very weak fluorescence with maxima at 641, 689 and 623 nm respectively with large stoke shifts (FIG. 2A). Next, the emission spectra of probes in presence of dsDNAs [$(AT)_{10}$ and $(GC)_{10}$] are recorded. TC (10 µM) shows strong fluorescence enhancement in the presence of $(AT)_{10}$ as seen in FIGS. 2B and 2C, which further increases with the increase in DNA concentration (0 to 12 µM) with over all ~8 folds enhancement accompanied by hypsochromic shift ($\Delta\lambda=26$ nm) in the emission maxima at 616 nm (FIG. 2D). Further, it is observed that TC in presence of $(GC)_{10}$ does not show such fluorescence enhancement.

These fluorescence emission comparative studies of TC, CL and TP in presence of $(AT)_{10}$ and $(GC)_{10}$ clearly indicate these dyes as effective and selective switch-on fluorescent probes for DNA containing AT-base pairs. Furthermore, it is clear from the above results that the positively charged benzothiazole, conjugated N,N-diethylamino-coumarin fluorophore, balanced amphiphilicity, and possibility of achieving maximum π-electron overlap through molecular planarity (benzothiazole and coumarin) in a constrained environment makes the probes (TC, CL and TP) versatile AT-base pair selective DNA markers.

Figure 9:
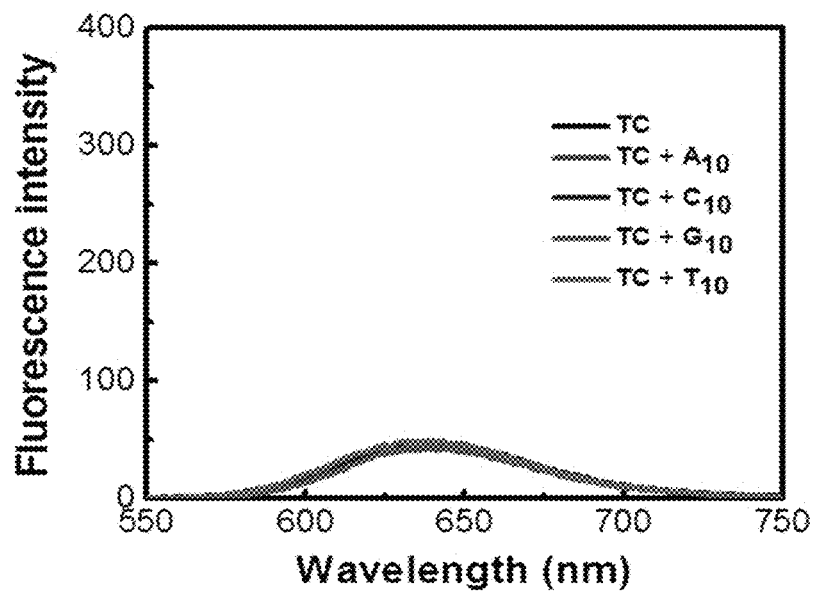
FIG. 9 depicts fluorescence emission spectra of TC (10 µM) in presence of ssDNAs $dA_{10}$, $dT_{10}$, $dG_{10}$ and $dC_{10}$ in Tris-HCl (100 mM, pH=7.4) buffer solution.

Furthermore, the probes (TC, TCE and TCP) do not show significant changes in the emission behaviour in presence of ssDNA oligonucleotides ($dA_{10}$, $dT_{10}$, $dG_{10}$ and $dC_{10}$) (FIG. 9 and FIG. 33). Overall, similar to probe TC, TCP and TCE show the selective fluorescence enhancement in presence of AT-rich sequences over ssDNA and GC-rich sequence (FIG. 33).

Therefore the selectivity of these dyes/probes for AT-region of dsDNA over ssDNA is a highly useful property considering the fact that most of the commonly employed staining dyes such as ethidium bromide, SYTO® 16 Green Fluorescent Nucleic Acid Stain, Picogreen I and SYBR® green I show weak fluorescence enhancement in presence of ssDNA sequences.

The remarkable switch-on fluorescence enhancement of TC, CL and TP only in presence of dsDNA containing AT-base pairs indicate AT-region provide favourable constrained environment to these probes by restricting their intramolecular twisting. This is verified by recording the emission spectra of TC with increasing glycerol percentage in Tris-HCl buffer solution. The emission spectra show an increase in fluorescence intensity with the percentage of glycerol content (FIG. 29). These results confirm that the origin of the fluorescence enhancement of probe TC in the presence of dsDNA containing AT-base pairs is due to the restriction of intramolecular twisting. The relatively high electropositive potential surface or unfavourable binding modes prevent the recognition of GC-regions of dsDNA by the probe TC. Overall, the preferential selectivity of TC for dsDNA with AT-base pairs over corresponding ssDNA or dsDNA containing only GC base pairs is ascribed to preferential binding of the probe to AT-region of DNA duplex.

All three hemicyanine probes i.e. TC, TP and CL are almost non-fluorescent in buffer solution (100 mM Tris-HCl, pH=7.4) with very low quantum yields (Table 1); this satisfies one of the primary requirements of a suitable switch-on fluorescence DNA binding molecular probe.

TABLE 1

The fluorescence quantum yields of probe TC, CL and TP in the absence and presence of DNA.

| Probe | $\Phi_F$ in Buffer | $\Phi_F$ with $(AT)_{20}$ | $\Phi_F$ with $(D1)_{mix}$ | $\Phi_F$ with $(GC)_{10}$ |
|---|---|---|---|---|
| TC | 0.03 | 0.36 | 0.11 | 0.04 |
| CL | 0.003 | 0.102 | 0.052 | 0.007 |
| TP | 0.002 | 0.042 | 0.026 | 0.005 |

Quantum yield of all the probes TC, CL and TP is measured in the absence and presence of dsDNAs in Tris-HCl buffer (100 mM, pH 7.4).

In the absence of dsDNA, TC shows very low quantum yield ($\Phi_F=0.03$), which shows a significant increase in quantum yield ($\Phi_F=0.36$) upon binding with $(AT)_{20}$. Of the three probes, TC, CL and TP, TC shows the best results although all three function as probes for detecting AT rich sequences on DNA.

Similar results for TCE and TCP, analogues of probe TC are seen in FIG. 31(A) and FIG. 31(B). Fluorescence spectra of TCE shows 5-fold enhancement in fluorescence in presence of (AT)10 and no appreciable change is observed in presence of (GC)10 (FIG. 31A). Fluorescence spectra of probe TCP shows 6-fold enhancement in presence of (AT)10 and no change in presence of (GC)10 (FIG. 31B).

Example 3: Sequence Selective Binding Affinity of Probe and Effect of Increasing Concentration of dsDNA The sequence selective binding affinity of TC towards various dsDNAs is studied in this example. Three different dsDNAs: $(AT)_{20}$, self-complementary mixed sequences $(D1)_{mix}$ and $(D2)_{mix}$ composed of variable number of consecutive AT-base pairs i.e., 20, 4 (two sets) and 2 (two sets) respectively are selected (FIG. 1). TC (10 µM) shows ~16 fold fluorescence enhancement with 20 consecutive AT-base pairs in $(AT)_{20}$ which is two orders of magnitude higher than $(AT)_{10}$. Further, emission spectra of probe TC in presence of $(AT)_{20}$ and self-complementary $d(AATT)_5$ DNA duplexes is recorded and the results are provided in FIG. 28, wherein, the fluorescence measurements of probe TC show ~16 folds enhancement in the presence of $d(AATT)_5$.

Figure 10:
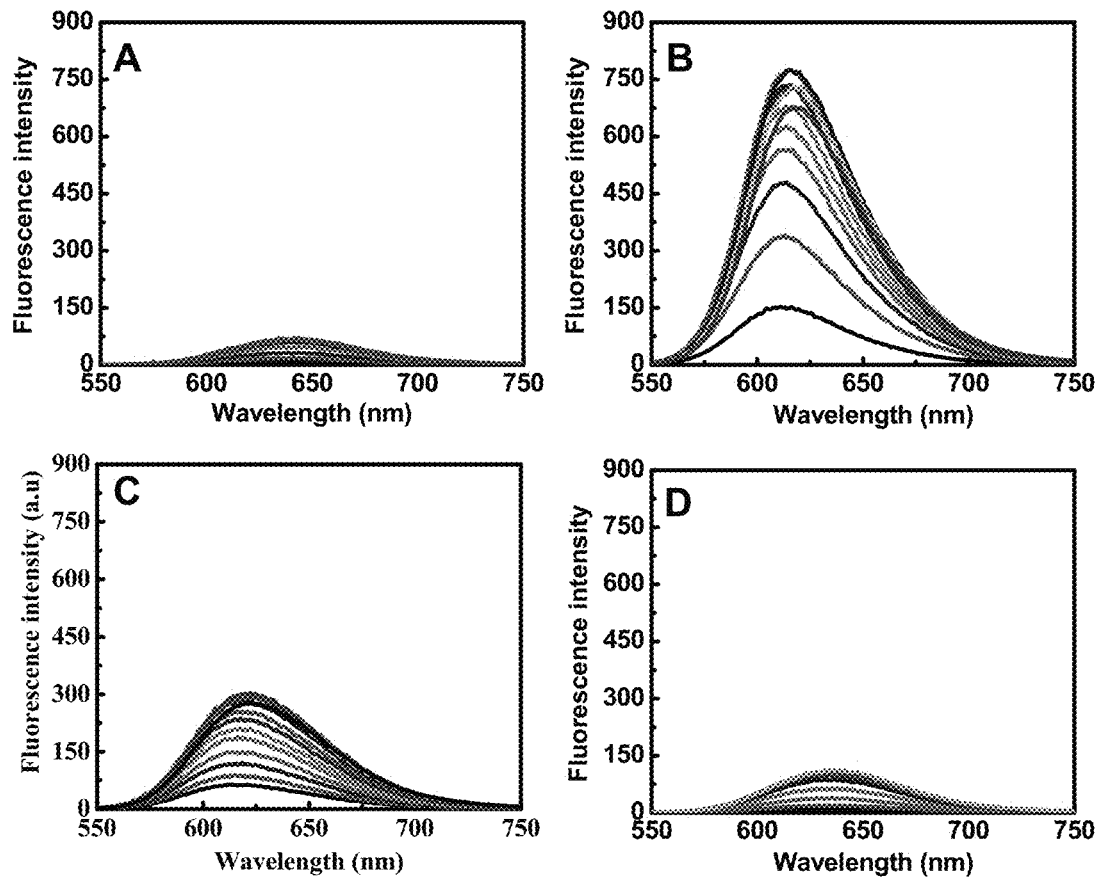
FIG. 10 depicts fluorescence spectra of duplexes with increasing concentration of probe TC. A) TC alone, B) $(AT)_{20}$, C) $(D1)_{mix}$ and D) $(D2)_{mix}$ upon excitation at 521 nm.

The mixed dsDNAs $(D1)_{mix}$ and $(D2)_{mix}$ with 4 (two sets) and 2 consecutive AT-base pairs (two sets) show fluorescence enhancement of ~6 and 1.5-folds respectively (FIG. 2C). These data are further validated by recording the emission spectra of TC (10 µM) with increasing concentrations (0 µM to 12 µM) of dsDNAs $(AT)_{20}$, $(AT)_{10}$, $(D1)_{mix}$ and $(D2)_{mix}$ which also show overall ~16, ~8, ~6 and ~1.5 fold fluorescence enhancement respectively with hypsochromic shift in the fluorescence maxima (FIG. 2D). Also, as seen from FIG. 10, with increasing concentrations of TC (1 µM to 20 µM), ~16-fold enhancement of fluorescence is observed in the presence of $(AT)_{20}$, ~6-fold enhancement of fluorescence is observed in the presence of $(D1)_{mix}$ and ~1.5-fold enhancement of fluorescence is observed in the presence of $(D2)_{mix}$. Similar results for absorption and fluorescence spectra of TCA in presence of $d(AATT)_5$ DNA, $(D1)_{mix}$ and $(D2)_{mix}$ is depicted in FIG. 40 and FIG. 41. The absorption spectra of TCA shows slight red shift in AT-rich d(AATT)5 and mixed (D1)mix and (D2)mix. The red shift in absorption spectra indicates the interaction between TCA and DNA-strands (FIG. 40). Similar to probe TC, fluorescence spectra of TCA shows the maximum fluorescence in presence of d(AATT)5 over (D1)mix and (D2)mix (FIG. 41).

Furthermore, the fluorescence response of TC in presence of calf-thymus DNA (ct-DNA) is also studied. As expected, TC (10 µM) in presence of ct-DNA (200 µg/mL) shows strong fluorescence enhancement (FIG. 30).

In general, above discussed studies reveal exponential fluorescence enhancement with increasing number of AT-base pairs in dsDNAs and preferential binding affinity of TC, analogues of TC i.e. TCE, TCP, TCA, TP and CL towards AT-sites than GC-sites. The dependency of fluorescence intensity of TC, analogues of TC i.e. TCE, TCP, TCA, TP and CL on AT-base pairs in dsDNA suggests the effectiveness of these compounds as fluorescence biomarkers for quantification of AT-regions of genome in a variety of cell lines and organisms.

Example 4: Concentration-Dependent Fluorescence Response

Figure 3:
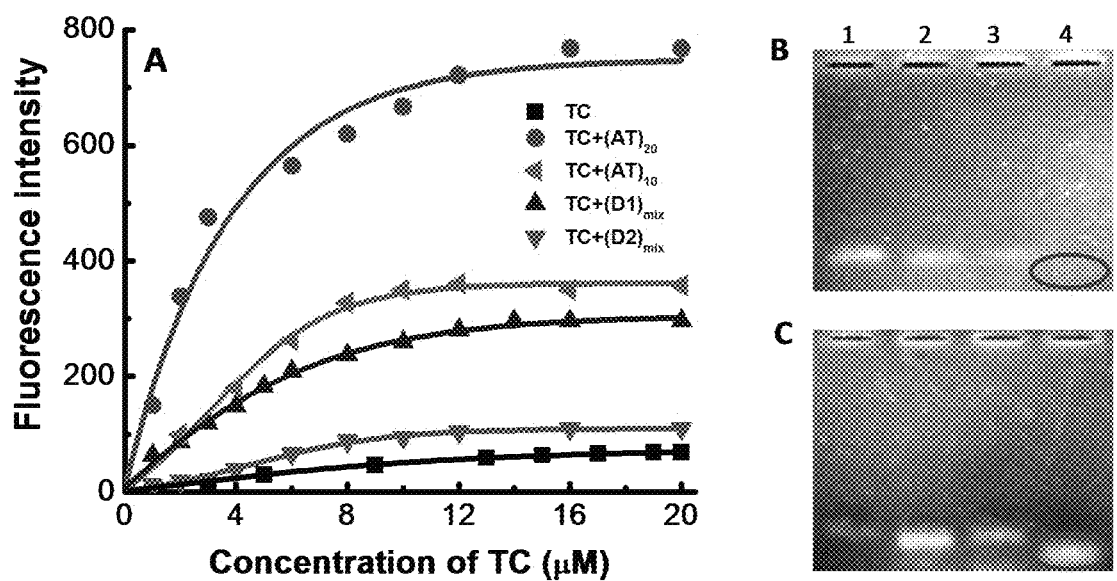
Figure 13:
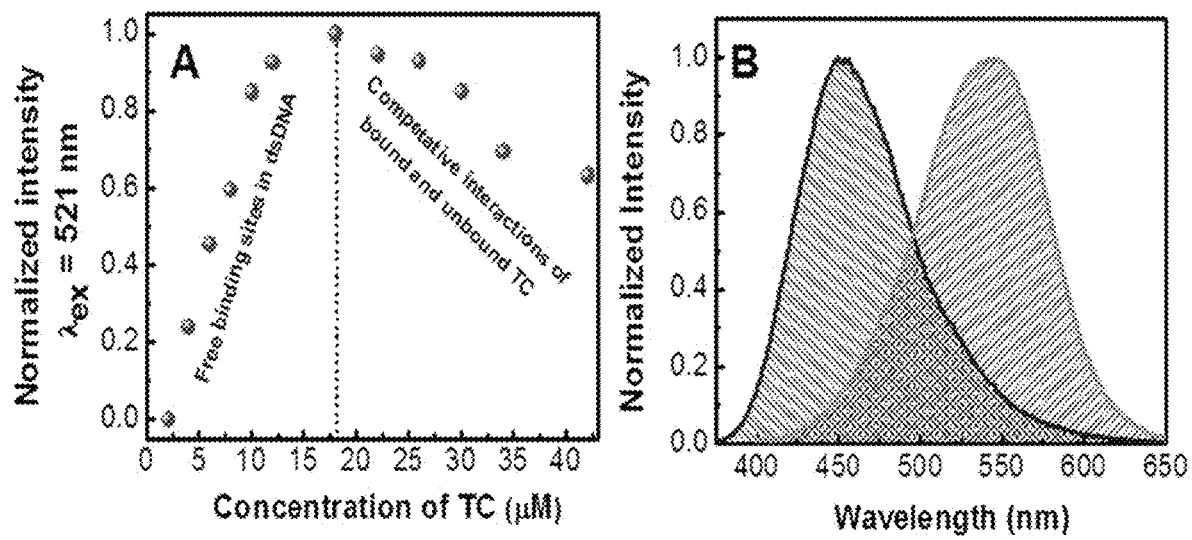
FIG. 13 depicts FRET-analysis of Hoechst+$(AT)_{20}$ complex with Probe TC. (A) Fluorescence dependence spectra of TC at 610 nm upon excitation at 521 nm of Hoechst (4 µM)+$(AT)_{20}$ with increasing concentration of TC. (B) Overlap spectra of emission of preformed Hoechst (4 µM)+$(AT)_{20}$ complex and absorption spectra of TC (10 µM)+$(AT)_{20}$ complex.

Concentration-dependent fluorescence response of TC against fixed concentration of dsDNAs (12 µM) containing AT-base pairs is studied (FIG. 3A). In the absence of dsDNA, increasing concentrations of TC (0 to 20 µM) do not show any appreciable changes in the fluorescence emission at 641 nm. In the presence of $(AT)_{20}$, increasing concentrations of TC from 0 to 18 µM show regular enhancement in fluorescence intensity while further increase in concentrations of TC (18 to 22 µM) result in fluorescence intensity reaching saturation (FIG. 3A). Interestingly, for concentrations of TC>24 µM, decrease in fluorescence intensity is observed accompanied by bathochromic shift in the emission maxima (FIG. 13A). Similar changes in the fluorescence emission are observed with increasing concentration of TC in presence of $(AT)_{10}$, $(D1)_{mix}$ and $(D2)_{mix}$ (FIG. 3A).

The observed fluorescence emission behaviour of TC suggests that at lower concentrations, TC can readily occupy the available binding sites (AT-region) of dsDNA which result in strong fluorescence enhancement. However, at higher concentrations of TC (18-22 µM), the fluorescence emission reaches maximum due to saturation of binding sites. After the saturation of binding sites (for >24 µM of TC) in dsDNA (12 µM), there will be competitive binding interactions between the unbound TC and bound TC molecules leading to displacement of some of the preoccupied TC molecules from dsDNA. This explains the linear increase in fluorescence at lower concentrations <18 µM, saturation at 18-22 µM and dramatic decrease in the fluorescence intensity at >24 µM of TC. Similarly, changes in fluorescence emission are observed with increasing concentration of TCP in presence of $(AT)_{10}$, $(D1)_{mix}$ and $(D2)_{mix}$ (FIG. 32). Further, with increasing concentration of probe TCP from 0 to 5 µM shows gradual increase in fluorescence of saturates at about 5 µM with fixed concentration of DNAs (FIG. 32).

Example 5: Comparative Selective Binding (Fluorescence Response) of TC with Ethidium Bromide and Propidium Iodide as a Gel Electrophoresis Staining Agent The use of TC as a staining agent for dsDNA in gel electrophoresis is studied in this example. The dsDNA samples (about 0.6 µg) of $(AT)_{20}$, $(D1)_{mix}$, $(D2)_{mix}$ and $(GC)_{10}$ are subjected to agarose gel electrophoresis and the gel is visualized under UV-illumination upon staining with TC. UV-illuminated gel-image shows strong fluorescence intensity for $(AT)_{20}$, $(D1)_{mix}$ and $(D2)_{mix}$ respectively, while the band for $(GC)_{10}$ is not stained by TC (FIG. 3B). Next, the agarose gel is stained with well-known gel-staining agent, ethidium bromide. Ethidium bromide is found to stain bands of $(D1)_{mix}$, $(D2)_{mix}$ and $(GC)_{10}$ on the gel, while the staining is very weak for $(AT)_{20}$ and strongest in case of $(GC)_{10}$, as expected from its weak affinity towards AT-region and stronger affinity for GC-region of dsDNA (FIG. 3C). From the gel-electrophoresis staining studies, it is clear that TC probe selectively discriminates dsDNA containing AT-base pairs from the DNA containing only GC-base pairs.

In addition, the comparative fluorescence response studies among TC, ethidium bromide (EtBr) (FIG. 11) and propidium iodide (PI) (FIG. 12) in the presence of $(AT)_{20}$ is also studied which clearly depict that TC is a much better staining probe for dsDNA when compared to EtBr and PI.

The above studies reveal and substantiate that TC is an excellent fluorescence marker while ethidium bromide (EtBr) and propidium iodide (PI) do not show appreciable fluorescence changes.

Example 6: Thermal Stability Studies of ds-DNA-TC Complex

In order to understand the thermal stability of dsDNA-TC complexes, temperature-dependent UV-vis absorption studies are carried out.

Figure 4:
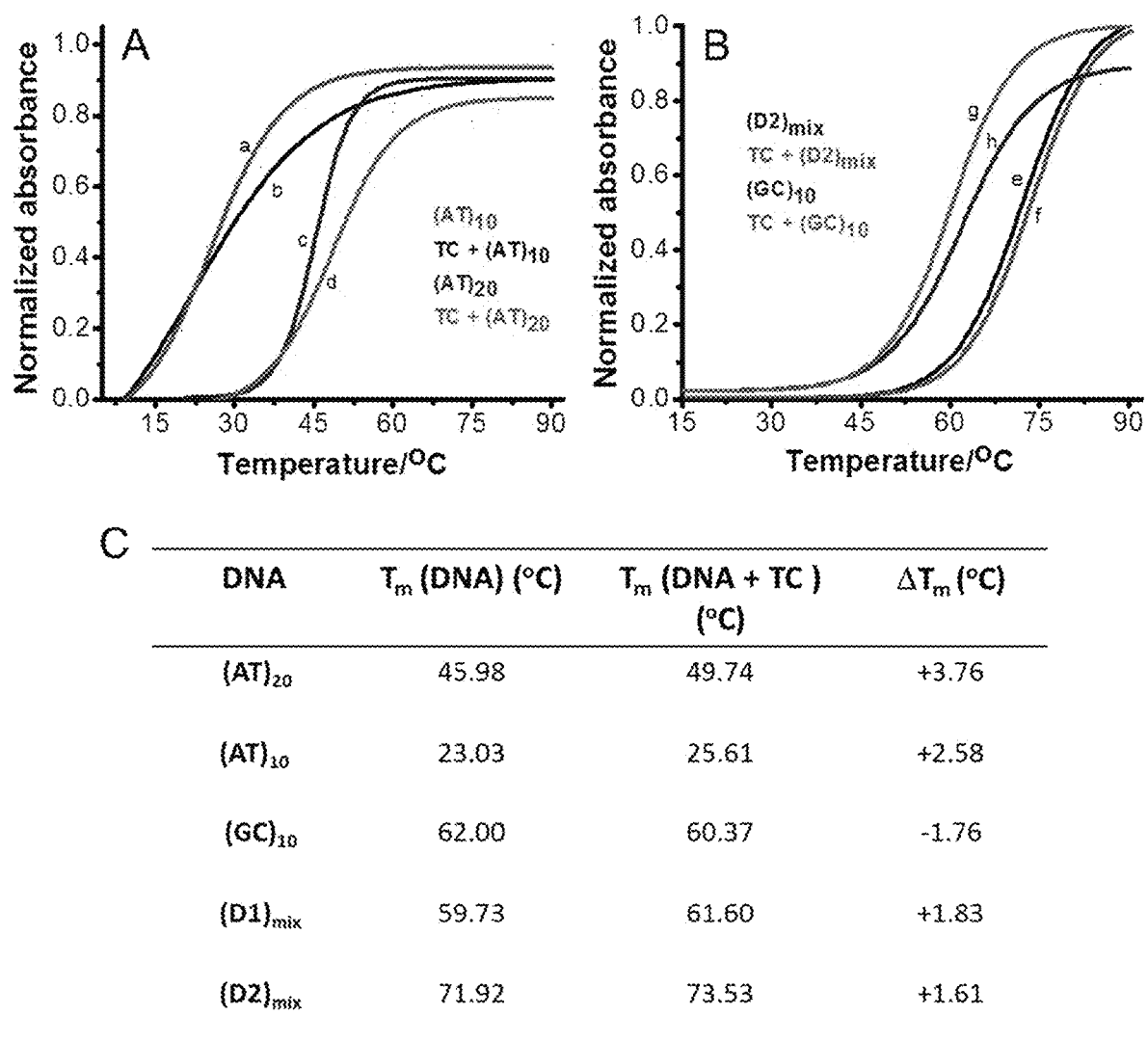

Thermal denaturation studies of double stranded DNA samples in the absence and presence of probe TC are recorded in the temperature ranging from about 10° C. to about 90° C. with heating rate of about 1° C./min (FIGS. 4 and 16). The variable temperature/wavelength mode is used. Absorption is monitored at about 260 nm of about 5° C. interval. Melting temperatures (Tm) of DNA samples are calculated from the first derivatives of the absorption vs. temperature curves (thermal denaturation or melting curves) obtained by monitoring at about 260 nm.

The UV-melting data of TC bound $(AT)_{20}$, $(AT)_{10}$, $(D1)_{mix}$ and $(D2)_{mix}$ show increased melting temperatures (Tm) with ΔTm=3.7, 2.5, 1.8 and 1.6° C. respectively compared to their unbound forms (FIG. 4). This enhanced thermal stabilization of AT-containing dsDNA by TC binding is an indicative of favourable interaction without any structural deformation in the duplex DNA structure. In contrast, melting study of $(GC)_{10}$ with the addition of TC shows decrease in Tm (ΔTm=−1.76° C.) which shows the destabilization of duplex DNA structure in presence of the probe. Overall, significant increase in Tm of TC bound dsDNA containing AT-base pairs and corresponding thermal destabilization in case of dsDNA containing only GC base pairs provides substantial evidence for preferential binding of TC to AT-base pairs region of DNA.

TABLE 2

Summary of melting temperatures (Tm) of all duplexes in the absence and presence of probe TC.

| dsDNA | $T_m$(DNA) (° C.) | $T_m$(DNA + TC) (° C.) | $\Delta T_m$ (° C.) |
| --- | --- | --- | --- |
| (AT)20 | 45.9 | 49.7 | +3.8 |
| (AT)10 | 23.0 | 25.6 | +2.6 |
| (GC)10 | 62.0 | 60.3 | −1.7 |
| (D1)mix | 59.7 | 61.6 | +1.9 |
| (D2)mix | 71.9 | 73.5 | +1.6 |

Example 7: Cellular Uptake or Cell Permeability of TC and Nuclear Staining Studies Effective cell permeability represents the cellular uptake of probe TC. Commonly used nuclear stains such as propidium iodide are not cell permeable. To stain cell nucleus with propidium iodide, usage of surfactants is required to break the cell membrane so that Propidium Iodide can easily enter the cells. On the contrary, probe TC does not require the use of surfactants as the dye is easily taken up by the cells.

The cellular uptake of TC and its application in nuclear DNA staining is studied as follows: HeLa S3 cell lines are incubated with probe TC and then imaged using confocal fluorescence microscopy (Carl Zeiss Laser Scanning Microscope (LSM510 META). HeLa S3 cells are excited at about 521 nm and the emission is measured at about 540-750 nm, corresponding to excitation of probe TC for selective binding of nuclear DNA.

Figure 5:
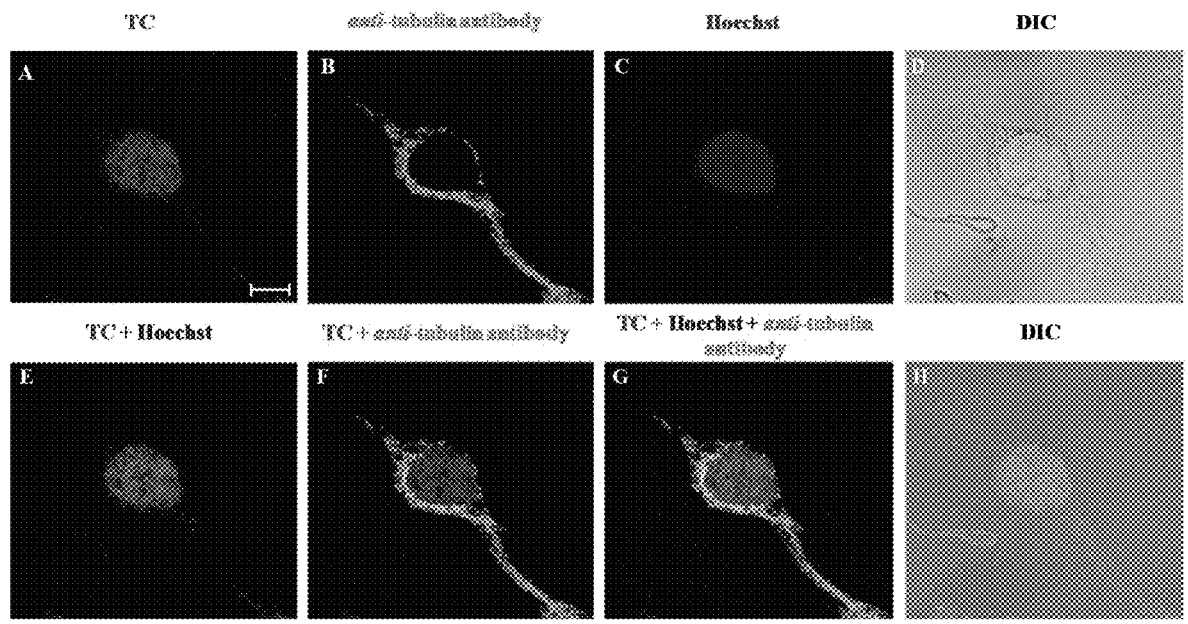

Fluorescence imaging of HeLa S3 cell lines with probe TC and co-staining with commercially available Hoechst 33258 nuclear stain shows selective targeting to the cell nucleus (FIG. 16). Further, nuclear staining studies in HEK293 cells with cytoplasmic marker α-tubulin are carried out to determine the specificity of probe TC to nuclei and not to the cytoplasm. Remarkably, it is found that probe TC does not co-localize with cytoplasmic marker α-tubulin (FIG. 5). These results further confirm the probe TC is selective towards nucleus in contrast to cytoplasm.

Example 8: Non-Specific Interaction Studies

One of the major problems with most of the DNA staining dyes is non-specific binding to cellular ribonucleic acids (RNA), proteins and other biomacromolecules. To study the non-specific interaction, emission spectrum of TC is recorded in presence of fetal bovine serum albumin (FBA) and it is observed that it does not show any detectable basal fluorescence of the probe (FIG. 17). This study confirms the base pair specific interaction of TC with dsDNA over proteins. To demonstrate the selectivity of TC for dsDNA over the RNA, the following test is performed: Deoxyribonuclease I (DNase I) and Ribonuclease (RNase) Digestion Studies in HEK293 Cell Lines.

DNase I is known to degrade nuclear DNA while RNase degrades RNA in the cytoplasm by catalyzing phosphodiester bonds cleavage.

HEK293 cells are fixed with chilled methanol for about 1 minute at room temperature and permeabilized with 0.1% Triton X-100 in PBS for about 2×5 minutes. After rinsing with PBS twice, for one set of experiments, cells are treated with probe TC (5 µM) for about 15 min at room temperature in three adjacent wells. A total of about 200 µL PBS (as control experiment), about 100 µg/mL DNase I (Sigma), or about 30 µg/ml DNase-Free RNase (GE) is added into the three adjacent wells and incubated at about 37° C. for about 2 hours. For another set of experiments, instead of treating with probe TC, cells are only treated with about 200 µL PBS (as control experiment), about 100 µg/ml DNase I (Sigma), or about 30 µg/mL DNase-Free RNase (GE) by adding into the three adjacent wells and incubating at about 37° C. for about 2 hours. Subsequently, cover slips for both the experiments are incubated with Hoechst 33258 at about 10 µg/mL for nuclear staining. After two more washes in PBS with 0.1% Triton X-100, the cover slips are washed in PBS, rinsed in ddH₂O and briefly dipped in 100% ethanol. After a quick dry, cover slips are mounted with 70% glycerol. Images are captured using a Carl Zeiss Laser Scanning Microscope (LSM510 META) using an equal exposure time for control, DNase I, and RNase experiments. Experiments are done in duplicate.

Figure 6:
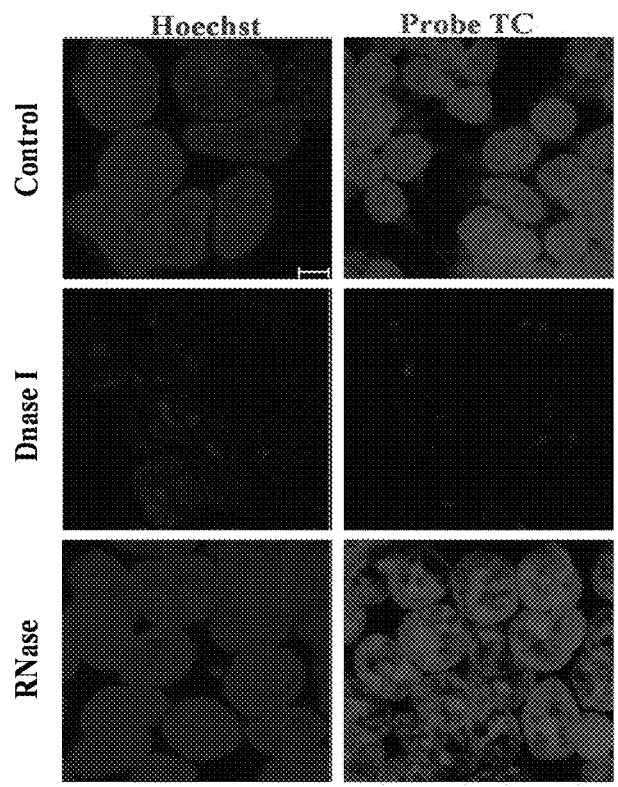

After DNase I digestion of cells, the fluorescence nuclear staining of probe TC (red) and control Hoechst 33258 (blue) are almost completely diminished from the nuclear region compared to untreated cells. On the other hand, it is observed that RNase digestion of HEK293 cells does not affect the fluorescence staining of TC and Hoechst 33258 in the nuclear region (FIG. 6). Therefore, all studies discussed above establish that probe TC is highly selective to DNA over RNA and proteins.

Example 9: Fluorescence and Gel-Electrophoresis Studies

Agarose gel-electrophoresis experiments are performed on custom made horizontal gel system using 3% agarose gel at about 100 V for about 1 hour at about 25° C. The dsDNA bands are visualized on the agarose gels by soaking in aqueous solution of TC or ethidium bromide for about 30 minutes.

HeLa S3 and HEK293 cells are grown on cover slip for about 24 hours in DMEM medium supplemented with 10% fetal bovine serum at about 37° C. in a humidified atmosphere containing 5% CO₂. Cells are fixed with 4% paraformaldehyde and permeabilized with 0.1% Triton X-100 in PBS for about 2×5 minutes. After rinsing twice with PBS, HEK293 cells and HeLa S3 cells are treated separately with probe TC (5 µM) for about 15 minutes at room temperature. After two washes in PBS, non-specific binding of antibodies is blocked with blocking buffer containing 10% FBS, 3% BSA, 0.1% Triton X-100. Subsequently, cover slips for HEK293 cells are incubated in primary antibody (a tubulin) at about 37° C. for about 30 minutes. After two washes in PBS with 0.1% Triton X-100, cover slips are incubated with secondary antibodies coupled with Alexa dye A488 at about 37° C. for about 30 minutes. Subsequently cover slips are incubated with Hoechst 33258 at about 10 µg/mL for nuclear staining. After two more washes in PBS with 0.1% Triton X-100, the cover slips are washed in PBS, rinsed in ddH₂O and briefly dipped in 100% ethanol. After a quick dry, cover slips are mounted with 70% glycerol. Images are captured using a Carl Zeiss Laser Scanning Microscope (LSM510 META).

Figure 7:
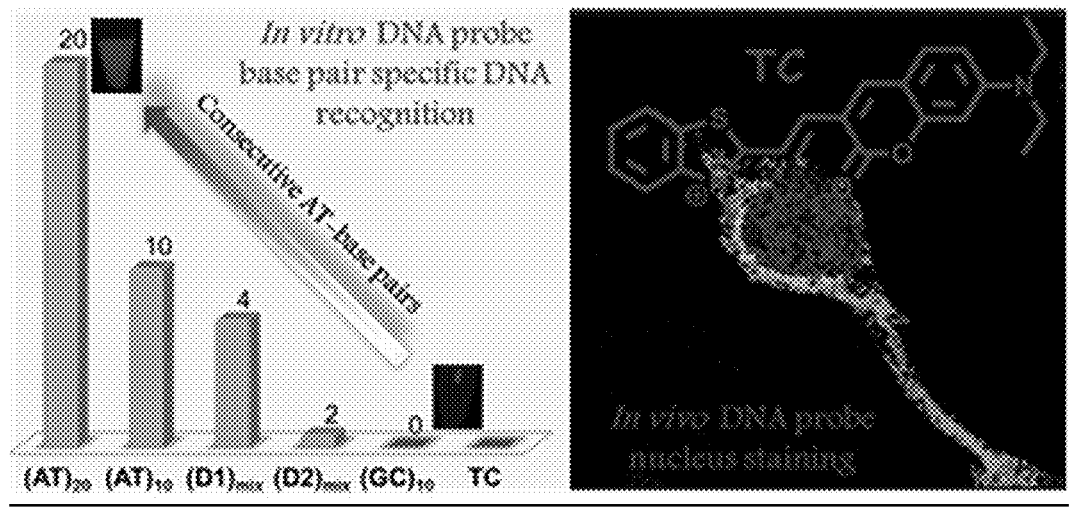

Fluorescence spectroscopy and gel-electrophoresis studies of TC show strong switch-on fluorescence enhancements in presence of DNA containing AT-base pairs while TC does not interact with GC-regions of DNA, single-stranded DNA, RNA and proteins. The exponential increase in fluorescence of TC as a function of consecutive AT-base pairs in dsDNA also suggests that AT-rich regions are the preferable binding sites. The fluorescence emission studies, live cell fluorescence-imaging in HeLa S3 and HEK293 cells, and nuclease enzymes digestion studies reveal AT-base pair specific fluorescence enhancement, non-toxicity, effective cell-permeability and selective nuclear DNA staining by TC over cytoplasmic region (FIG. 7).

Example 10: Cell Cycle Analysis

The fluorescence activated cell sorter (FACS) analysis using flow cytometry is a versatile tool for cell cycle analysis with the aid of DNA-specific binders. Probe TC is used for the cell cycle analysis of HEK293 cells using flow cytometry to quantitate DNA content in the cells. HEK293 Cells are harvested by trypsinization with 0.25% EDTA-Trypsin and collected by centrifugation at 2000 rpm for 3 min at 4° C. Cells are washed with 1×PBS twice. Then pellet is re-suspended in 200 µL of PBS and cells are fixed in 70% ethanol for 12 h at −80° C. PBS wash is given and again suspended in 1 mL of PBS. 6 µg of PI (6 µg of RNase for PI treated cells) and 6 µg of probe TC are added for staining (for 30 min) at 37° C. 10,000 cells are analysed by Flow cytometry (FACS aria instrument).

For FACS analysis, HEK293 cells are separately stained with Propidium Iodide (PI) and probe TC in the presence and absence of RNase respectively. FACS data shows the similar pattern of each cell cycle phase with almost similar percentage of populations of G1, S and G2-M (FIG. 26). These results suggest that probe TC binds only to DNA and can be used for FACS analysis to quantify DNA and cell cycle estimation without employing RNase. It is also observed that the intensity of probe TC is more as compared to same concentration of PI used at FL2-A scale. Additionally, cytotoxicity is a major limitation with DNA-binding probes including PI which leads to cell damage.

Example 11: Cytotoxic Studies of TC

To understand whether probe TC shows any cytotoxicity to HEK293 cells, MTT assay is performed as follows:

10,000 HEK293 cells are seeded in 96-well plate and cultured for about 12 hours. For dose-dependent experiment, cells are treated for about 30 minutes with about 2.5, 5 and 7.5 µM of probe TC and for time dependent set, about 5 µM of TC is used for about 6, 12, 18 and 24 hours treatment. Water is used as a control. About 20 µL of MTT (about 5 mg/mL) is added in each well, incubated for about 3 hours at about 37° C. and about 100 µL of DMSO is added. Readings are taken at about 570 nm in ELISA reader (VERSA Max microplate reader, Molecular Devices). The data is normalized with control and plotted with mean and standard error.

In dose dependent experiment, three different concentrations of probe TC are taken and it is observed that TC is non-toxic to HEK293 cells for treatment time intervals used (Here, the time intervals represents the amount of time i.e. about 30 minutes which is required to stain the HEK293 cells with probe TC) (FIG. 18A). Further, time dependent experiments for about 6, 12, 18 and 24 hours are performed by employing about 5 µM of TC. Time dependent experiments show gradual decrease in cell viability but dead cell percentage is very minimal and after about 24 hours of treatment, it is observed that about 64% of cells are viable (FIG. 18 B).

Example 12: Fret Studies

For the first time, the effective use of TC as Froster resonance energy transfer (FRET) probe for DNA in combination with other DNA binding dyes (X, suitable FRET pair) is demonstrated in this disclosure. FRET is the radiation-less transfer of the excitation energy of a donor fluorophore to an acceptor fluorophore. FRET is one of the most valuable tools used to measure the biological interactions, conformational changes of proteins and nucleic acids. FRET efficiency mainly depends on the appropriate spectral overlap between the emission spectra of donor and acceptor excitation spectra, the distance between the donor and acceptor, which should be less than ~10 nm and finally the dipole moments of donor emission and acceptor absorptions, which should not be perpendicular. The FRET study reveals that in presence of DNA, DNA binding dye (X) and TC becomes an efficient donor-acceptor pair. This FRET mechanism may also be used for Effective DNA recognition, base pair/sequence determination, drug designing, diagnostics and bio-inspired white light emitting systems.

Figure 14:
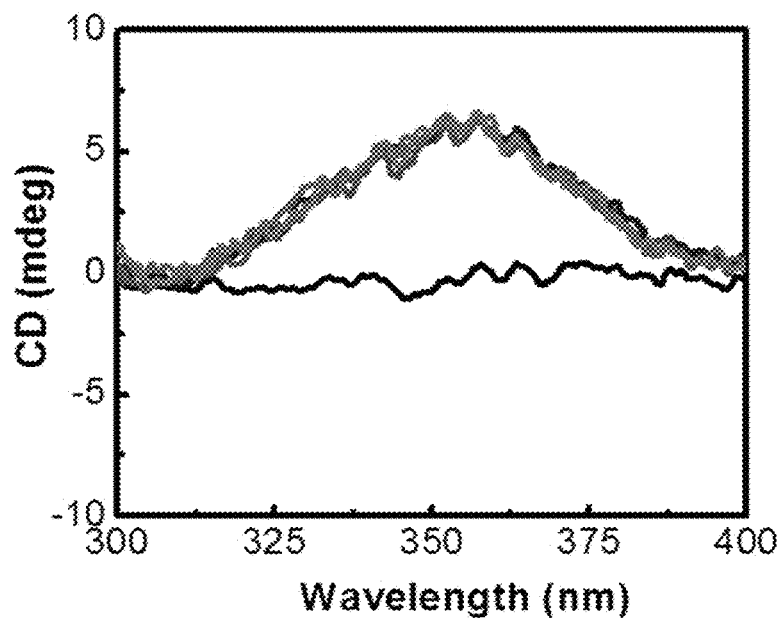
FIG. 14 depicts circular dichroism spectra of $(AT)_{20}$+Hoechst (4 µM) with increasing concentration of TC from 0 to 40 µM in Tris-HCl (100 mM, pH=7.4) solution.
Figure 15:
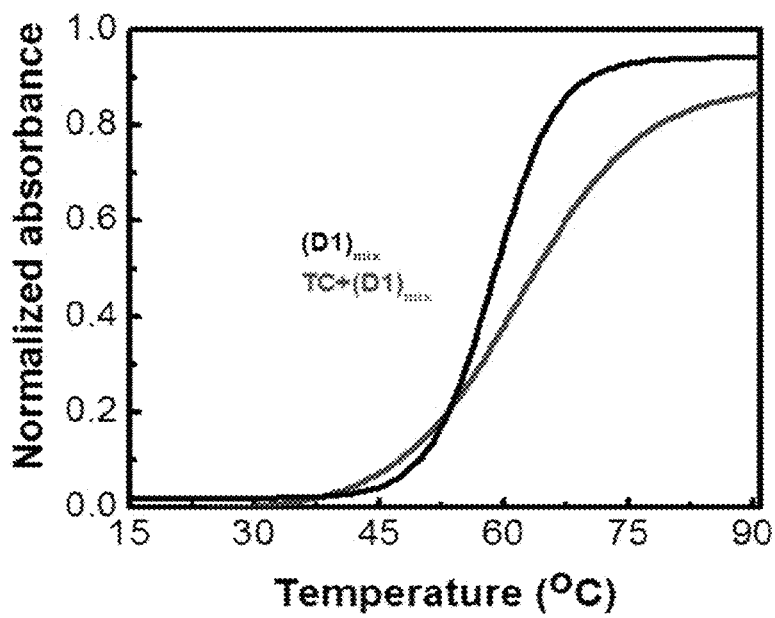
FIG. 15 depicts melting curves of (D1)mix in the absence and presence of TC.

To gain insights into preferential binding of TC to AT-base pair regions in dsDNA, competitive binding studies with Hoechst and DAPI are carried out. Hoechst dyes are known to interact in the minor groove of dsDNA. Firstly, the emission spectrum of preformed $(AT)_{20}$-Hoechst 33258 complex upon excitation at about 350 nm (corresponding to Hoechst) is recorded which shows fluorescence enhancement at about 450 nm (FIG. 19A). Next, the emission spectrum of preformed $(AT)_{20}$-Hoechst 33258 complex with increasing concentration of TC (about 0 to 40 µM) upon excitation at about 350 nm is recorded (FIG. 19B). A decrease in emission intensity of Hoechst at about 450 nm with increasing concentration of TC is observed. Simultaneously, there is a gradual increase in emission at about 610 nm of TC from about 0 to 20 µM and above this value, emission intensity reaches saturation (FIG. 19B). Interestingly, excitation at TC absorption (about 521 nm) shows strong fluorescence enhancement at about 610 nm with increasing concentration of the probe from about 0 to 20 µM which is specific of TC upon binding to dsDNA. This phenomenon of decrease in fluorescence intensity at about 450 nm (Hoechst) and corresponding increase in emission at about 610 nm (TC) upon exciting at about 350 nm (Hoechst) is due to efficient FRET from Hoechst to TC. Further increase in concentration of TC (about 20 to 40 µM) leads to decrease in fluorescence, a characteristic phenomenon where unbound excess probe (TC) assist the displacement of bound ones resulting in partial quenching of fluorescence (FIG. 13A). To understand this unprecedented fluorescence behavior observed in competitive study, circular dichroism (CD) studies of $(AT)_{20}$-Hoechst complex in presence of TC are carried out. CD-spectrum of $(AT)_{20}$ shows an intense positive and a negative Cotton signal in 200-300 nm region. Hoechst alone has no characteristic CD signal and in presence of $(AT)_{20}$ shows an induced positive Cotton signal in 300-400 nm region (FIG. 14). FIG. 14 depicts the circular dichroism spectra of probe TC in presence of preformed Hoechst:$(AT)_{20}$ complex. Upon increasing the concentration of probe TC, fluorescence spectra of Hoechst:$(AT)_{20}$ complex shows decrease in emission at 450 nm which corresponds to DNA bound Hoechst emission and increase in emission at 610 nm which corresponds to DNA bound TC emission (FIG. 19). From the observed spectral changes, it is presumed that the decrease in Hoechst is due to the displacement of bound Hoechst. To confirm this, the circular dichroism spectra of preformed Hoechst:$(AT)_{20}$ complex has been carried out with increasing of concentration of probe TC. Hoechst is achiral molecule hence, it does not show any CD-signal in 325-400 nm which corresponds to Hoechst absorption (325-400 nm). After complexation with DNA-minor groove, Hoechst shows the CD-signal in 325-400 nm due to interaction with the chiral environment which depicts in minor groove. It is known that the minor groove of dsDNA comprises of chiral environment and upon binding induces its chirality to achiral Hoechst. Surprisingly, no appreciable changes are observed in induced CD-signals of Hoechst (i.e., 325-400 nm) with increasing concentration of TC. Overall, CD-studies reveal that TC is not replacing the bound Hoechst from the preformed Hoechst:$(AT)_{20}$ complex. This also confirms that the decrease in fluorescence emission of Hoechst is due to the Fluorescence resonance energy transfer (FRET) between bound Hoechst and TC.

Normally, DNA duplexes exist in right handed helical conformation. They show the bisignated CD-signal in nucleobase absorption 200-300 nm region and they will not show any CD-signal in 325-400 nm region due to their inherent chiral sugar phosphate backbone. Hoechst is achiral molecule and hence, it does not show any CD-signal in 325-400 nm which corresponds to Hoechst absorption (325-400 nm). After complexation with DNA-minor groove, Hoechst shows the CD-signal in 325-400 nm due to interaction with the chiral environment which depicts in minor groove). It is known that the minor groove of dsDNA comprises of chiral environment and upon binding induces its chirality to achiral Hoechst. However, increasing concentration of TC (about 0 to 40 μM) does not show any detectable change in the CD signal of $(AT)_{20}$-Hoechst complex. These data reveals that TC is not competing with Hoechst for binding site in the minor groove of dsDNA, but rather binds cooperatively at nearby site of AT-base pairs region (FIG. 14). This is evident by the effective FRET from Hoechst (donor) to TC (acceptor). Normally, the efficient energy transfer in FRET mechanism depends on distance between donor-acceptor pair and proper overlap of emission of donor and absorption of acceptor. The effective spectral overlap of emission of Hoechst and excitation of TC indicates perfectly matched donor-acceptor pair for FRET process in AT-rich DNAs (FIG. 13B). Thus, the observed FRET between the two probes clearly suggests that the binding site for TC must be in close proximity to Hoechst in the AT-rich minor groove of dsDNA. In the present disclosure, FRET is also observed between DAPI (donor) and TC (acceptor) in presence of dsDNA containing AT-base pairs (FIG. 27).

In conclusion, the present disclosure provides highly AT-selective red fluorescent hemicyanine-based thiazole-coumarin (TC) and related compounds probe for sequence-specific recognition of dsDNA.

Example 13: Comparison of TC with Propidium Iodide (PI), Ethidium Bromide (EtBr), DAPI and Hoechst The major advantages of probe TC are: longer excitation/emission wavelengths (which avoids the cell damage due to the UV-light absorption commonly observed with probes like DAPI and Hoechst dyes, and auto-fluorescence from the cellular organelles and biomolecules), larger stoke shift (this provides additional advantage that avoids the self-absorption of higher energy part of their emission, useful in FRET and BRET based assays), good cell permeability (this is the major limitation of existing probes like propidium iodide, TO-PRO-dyes), non-toxicity (toxicity is the major limitation of NIR-fluorescence probes like DRAQ5 probe) and specific staining (commonly observed with SYTO and other dyes are non-specific in nature). Many commercial/reported dyes in literature are known to bind single stranded DNA, RNA etc. The probe TC is highly specific to double stranded DNA. For better comparison, the fluorescence enhancement of TC is compared with commercial DNA staining dyes such as Ethidium bromide (EtBr) and propidium iodide (PI) in presence of AT-DNAs. In presence of AT-rich DNA, TC is a better probe than EtBr and PI which are highly toxic to cells. These advantages make the probe TC superior for cell imaging studies.

Table 3 below depicts the comparison of the probe TC against commercial probes like DAPI, Hoechst, Ethidium bromide, and Propidium iodide in terms of selectivity, fluorescence, cell permeability and toxicity.

| Dyes | Selectivity | Fluorescence maxima free/DNA bound dye (nm) | Fluorescence qauntum yield ($\Phi_F$) DNA bound dye | Cell permeability | Toxicity |
| --- | --- | --- | --- | --- | --- |
| DAPI | AT rich | 496/450 | $0.42^a$ | Semi-Permeable | Non-toxic |
| Hoechst33258 | AT rich | 490/450 | $0.34^a$ | Permeable | Non-Toxic |
| Ethidium bromide | — | 624/602 | $0.35^a$ | Impermeable | Toxic |
| Propidium iodide | — | 646/617 | $0.13^a$ | Impermeable | Toxic |
| Probe TC | AT-rich | 641/610 | $0.36^b$ | Permeable | Non-Toxic |

It is seen from the above table that, Probe TC of the instant disclosure is highly selective towards AT rich regions on, has good fluorescence property, is permeable and non-toxic at the same time. Thus, it is evident that the TC probe of the instant disclosure has comparatively high efficacy when compared with the dyes known in the prior art.

Figure 11:
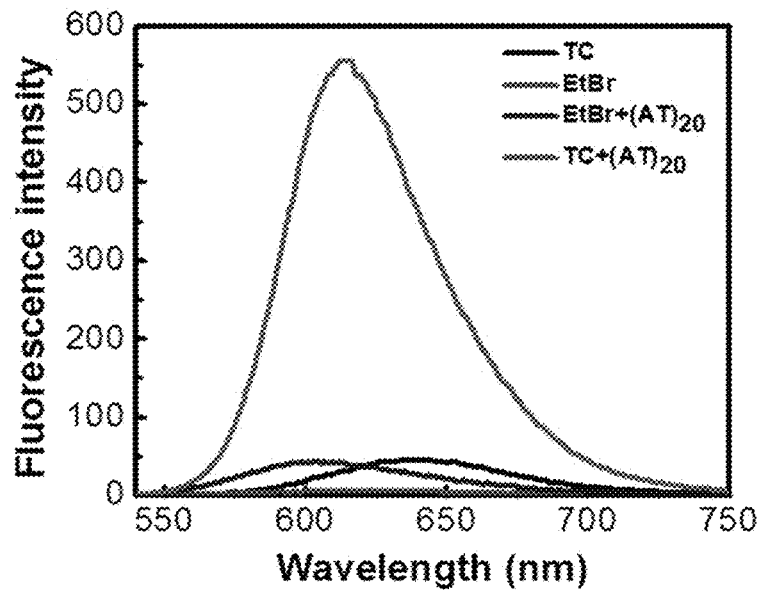
FIG. 11 depicts fluorescence emission spectra of probe TC (10 µM) and Ethidium bromide (EtBr) (10 µM) in presence of $(AT)_{20}$ in Tris-HCl buffer (100 mM, pH=7.4).
Figure 12:
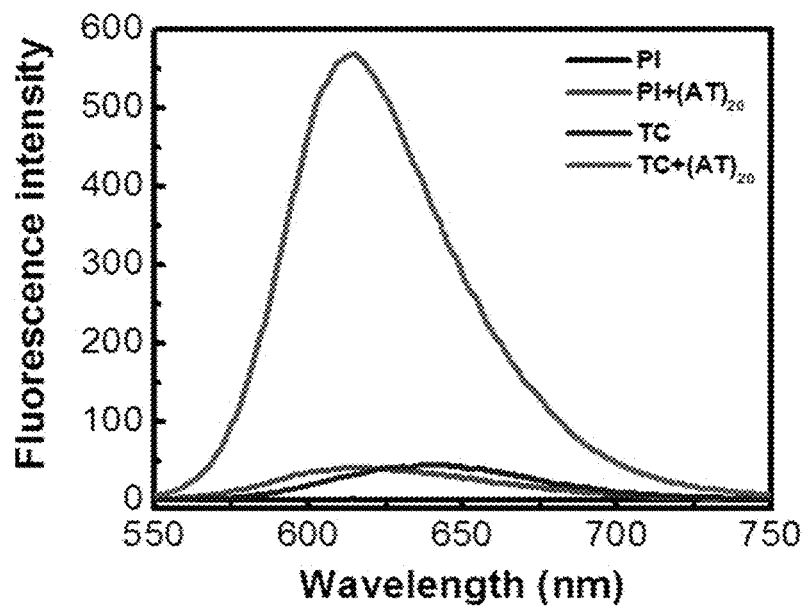
FIG. 12 depicts fluorescence emission spectra of probe TC (10 µM) and Propidium iodide (PI) (10 µM) in presence of $(AT)_{20}$ in Tris-HCl buffer (100 mM, pH=7.4).

The major advantages of the probes of the instant disclosure are longer excitation/emission wavelengths (which avoids the cell damage due to the UV-light absorption commonly observed with probes like DAPI and Hoechst dyes, and auto-fluorescence from the cellular organelles and biomolecules), larger stoke shift (this provides additional advantage that avoids the self-absorption of higher energy part of their emission, useful in FRET and BRET based assays), good cell permeability (this is the major limitation of existing probes like propidium iodide and ethidium bromide), non-toxicity and specific staining to dsDNA. For better comparison the fluorescence enhancement of TC is compared with commercial DNA staining dyes such as Ethidium bromide (EtBr) and propidium iodide (PI) in presence of AT-DNAs (FIGS. 11 and 12). In presence of AT-rich DNA, TC is a better probe than EtBr and PI which are highly toxic to cells. These advantages make the probes of instant disclosure superior for cell imaging studies.

Example 14: Simulation Studies of Probe TC Binding to dsDNA

To gain greater insights into the binding mode and preferential fluorescence enhancement in AT-rich over GC-rich regions of dsDNA, ab initio Density Functional Theory (DFT) calculations of probe TC in the absence and presence of dsDNA is carried out. Each molecule is optimized with the help of DFT, and their photophysical properties are calculated using time-dependent DFT (TD-DFT) as implemented in Gaussian 09 package. For the optimization, vb97XD exchange correlation functional is used to include empirical dispersion while for TD-DFT calculations B3LYP exchange and correlation functional is employed. 6-31 g(d) basis set is used for all the atoms. The DNA phosphate backbone is neutralized by protonating one of the oxygen atoms of the phosphate groups, which does not alter any property of the DNA duplex structure. The DFT and TDDFT calculations are performed with surrounding water, using a Polarized Continuum Model (PCM) to include the solvent (water) effect. To predict the interaction mode and relative binding affinity of probe TC, the stabilization energies of TC is estimated in presence of AT- and GC-base pairs in all possible modes. The optimized structures show that intercalation is the most preferred binding mode for TC (FIG. 39B). FIG. 39 B represents the interaction bind mode of probe TC in presence of AT and GC base pairs. Intercalation binding mode is an entropically driven process in which a flat aromatic compound (TC) is inserted between the base pairs through the dipole-dipole and π-stacking interactions and the positively charged benzothiazole interacts with phosphate backbone and enhances the stability. Studies also reveal that TC is stabilized more strongly by AT-base pairs (37.65 kcal mol21) than by GC-base pairs (34.98 kcal mol21). These energy values support the observed moderately-increased melting temperatures of AT-rich DNAs over GC-rich DNAs in the presence of probe TC. To predict the preferential fluorescence enhancement of probe TC in AT-base pair regions over the GC-base pairs, the absorbance and emission spectra are calculated using optimized ground state (S0) geometry and optimized first excited state (S1) geometry, respectively. The TD-DFT calculation provides excitation energies and oscillator strengths to the lowest singlet states (Table 4).

TABLE 4

Calculated absorption/emission transition with corresponding oscillator strength of TC, TC@2AT and TC@2GC.

| Compound | Transition | Excitation energy (nm) | Oscillator Strength |
|---|---|---|---|
| TC | Absorption | 507.13 | 1.67 |
|  | Emission | 599.02 | 2.07 |
| TC@2AT | Absorption | 514.11 | 0.89 |
|  | Emission | 598.75 | 1.84 |
| TC@2GC | Absorption | 564.91 | 0.19 |
|  | Emission | — | — |

FIG. 39 A depicts that the Frontier Molecular Orbitals (FMOs) of TC, TC@2AT and TC@2GC in their ground state (S0) and Excited State (S1). In case of TC and TC@2AT complexes, the HOMOs and LUMOs are localized on the TC moiety for both absorption and emission. It is found that for all the possible modes, the lowest energy transitions occur from Highest Occupied Molecular Orbital (HOMO) to Lowest Unoccupied Molecular Orbital (LUMO). For both TC and TC@2AT complexes, the HOMOs and LUMOs are localized on the TC moiety for both absorption and emission. It is interesting to note that, in case of the TC@2GC complex for absorption, the corresponding MOs (HOMO and LUMO) are localized on the TC moiety, but for emission, the transition occurs from the TC moiety to the guanine moiety of TC@2GC (FIG. 39A), which quenches the fluorescence emission. In fact, in the latter case, the fluorescence quenches because of charge transfer. This clearly depicts the non-fluorescence nature of TC in presence of GC-base pairs is due to energy transfer from TC moiety to Guanine moiety.

Example 15: Preferential Fluorescence Staining of Malaria Parasites with the Compounds of the Present Disclosure The strong and specific binding of probe TC towards the AT-rich DNA raises the possibility whether this probe can be used for purposes other than mammalian nuclear staining and cell sorting. To test this possibility, *Plasmodium falciparum* is selected as a model system which has AT rich genome (80%). The parasites are incubated with low concentrations of probe TC (about 1 mM and about 2 mM) with trophozoite stage parasites growing in erythrocytes. Live fluorescence imaging of trophozoite stage parasites depicts that probe TC specifically binds to the parasite cells within the red blood cells at about 1 mM and about 2 mM concentrations. Vehicle control (water) does not show any detectable fluorescence under similar experimental conditions (FIG. 38). Incubation of the HepG2 cells (human liver cancer cells) with about 2 mM of probe TC does not show any detectable fluorescence FIG. 44. These results clearly indicate that probe TC preferentially binds to the AT-rich genome of the parasite at very low concentrations. Collectively, these results suggest the selectivity of probe TC for preferential staining of malarial parasites in human erythrocytes, indicating that probe TC is a potential diagnostic tool for detecting malarial parasites in a sample.

Thus, the AT-selective red fluorescent DNA probes of the present disclosure (Compounds of Formula I, their dimers, compound of formula V, compound of formula VI and its isomer (compound of formula VII)) are promising biomarkers in molecular biology and immunohistochemistry and are viable molecular tools in fluorescence spectroscopy, flow cytometry, DNA quantification and inspire discovery of genome-specific binders of potential therapeutic interest.
Applications:
  Compounds of Formula I, their dimers, compound of formula V, compound of formula VI and its isomer (compound of formula VII) are used as fluorescence binding markers for biomolecules like DNA.
  These fluorescence dyes are useful for sequence specific recognition of dsDNA in treating gene-related human diseases especially cancer (see FIG. 74), parasitic and viral infections
  The intrinsic fluorescence property of these dyes makes them a versatile fluorescence marker for molecular biology and immunohistochemistry, fluorescence spectroscopy and microscopy, flow cytometry and DNA quantification applications.
  Choosing suitable donors lead to the formation of efficient FRET-pairs which are useful for monitoring the conformational changes in nucleic acids and proteins.
  Use of the dye for the development of genome-specific binders of theranostic interest in conjugation with designed oligonucleotides.
  AT-selective probes are of particular interest in mapping AT-stretches which are found in critical regions such as replication origins, minisatellite centromeric regions and for the detection of AT-rich regions which are involved in chromatin remodeling associated to senescence and tumorogenesis. The probes of the instant disclosure are used for chromosomal staining and quantitation of AT-regions of genome in a variety of cell lines and organisms (FIG. 45).

The fluorescence activated cell sorter (FACS) analysis using flow cytometry is a versatile tool for cell cycle analysis with the aid of DNA-specific binders. Although FACS-analysis shows that outcome is same as propidium iodide, propidium iodide use requires the cells to be treated with RNase whereas RNase is not required/added when the probes of the instant disclosure are used. Moreover, number of cells effectively counted is more in case of probe TC compared to propidium iodide (FIG. 27). Therefore the probes of the instant disclosure are better probe than propidium iodide both in terms of toxicity and number of cells counted effectively.

Aβ Aggregate Based Studies
Standard Parameters
Materials and Methods

All reagents or solvents are obtained from sigma Aldrich and used without further purification. All air and moisture sensitive reactions are carried out under an argon atmosphere. Absorption spectra are recorded with Perkin Elmer Model Lambda 900 spectrophotometer. Fluorescence spectral measurements are carried out by using Perkin Elmer Model LS 55 fluorescence spectrophotometer. Incubation for fibril formation is performed in the Eppendorf Inova42 incubator.

Microscopy:

The processed samples are imaged using Delta Vision Elite (Applied Precision) live cell imaging microscopy. The filters FIQC, TRIQC and POL are used. The excitation CWL/BP and emission CWL/BP for various filters used viz. 490/20 and 529/38(FIQC), 542/27 and 594/45(TRIQC). Images are collected as Z-scans, de-convolved and processed using Delta Vision software (softWoRx).

Preparation of Aβ$_{42}$ Fibrils:

Aβ$_{42}$ peptide (0.25 mg) (Merck, calbiochem) is dissolved in hexafluoro-2-propanol (HFIP, 0.2 mL) and incubated at room temperature for 1 h. HFIP is then removed by a flow of nitrogen and further dried by vacuum. HFIP-treated Aβ$_{42}$ is then dissolved in DMSO to a final concentration of 1 mM and diluted to 200 μM with 10 mM PBS (pH 7.4). The solution is incubated at 37° C. for 48 hours with gentle and constant shaking. The formation of Aβ42 fibrils is confirmed by Thioflavin assay.

Preparation of Amylin (IAPP) Fibrils:

A 0.1 mg (Merck, calbiochem) sample of amylin is dissolved in 100 μL of acetonitrile to disrupt any pre-existing aggregates, and taken up in 200 μL of 10 mM PBS buffer, pH 7.4. The final concentration of acetonitrile in the fibrillization buffer is 10% (v/v). The solution is sonicated continuously for 1 minute to break up any potential aggregates. To form fibrils, the sample is incubated at 37° C. without agitation in an eppendorf tube for 120 hours (5 days).

Preparation of α-Synuclein Fibrils:

α-Synuclein peptide (0.5 mg) (Sigma Aldrich) is dissolved in hexafluoro-2-propanol (HFIP, 0.2 mL) and incubated at room temperature for 1 hour. HFIP is then removed by a flow of nitrogen and further dried by vacuum. Then α-Synuclein peptide is dissolved in TBS buffer to a concentration of 200 μM. Then the solution is incubated at 37° C. for 3-5 days with constant shaking at 150 rpm.

Calculation of Partition Coefficient (Log P):

Log P value is calculated by Shake flask (or tube) method. To an equilibrated solution of n-octanol and water in a separating funnel, probe QC/TC is added and agitated well. The solution is left for 30 minutes for proper separation of immiscible solvents, then the distribution of QC/TC is calculated using UV spectroscopy and the obtained concentrations are used in below equation to obtain log P value log $P$=log [Conc. of QC or TC in n-octanol/Conc. of QC or TC in water]

Measurement of the Binding Constant of QC/TC for of Aβ Aggregates In Vitro:

A mixture containing Aβ$_{42}$ aggregates (2 μM) is titrated with increasing concentration of probe QC/TC (0-1.15 μM) and fluorescence intensity at 639 nm is recorded ($\lambda_{ex}$=537 nm). The $K_d$ binding curve is generated by GraphPad Prism 5.0 (GraphPad Software, Inc., La Jolla, Calif., USA).

$Y=B_{max}*X/(K_d+X)$ $B_{max}$ is the maximum specific binding in the same units as Y.

$K_d$ is the equilibrium binding constant.

Quantum Yields Determination:

Florescence Spectra are measured in 1 cm quartz cuvettes with spectroscopic grade solvents. Cresyl violet perchlorate in ethanol (φ=0.54) is used as the standard for the fluorescent quantum yield calculation using the absorption of the test sample. The emission spectra area is obtained from 550-800 nm. Dilute solutions ($10^{-6}$ M) are used to minimize reabsorption effects. Fluorescence measurement are made three times for each dye and averaged. Quantum yields are determined using the following equation:

For QC:

$\phi_{QC}=\phi_{stand}(F_{QC}/F_{stand})\times(A_{stand}/A_{QC})\times(n_{QC}^2/n_{stand}^2)$ φ=Quantum yield, F=Area under fluorescence spectra, n=Refractive index For TC:

$\phi_{TC}=\phi_{stand}(F_{TC}/F_{stand})\times(A_{stand}/A_{TC})\times(n_{TC}^2/n_{stand}^2)$ φ=Quantum yield, F=Area under fluorescence spectra, A=Absorption maxima, and n=Refractive index Molecular Docking Study:

Molecular docking is performed using AutoDock 4.2, and the AutoDock-Tools software is used to set up the necessary inputs for the docking program. The structure of fibril consisting of 5 amyloid beta peptides (PDB code 2BEG) is taken from the Protein Data Bank and is used as the protein model for docking in this study. The geometry of TC in gas phase is optimized at the level of B3LYP/6-31+G* using the Gaussian09 software. A grid box centered on the protein is defined with a dimension of 90×70×60 Å using a 0.375 Å grid step, which is large enough to encompass the whole protein and leave enough space for docking ligand on the surface. The Lamarckian Genetic Algorithm is used for ligand conformation search and is run for 100 times which would generate 100 possible protein-ligand complexes. All other parameters are left as default. The resulting ligand conformers are clustered by root mean square deviation (RMSD).

Example 16: Molecular Interactions Studies

Molecular Interactions Studies for Probe QC

Herein, a low molecular weight (>600 Da) Quinoline Coumarin (QC) based NIR fluorescent probe is used, which exhibits high fluorescence enhancement when binds to Aβ plaques. Selective fluorescence enhancement is shown by QC probe, with strong binding affinity. Probe QC has very good lipophilicity to cross the BBB and serum stability. QC detects Aβ plaques in CSF samples of patient which can be used in early diagnosis of Alzheimer's Disease. Probe QC is a molecular rotor moiety containing an electron withdrawing group in conjugation with an electron releasing group with a freely rotatable bond. Prevention of internal rotation in QC by surrounding medium rigidity, leads to a decrease in the non-radiative decay rate and an increase in fluorescence emission. With this approach photophysical studies of QC are performed; in absence of Aβ42 aggregates, QC (2 μM) shows an absorption maximum at 516 nm and a very weak fluorescence with maxima at 664 nm; in presence of Aβ monomers (10 μM) absorption maxima at 521 nm ($\lambda_{ex}$) and a ~7 fold fluorescence enhancement ($\lambda_{em}$=654 nm) is observed (FIG. 46). In presence of Aβ42 aggregates (10 μM) prepared in PBS buffer (10 mM), absorption maxima at 521 nm ($\lambda_{ex}$) and a blue shifted emission maxima (10 nm) with huge (>100 fold) fluorescence enhancement ($\lambda_{ex}$=654 nm) and a large stoke shift of ~130 nm is observed (FIG. 47). Change in fluorescence exhibited by QC (2 μM) is studied when it interacts with other peptide aggregates and biomacromolecules (FIG. 48) to analyse its selectivity. α-Synuclein (α-Syn) peptide and islet amyloid polypeptide (IAPP) are responsible for Parkinson's disease and type-2 diabetes mellitus respectively. These peptides are known to form fibrillar aggregates similar to Aβ42 aggregates. When QC is treated with preformed aggregates of α-Syn (20 μM) and IAPP (20 μM), it shows a negligible enhancement in fluorescence, and $\lambda_{em}$ maxima of α-Syn aggregates show a blue shift of ~9 nm. No such changes are observed in case of IAPP aggregates. When tested with BSA and calf thymus DNA (20 μM), BSA shows a red shift of ~34 nm ($\lambda_{em}$=616 nm) indicating binding of QC to BSA, but considerable fluorescence enhancement is not observed as in case of Aβ42 aggregates. Similarly, QC shows slight fluorescence enhancement when it binds to DNA (FIG. 49).

Molecular Interactions Studies for Probe TC and TP

The molecular interactions of TC and TP in the absence and presence of Aβ$_{42}$ aggregates are studied through the absorption and emission measurements in PBS buffer (10 mM, pH=7.4). Mature Aβ42 fibrillar aggregates are prepared following the procedure reported in the literature and as provided above. TC and TP show absorption bands at 537 nm and 460 nm, respectively, and very weak emissions at 638 nm and 623 nm, respectively, in the absence of Aβ42 aggregates (FIG. 61(b) and FIG. 65).

In the presence of Aβ42 aggregates (10 μM), TC (2 μM) shows a remarkable increase in the absorption maxima (hyperchromicity) with an enormous bathochromic shift (Δλmax≈59 nm) relating to solution color change from pale pink to purple (FIG. 66). To elucidate the observed spectral changes of TC, concentration-dependent studies of Aβ$_{42}$ aggregates are carried out against a fixed concentration of TC (2 μM). Initially, TC exhibits a decrease in absorption intensity in the concentration range 0-1 μM of Aβ42 aggregates. In addition, a shoulder band is observed for 0.8 μM of A42 at 595 nm. Further, with increasing concentration of Aβ$_{42}$ aggregates (1-10 μM) the shoulder band at 595 nm becomes more prominent with strong absorption (FIG. 62(a)). The bathochromic shift in the absorption band of TC, in presence of Aβ42 aggregates, indicates their favorable interactions. The observed colorimetric change (pale pink to purple) as a consequence of binding of TC to Aβ$_{42}$ aggregates may be attributed to aggregate-induced changes in the intramolecular alignment and electronic structure of TC. In similar absorption studies with Aβ42 aggregates, TP fails to exhibit any detectable change in absorption and in the color of the solution.

Molecular Study of Probe TC in Different Environments:

In order to characterize the aggregate-specific shift in the absorption spectrum of TC and to propose its absorption maximum as a "colorimetric signature" for amyloidosis, its one photon absorption properties are computed by employing time-dependent density functional theory (at the B3LYP/TZVP level) in polar, non-polar and fibril-like environments. In particular, static and dynamic results are presented where the former one involves a single optimized geometry of TC in the specific solvent environments, while the latter results are obtained as average over numerous configurations from Car-Parrinello QM/MM molecular dynamics. These models are respectively referred to as TD-DFT/PCM and TD-DFT/MM. The calculation only for the most stable binding mode of TC in fibril as shown in FIG. 61(c) has been carried out. Representative snapshots used in TD-DFT/MM calculations for TC/fibril and TC/water systems are shown in FIG. 67. Along with these, the results alone for TC without environment are presented (referred as TD-DFT/MM-0) in Table 5. Usually, when the dielectric nature of the micro-environment changes, not only the probes electronic structure (direct media effects) is altered but also its molecular structure (indirect media effects). The model referred as TD-DFT/MM-0 provides information about the shift in spectra arising from the latter indirect effects.

Table 5 depicts the absorption maximum in nm (with oscillator strength shown in parenthesis) for TC in different micro-environment as predicted from TD-DFT/PCM, and TD-DFT/MM approaches.

| Method | TC/chloroform | TC/fibril | TC/water | Shift, nm |
|---|---|---|---|---|
| Static (TD-DFT/PCM) | 528(1.9) | — | 514 (1.8) | 14 |
| Dynamic (TD-DFT/MM) | — | 551 (1.6) | 495 (1.5) | 56 |
| Experiment | 561 | 595 | 537 | 58 |

There are indeed cases where such indirect media effects can contribute significantly to the total shift. The spectra computed (by convoluting the absorption bands of six lowest energy excitations) using the static and dynamic models are shown in FIG. 61(d). As can be seen, the absorption spectrum is characterized by a single dominant band in the visible region which is due to the lowest frequency excitation of π-π* character. The molecular orbitals involved in this excitation are shown in the FIG. 68. The absorption maximum (λmax) for TC from the aforementioned models is listed in Table 5 along with the experimental results which show a red shift by 58 nm for the TC probe going into the fibril-like environment.

As can be seen, the simplistic polarizable continuum model reproduces the trend of a red-shift in the absorption spectra even though the size of the shift is much too small (14 nm) when compared to experiment (58 nm). Based on this result, it can be suggested that the hydrophilic-like to hydrophobic-like change in the micro-environment should be a feasible mechanism for the fibril-induced red-shift in the absorption spectra of TC. The more sophisticated TD-DFT/MM approach which accounts for electrostatic and polarization interactions between TC and its fibril-like and aqueous environment also confirm this and reproduce the red shift (56 nm) in excellent agreement with experiment. The values presented for the TD-DFT/MM-0 corresponds to the dynamic average obtained without including the environment explicitly, only referring to the indirect contributions to the shift originating from change in micro-environment. As can be seen, this is not significant (only contributes to 4 nm), which also is confirmed by the analyzed molecular structure of TC along the conjugation pathway, which does not change significantly.

The characterization of the microenvironment of TC binding site clarifies its hydrophobic nature, and the change in the hydrophilic-like to hydrophobic-like environment of TC when it binds to the fibril can be attributed as the responsible factor for the red shift.

Subsequently, fluorescence titration experiments are performed to probe the response of TC in the presence of $A\beta_{42}$ aggregates. The emission spectrum of TC (2 μM) exhibits a ~30-fold fluorescence enhancement ($E_{max}$=654 nm), with quantum yield of 40% upon binding with aggregates (FIG. 62(*b*)). Again, TP does not show any detectable change in the fluorescence behavior in the presence of $A\beta_{42}$ aggregates. TC forms twisted intramolecular charge transfer (TICT) complexes in the excited state and exhibit fluorescence emission in response to a surrounding environment. TC probe alone is non-fluorescence in buffer due to internal non-radiative molecular twisting and self-aggregation, whereas the intramolecular twisting is restricted upon binding to $A\beta_{42}$ aggregates leading to enhanced (~30-fold) red fluorescence.

Example 17: Binding Studies

Binding Studies for QC Probe

Affinity binding experiment is conducted, wherein to a solution of α-Syn aggregates (20 μM) or IAPP aggregates (20 μM) or DNA (20 μM) with probe QC (2 μM), Aβ42 aggregates are added and fluorescence is recorded, which shows enhanced emission comparable to the emission of a solution with Aβ42 aggregates (10 μM) and probe QC (2 μM) alone. The above studies indicate that probe QC can bind to different aggregates, but selective fluorescence enhancement is observed with Aβ42 aggregates only, thus showing high affinity of probe QC towards the Aβ42 aggregates.

Binding saturation assay is performed to study the binding affinity of probe QC towards Aβ42 aggregates, wherein to a fixed concentration of $A\beta_{42}$ aggregates (10 μM), increasing concentration of QC is added (0.052, 0.078, 0.102, 0.210, 0.5, 1 and 5 μM) and dissociation constants (Kd) are obtained. Dissociation constant of 82±2.3 nM (binding constant (Ka), 12.14±0.43 μM) is obtained, which is much lower than compared to Kd of thioflavin T (ThT) and Congo red (FIG. 49). QC showed a quantum yield of 0.08, while after binding to Aβ42 aggregates it shows a quantum yield of 0.36. To further interrogate the binding affinity of probe QC, displacement assay is performed against ThT bound Aβ42 aggregates. Remarkably, gradual addition of QC to the ThT/Aβ42 aggregate complex (ThT: 10 μM and Aβ42: 20 μM) results in steady decay in fluorescence at 483 nm ($\lambda_{ex}$=450 nm) and a corresponding enhancement in the emission intensity at 654 nm ($\lambda_{ex}$=521 nm). The decrease in emission of ThT at 483 nm and corresponding increase in emission of QC at 654 nm suggest effective displacement of ThT by QC to form stronger QC/Aβ42 aggregate complex (FIG. 50, FIG. 51 and FIG. 52). An interesting observation is made during the titration studies where spectral features corresponding to the emission of probe QC (at 654 nm) is observed upon excitation of the sample (QC/ThT/Aβ42 aggregates) at 450 nm (ThT excitation wavelength). Initially, with the addition of QC (0 to 20 μM) to ThT/Aβ42 aggregates complex gradual decrease in the fluorescence emission at 483 nm (ThT) is shown as expected (state A). Surprisingly, fluorescence is also observed at 654 nm (QC), which shows a gradual decay in fluorescence intensity with further increase in the concentration of QC (state B) and finally shows negligible fluorescence (state C) at 654 nm ($\lambda_{ex}$=450 nm) (FIG. 53). These changes in the emission characteristics, particularly the fluorescence emission of QC upon excitation corresponding to ThT can be attributed to fluorescence resonance energy transfer (FRET) between Aβ42 aggregates bound ThT and QC. The FRET and displacement studies of QC towards ThT/Aβ42 fibrils complex has been depicted in FIG. 58. Evidently, the emission spectrum of ThT significantly overlaps with the absorption spectrum of QC making them a suitable donor-acceptor pair (FIG. 53). At the beginning of titration, QC binds to ThT/Aβ42 aggregate complex by displacing some of ThT leading to FRET between bound ThT (donor) and QC (acceptor) (FIG. 54). For concentrations of QC>3 μM, displacement of ThT by QC results in a decrease in FRET-based fluorescence of QC. With gradual increase in concentration of QC, all the ThT bound to Aβ42 aggregates were completely displaced by QC, which leads to the diminishing of fluorescence intensity at both 483 nm and 654 nm ($\lambda_{ex}$=450 nm). ThT is known to have majorly three types of binding sites BS1, BS2 and BS3 of which BS1 and BS2 are most populated sites. In the above displacement assay, excitation at 521 nm shows a gradual increase in fluorescence independent of ThT displacement indicating the presence of more than three binding sites for QC on Aβ42 aggregates in comparison to ThT. The binding of TC to the Aβ42 aggregates has been depicted in FIG. 60.

Binding Studies for Probe TC

The binding constant of TC is calculated by studying the fluorescence response with varying concentration of TC against a fixed concentration of Aβ42 aggregates (dose-dependent saturation assay, FIG. 69). The obtained standard saturation curve is fitted to a single-binding site, which generates a dissociation constant Kd of 58±1.2 nM (The association constant is calculated to be Ka=1.72×10$^7$ M$^{-1}$ for 2 μM of Aβ42 aggregates) (FIG. 63(*a*)). Remarkably, the current study reveals a ~30-fold fluorescence enhancement with Kd in the nanomolar range indicating a high binding affinity of TC towards $A\beta_{42}$ aggregates. In addition, the Kd of Aβ42 aggregates bound TC is very low compared to that of the control probes ThT (~0.8 M) and Congo red (~1.1 M) confirming the superiority of the TC probe in terms of binding affinity towards Aβ42 aggregates. To examine the selectivity of TC towards Aβ42 aggregates, fluorescence studies are performed in the presence of intracellular protein content bovine serum albumin (BSA) and fibrillar aggregates of α-synuclein (α-Syn) and islet amyloid polypeptide (IAPP, amylin) implicated in Parkinsons disease and type II diabetes, respectively. Incubation of TC with BSA, α-Syn aggregates and IAPP aggregates (20 μM) does not lead to significant fluorescence enhancements confirming the preferential selectivity of the probe towards Aβ42 aggregates over other proteins and peptide aggregates (FIG. 63(*b*)).

To gain further insight into the binding affinity of the TC probe, a displacement assay is performed against ThT-bound Aβ42 aggregates. The well-separated emission spectra of ThT (green region) and TC (red region) makes it possible to observe fluorescence changes corresponding to individual probes during the displacement experiments. Remarkably, a gradual addition of TC to the ThT/A$\beta_{42}$ aggregate complex (ThT: 5 μM and Aβ$_{42}$: 10 μM) results in a steady decay in fluorescence at 483 nm ($\lambda_{ex}$=450 nm) and a corresponding enhancement in the emission intensity at 654 nm ($\lambda_{ex}$=537 nm) (FIG. 68). This clearly suggests an effective displacement of ThT by TC owing to the formation of a much stronger TC/Aβ$_{42}$ aggregate complex (FIG. 64(a)). An interesting observation is made during the titration studies wherein spectral features corresponding to emission of TC (at 654 nm) are observed upon excitation of the sample (TC/ThT/Aβ$_{42}$ aggregates) at 450 nm (ThT excitation wavelength). Addition of TC (33 nM to 10.233 µM) to the ThT/Aβ$_{42}$ aggregates complex shows a gradual decrease in the fluorescence emission at 483 nm (ThT) as expected. However, upon 450 nm (ThT) excitation, fluorescence is also observed at 654 nm (TC) with a slight red shift. The fluorescence intensity of this unprecedented emission band (TC) decreases slowly with further increase in the concentration of added TC and finally reaches a constant value (FIG. 64(b)).

These changes in the emission characteristics, particularly the fluorescence emission of TC upon excitation corresponding to ThT is attributed to fluorescence resonance energy transfer (FRET) between the Aβ$_{42}$ aggregates bound to ThT and TC. Evidently, the emission spectrum of ThT significantly overlaps with the absorption spectrum of TC making them a suitable donor-acceptor pair on the aggregate surface (FIG. 69(b)). At the beginning of the titration, TC binds to the ThT/Aβ$_{42}$ aggregate complex by partially displacing ThT, leading to FRET between bound ThT (donor) and TC (acceptor) (FIG. 64(b)). For concentrations of TC>150 nM, displacement of ThT by TC results in a decreased FRET-fluorescence of TC (FIG. 70). However, the FRET-based fluorescence at 654 nm is not quenched completely due to persistent residual ThT-TC pairs on A142 aggregate (FIG. 73). The complete quenching of fluorescence intensity of ThT (at 483 nm) indicates that TC binds to similar primary binding pockets of Aβ$_{42}$ aggregates occupied by ThT. On the other hand, excitation at 537 nm (TC) shows a gradual increase in fluorescence independent of ThT displacement, confirming the presence of multiple binding sites for TC on Aβ$_{42}$ fibrillar aggregates (FIG. 73). The displacement of ThT is almost instantaneous and does not require any incubation time.

Addition of TC (1 µM) to the ThT (10 µM)/Aβ$_{42}$ (50 µM) complex leads to a complete change in emission color of the sample, from green to bright pinkish red, as seen under UV-light illumination ($\lambda_{ex}$=365 nm). Addition of excess ThT (50 µM) does not displace TC from its complex with Aβ$_{42}$ aggregates owing to the high binding constant (FIG. 71). The Aβ$_{42}$ aggregates stained with TC retain red fluorescence even after 50 days of aging, thus further indicating the strong binding affinity and non-dissociative nature of TC upon binding to Aβ$_{42}$ aggregates.

In order to get a microscopic picture of the TC to fibril binding, molecular docking study is carried out. The study shows that that there are multiple binding sites (such as entry cleft and surface) in the fibril accessible for binding of TC (FIG. 73(a)). However, the most favorable binding site is identified in the entry site formed by Leu17, Val18, Phe19, Gly38, Val39 and Val40 (FIG. 61(c)). The binding affinity calculated by AutoDock is the highest in this site (about ~8.5 kcal/mol), whereas in other sites, it is in the range of −6.0 to ~−8.0 kcal/Mol. A flexible molecular model for TC during the docking yields a binding affinity equivalent to −9.86 kcal/mol which corresponds to $K_d$ 55.5 nM (which is in good agreement with experimental data).

As TC is positively charged, it is unfavorable to bind in the inner sites which are fully buried, and the partially buried entry site is more favorable. FIG. 61(c) shows that TC is clamped in the entry site mainly through hydrophobic interaction with Leu17 and Val39 through pi-pi stacking interaction with the phenyl ring of Phe19. Water molecules can also enter this site to solvate the positive charge of TC. It is relevant to note that all the amino acids forming this binding pocket are hydrophobic and hence the red shift in the spectra is due to the change from hydrophilic to hydrophobic like micro-environment. Further, the bulky nature of the diethyl amino group makes it impossible for the TC probe to become buried inside the binding site; rather it is partly exposed to the solvent environment (FIG. 67(a)). FIGS. 73(a) and 73(b) show all possible binding sites available for TC and ThT in the fibril. The ThT binds to the entry cleft, inner core and surface binding sites while TC binds only to the entry cleft and the surface binding sites which have to be attributed to the larger van der Waals surface associated with the latter molecule. Due to the larger binding affinity of TC towards the amyloid peptide, it can replace the ThTs in the entry cleft and other surface binding sites (which is supported by FRET data above). However, ThTs in the core sites cannot be displaced by TCs and these therefore contribute to the population of residual ThT-TC pairs on Aβ$_{42}$ aggregate contributing to significant FRET intensity as discussed above.

Example 18: Stability Studies

Stability Studies for QC

The in vitro stability of QC in mouse serum is determined by incubating QC (10 µM in H$_2$O, 50 µM) with 300 µL of human blood serum at 37° C. for 30 and 60 min. Proteins are precipitated by adding 500 µL of acetonitrile after centrifugation at 5000 rpm for 5 min at 4° C. The supernatant is collected. Approximately 0.1 mL of the supernatant solution is analyzed using HPLC.

Log P values for probe QC is evaluated as 2.4 using the flask shake method, suggesting that QC possesses desirable lipophilicity to cross the BBB efficiently. In addition to that, stability in the blood and low cytotoxicity are two important properties for a good NIR probe. In vitro stability studies indicate that QC has high in vitro stability in human blood serum (HBS), and more than 97% of the probe is identified intact after 60 min of incubation with HBS at 37° C. (FIG. 55).

Example 19: Selective Detection of Aβ42 Aggregates Expressed in *S. Cerevisiae* Cell β-amyloid (13-42) and α-synuclein (A30P) expressing *S. cerevisiae* (BY4741) strains are used for this study. Both inserts are under inducible GAL promoter and are GFP tagged at their C terminus. Neurotoxic aggregate containing strains are inoculated into YPD (Yeast Extract, Peptone and Dextrose) medium and incubated overnight (30° C., 250 rpm). Secondary culture is inoculated (0.2 A$_{600}$) from primary inoculum, and incubated as above till culture absorbance reaches 0.8 A$_{600}$. The culture are washed twice, aggregates are induced with D (+) galactose (2%) and incubated for 24 hours. The dye QC (5 µM) is added during galactose induction.

QC is tested on *S. cerevisiae* (BY47 41) strains expressing Aβ42 and α-synuclein (A30P) aggregates. Remarkably, the probe QC stains *S. cerevisiae* expressing Aβ42 aggregates selectively and *S. cerevisiae* strains with α-synuclein (A30P) aggregates are not stained. Co-localisation of Aβ42 aggregates and QC is visualized using fluorescence microscopy. The fluorescence co-localization analysis reveals that when the GFP tagged Aβ42 aggregates are treated with the probe QC, a high fluorescence correlation coefficient (83.7%) is obtained. In the live cells counted (n=50), the mean Pearson co-localization coefficient is 0.837 and the representative images can be seen in FIG. 56.

Example 20: pH Dependent Study

A pH-dependent study is performed to explore the involvement of acid-base interactions between TC and the binding pockets of the $A\beta_{42}$ fibrillar aggregates (FIG. 72). The absorbance and fluorescence spectra at different pH values reveal that the colorimetric and emission properties of TC are unaffected in broader pH range of 3 to 8. This study reveals that the binding of TC to $A\beta_{42}$ aggregates does not occur through acid-base interactions, but rather involves hydrophobic and other noncovalent interactions.

Example 21: Detection of Amyloid Plaques for Diagnosis of Alzheimer's Disease (AD)

The diagnosis of AD is a major concern in present scenario, where detection of certain over expressed proteins (biomarkers) during AD can provide a path for early diagnosis. Searching biomarkers in blood, urine or tears has not been so successful whereas CSF has provided some promising results as CSF is in close proximity to the brain and therefore, any change in the chemical environment of the brain will be reflected in CSF.

In the present experiment, Amyloid plaques in the CSF sample are detected as it is a hallmark of AD using ThT and QC. QC (10 μM) or ThT (20 μM) in Millipore water is mixed with CSF and the sample volume is made up to 1 mL. The emission is recorded at 521 nm and 483 nm, keeping the excitation wavelength at 653 nm and 450 nm for QC and ThT respectively.

Accordingly, a series of CSF samples (300 μL) are screened from different age groups using thioflavin assay (ThT: 20 μM) and four samples positive for the assay are detected (CSF3, CSF5, CSF6 and CSF12). QC (10 μM) is used to detect Aβ plaques in the same set of CSF samples, which show the same trend as Thioflavin assay and stains CSF3, CSF5, CSF6 and CSF12 samples (FIG. 57 and table 6).

Table 6 depicts detection of amyloid plaques in CSF samples.

| Sample | Age | Normalized fluorescence intensity (ThT) | Normalized fluorescence intensity (QC) |
|---|---|---|---|
| CSF1 | 55 | 14.35 | 12.50 |
| CSF2 | 55 | 5.60 | 3.24 |
| CSF3 | 50 | 18.25 | 29.60 |
| CSF4 | 55 | 7.45 | 10.70 |
| CSF5 | 60 | 40.65 | 51.50 |
| CSF6 | 60 | 24.40 | 29.60 |
| CSF7 | 60 | 5.75 | 6.40 |
| CSF8 | 65 | 8.40 | 11.08 |
| CSF9 | 68 | 7.50 | 6.30 |
| CSF10 | 63 | 3.26 | 5.40 |
| CSF11 | 75 | 8.35 | 6.70 |
| CSF12 | 79 | 37.50 | 44.40 |
| CSF13 | 77 | 4.20 | 3.20 |
| CSF14 | 75 | 4.52 | 12.30 |

In conclusion, the compounds of formula VI (CL) and VII (QC) are found to be efficient fluorescent probes for detection of Aβ aggregates. These probes selectively fluoresce when bound to Aβ42 aggregates and have an excellent binding affinity towards Aβ42 aggregates when compared to commercial staining reagents. They are biocompatible, serum stable and nontoxic to the neuronal cells. They stain $A\beta_{42}$ aggregates expressed by *S. cerevisiae* (BY4741) strains and Aβ plaques present in brain tissue of an Alzheimer's patient. Aβ plaques are detected in CSF samples using the above mentioned probes, which are useful in diagnosis of diseases such as Frontotemporal dementia and AD. Therefore the use of these fluorescent probes in diagnostic kits is a promising approach for the diagnosis of AD and Frontotemporal dementia when compared to other techniques present in market.

Similarly compounds of formula I and their dimers bind to $A\beta_{42}$ aggregates with nanomolar affinity (Ka=1.72×10$^7$ M$^{-1}$). The probes show a switch-on red fluorescence with a large Stokes shift (~117 nm) upon binding to $A\beta_{42}$ aggregates along with a characteristic colorimetric response (pale pink to purple) which can be attributed to a change in the dielectric nature of micro-environment of these probes from hydrophilic-like to hydrophobic-like. These probes also show good specificity as they do not interact with other abnormal protein aggregates of β-Syn and IAPP. Owing to high binding affinity, the probes displace the ThT probe bound to $A\beta_{42}$ aggregates, conversely very high concentrations of ThT cannot not displace TC bound to $A\beta_{42}$ aggregates. With an appropriate balance of hydrophobicity and hydrophilicity, these probes are most likely to cross the blood brain barrier, as further supported by the log P value. The binding site in the $A\beta_{42}$ fibril for TC has been revealed from molecular docking studies. Therefore, these probes are useful for optimization of $A\beta_{42}$ aggregates and therefore help in diagnosis of disease conditions such as Alzheimer's disease and Frontotemporal dementia.

Thus, it can be observed that the compounds of the instant disclosure function as excellent probes for detecting AT rich sequences of DNA and Aβ aggregates. Therefore, the compounds of the instant disclosure play a crucial role in diagnosing various parasitic infections such as malaria as well as neurodegenerative conditions such as Alzheimers disease and Frontotemporal Dementia.

We claim:

1. A method of detecting DNA comprising AT bases or Amyloid β and its aggregate, the method comprising:

contacting a sample with a compound of formula I

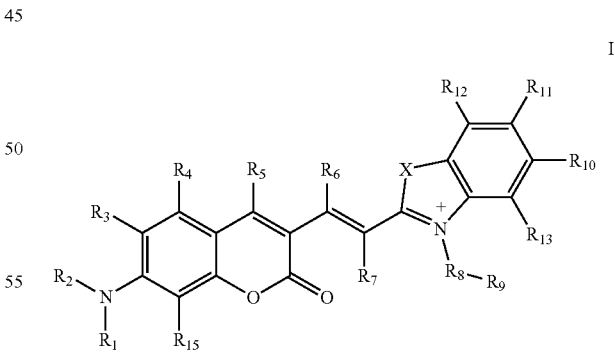

wherein,

X is selected from a group consisting of oxygen, sulphur, and selenium;

R1 is selected from a group consisting of methyl, ethyl, propyl, and chloroethyl;

R2 is selected from a group consisting of methyl, ethyl, propyl, and chlorethyl;

R3, R4, R5, R6, and R7 are each H;
R8 is selected from a group consisting of $CH_3$ and $CH_{2n}$, wherein 'n' is 1, 2, 3, 4, 5, or 6, wherein the R8 is linked to R9 when the R8 is the $CH_{2n}$;
the R9 is selected from a group consisting of bromine, quaternary ammonium, ethyne, and carboxylic acids;
R10, R11, R12, R13, and R15 are each H;
wherein, optionally R2 and R3, R1 and R15 form a 2, 3, 6, 7 tetrahydro-quinolizine (quinolizidine),
for detecting DNA comprising AT bases or Amyloid β and its aggregate in the sample.

2. The method in claim 1, wherein the method involves spectroscopy, Fluorescence Resonance Energy Transfer (FRET), polymerase chain reaction, flow cytometry, gel electrophoresis, nuclear staining, and imaging or any combinations thereof.

3. The method in claim 1, wherein the compound is selected from a group consisting of (E)-3-(2-(N-methyl-benzo[d]oxazol-2-yl)vinyl)-7-(diethylamino)-2H-chromen-2-one, (E)-3-(2-(N-methyl-benzo[d][1,3]selenazol-2-yl)vinyl)-7-(diethylamino)-2H-chromen-2-one, (E)-3-(2-(N-(prop-2-ynyl)-benzo[d]thiazol-2-yl)vinyl)-7-(diethylamino)-2H-chromen-2-one, (E)-3-(2-(N—(N,N,N-trimethyl-2-aminoethyl)-benzo[d]thiazol-2-yl)vinyl)-7-(diethylamino)-2H-chromen-2-one, (E)-3-(2-(N-(2-aminium ethyl)-benzo[d]thiazol-2-yl)vinyl)-7-(diethylamino)-2H-chromen-2-one, (E)-3-(2-(N—(N,N,N-trimethyl-3-aminopropyl)-benzo[d]thiazol-2-yl)vinyl)-7-(diethylamino)-2H-chromen-2-one, (E)-3-(2-(N-(prop-2-ynyl)-benzo[d]oxazol-2-yl)vinyl)-7-(diethylamino)-2H-chromen-2-one, (E)-3-(2-(N—(N,N,N-trimethyl-2-aminoethyl)-benzo[d]oxazol-2-yl)vinyl)-7-(diethylamino)-2H-chromen-2-one, (E)-3-(2-(N-(2-aminium ethyl)-benzo[d]oxazol-2-yl)vinyl)-7-(diethylamino)-2H-chromen-2-one, (E)-3-(2-(N—(N,N,N-trimethyl-3-aminopropyl)-benzo[d]oxazol-2-yl)vinyl)-7-(diethylamino)-2H-chromen-2-one, (E)-3-(2-(N-methyl-benzo[d]thiazol-2-yl)vinyl)-7-(dimethylamino)-2H-chromen-2-one, (E)-3-(2-(N-methyl-benzo[d]thiazol-2-yl)vinyl)-7-(dipropylamino)-2H-chromen-2-one, 2,3,6,7-Tetrahydro-8-hydroxy-1H,5H-benzo[ij]quinolizine-9-carboxaldehyde (Thiazole Julidinal), (E)-3-(2-(N-(prop-2-ynyl)-benzo[d]thiazol-2-yl)vinyl)-7-(diethylamino)-2H-chromen-2-one, (E)-3-(2-(N-(4-bromobutyl)-benzo[d]thiazol-2-yl)vinyl)-7-(diethylamino)-2H-chromen-2-one, and (E)-3-(N-Methyl2-(benzo[d]thiazol-2-yl)vinyl)-7(bis(2-chloroethyl)amino)-2H-chromen-2-one.

* * * * *